US012595246B2

(12) United States Patent
Greco et al.

(10) Patent No.: US 12,595,246 B2
(45) Date of Patent: Apr. 7, 2026

(54) CRYSTALLINE AND AMORPHOUS FORMS OF N-(5-((4-ETHYLPIPERAZIN-1-YL) METHYL)PYRIDINE-2-YL)-5-FLUORO-4-(3-ISOPROPYL-2-METHYL-2H-INDAZOL-5-YL)PYRIMIDIN-2-AMINE AND ITS SALTS, AND PREPARATION METHODS AND THERAPEUTIC USES THEREOF

(71) Applicant: BETA PHARMA, INC., Wilmington, DE (US)

(72) Inventors: Michael Nicholas Greco, Lanesdale, PA (US); Michael John Costanzo, Warminster, PA (US); Jirong Peng, Mequon, WI (US); Don Zhang, Princeton, NJ (US)

(73) Assignee: BETA PHARMA, INC., Wilmington, DE (US)

( * ) Notice: Subject to any disclaimer, the term of this patent is extended or adjusted under 35 U.S.C. 154(b) by 1147 days.

(21) Appl. No.: 17/440,398

(22) PCT Filed: Mar. 20, 2020

(86) PCT No.: PCT/US2020/023828

§ 371 (c)(1),
(2) Date: Sep. 17, 2021

(87) PCT Pub. No.: WO2020/191283

PCT Pub. Date: Sep. 24, 2020

(65) Prior Publication Data

US 2022/0162185 A1 May 26, 2022

Related U.S. Application Data

(60) Provisional application No. 62/821,141, filed on Mar. 20, 2019.

(51) Int. Cl.
*C07D 401/14* (2006.01)
*A61P 35/00* (2006.01)

(52) U.S. Cl.
CPC ............ *C07D 401/14* (2013.01); *A61P 35/00* (2018.01); *C07B 2200/13* (2013.01)

(58) Field of Classification Search
None
See application file for complete search history.

(56) References Cited

U.S. PATENT DOCUMENTS

| | | | | |
|---|---|---|---|---|
| 9,878,994 | B2 * | 1/2018 | Greco | C07D 401/14 |
| 10,239,864 | B2 * | 3/2019 | Greco | A61P 29/00 |
| 10,626,107 | B2 * | 4/2020 | Ding | C07D 401/14 |
| 2017/0210726 | A1 | 7/2017 | Greco et al. | |
| 2018/0072707 | A1 | 3/2018 | Ding et al. | |
| 2018/0148431 | A1 * | 5/2018 | Greco | A61P 19/02 |

FOREIGN PATENT DOCUMENTS

WO 2018045993 A1 3/2018

OTHER PUBLICATIONS

International Search Report Issued in Application No. PCT/US2020/023828 on Jul. 28, 2020, 4 pages.
Written Opinion Issued in Application No. PCT/US2020/023828 on Jul. 28, 2020, 8 pages.
Partial Supplementary European Search Report for European Application No. 20772535.9, dated Nov. 25, 2022, 9 pages.
Extended European Search Report for European Application No. 20772535.9, dated Feb. 10, 2023, 9 pages.
Balbach et al., "Pharmaceutical evaluation of early development candidates, The 100 mg approach," International Journal of Pharmaceutics, (2004), vol. 275, pp. 1-12.
Caira, Mino R., "Crystalline polymorphism of Organic Compounds", Topics in Current Chemistry, vol. 198, p. 163-208 (1998).
Singhal et al.; "Drug Polymorphism and Dosage Form Design: A Practical Perspective"; Advanced Drug Delivery Reviews: 56; pp. 335-347; (2004).

* cited by examiner

*Primary Examiner* — John S Kenyon
*Assistant Examiner* — Rehana Ismail
(74) *Attorney, Agent, or Firm* — CANTOR COLBURN LLP

(57) ABSTRACT

Crystalline and amorphous forms of N-(5-((4-ethylpiperazin-1-yl)methyl)pyridin-2-yl-5-fluoro-4-(3-iso-propyl-2-methyl-2H-indazol-5-yl)pyrimidin-2-amine (Compound 1) and various salts thereof, preparation methods of these crystalline and amorphous forms, pharmaceutical compositions containing these crystalline or amorphous forms, and use of these crystalline and amorphous forms, or pharmaceutical compositions thereof, for treatment of diseases or disorders associated with cyclin-dependent kinase (CDK), especially CDK4 and CDK6, activities, such as various cancers, are disclosed.

7 Claims, 51 Drawing Sheets

[C15051812-API.raw] — Peak Search Report

SCAN: 4.0/39.9779/0.01972/18.6(sec), Cu(40kV,40mA), I(max)=4569, 10/20/17 10:14

PEAK: 19-pts/Parabolic Filter, Threshold=5.0, Cutoff=1.0%, BG=3/0.5, Peak-Top=Summit NOTE: Intensity = Counts, 2T(0)=0.0(°), Wavelength to Compute d-Spacing = 1.54056A(Cu/K-alpha1)

| # | 2-Theta | d(A) | BG | Height | I% | Area | I% | FWHM |
|---|---|---|---|---|---|---|---|---|
| 1 | 5.616 | 15.7224 | 487 | 1545 | 37.3 | 30387 | 40.2 | 0.330 |
| 2 | 5.933 | 14.8833 | 431 | 4138 | 100.0 | 75633 | 100.0 | 0.306 |
| 3 | 6.741 | 13.1018 | 372 | 157 | 3.8 | 2008 | 2.7 | 0.214 |
| 4 | 9.342 | 9.4586 | 250 | 199 | 4.8 | 2558 | 3.4 | 0.216 |
| 5 | 10.546 | 8.3817 | 293 | 176 | 4.3 | 1381 | 1.8 | 0.132 |
| 6 | 11.415 | 7.7453 | 458 | 135 | 3.3 | 1030 | 1.4 | 0.128 |
| 7 | 11.851 | 7.4611 | 386 | 518 | 12.5 | 7569 | 10.0 | 0.245 |
| 8 | 13.902 | 6.3649 | 388 | 187 | 4.5 | 4354 | 5.8 | 0.390 |
| 9 | 14.139 | 6.2587 | 389 | 222 | 5.4 | 3573 | 4.7 | 0.270 |
| 10 | 16.465 | 5.3794 | 502 | 253 | 6.1 | 4191 | 5.5 | 0.278 |
| 11 | 17.963 | 4.9339 | 409 | 164 | 4.0 | 1682 | 2.2 | 0.172 |
| 12 | 18.990 | 4.6694 | 419 | 125 | 3.0 | 2136 | 2.8 | 0.286 |
| 13 | 20.411 | 4.3474 | 379 | 199 | 4.8 | 1855 | 2.5 | 0.156 |
| 14 | 21.102 | 4.2066 | 350 | 199 | 4.8 | 3323 | 4.4 | 0.280 |
| 15 | 25.598 | 3.4771 | 505 | 668 | 16.1 | 8957 | 11.8 | 0.225 |
| 16 | 26.209 | 3.3974 | 490 | 477 | 11.5 | 7151 | 9.5 | 0.251 |

Figure 2B

[C13951812-Acetone-Wet.raw] Peak Search Report

SCAN: 4.5/39.9779/0.01973/18.6(sec), Cu(40kV,40mA), I(max)=13468, 10/20/17 10:16

PEAK: 13-pts/Parabolic Filter, Threshold=5.0, Cutoff=1.0%, BG=3/1.0, Peak-Top=Summit NOTE: Intensity = Counts, 2T(0)=0.0(°), Wavelength to Compute d-Spacing = 1.54056Å(Cu/K-alpha1)

| # | 2-Theta | d(A) | BG | Height | I% | Area | I% | FWHM |
|---|---|---|---|---|---|---|---|---|
| 1 | 5.698 | 15.4977 | 323 | 1747 | 13.3 | 11421 | 13.9 | 0.110 |
| 2 | 6.382 | 13.8387 | 358 | 13158 | 100.0 | 83203 | 100.0 | 0.105 |
| 3 | 7.828 | 11.2845 | 224 | 285 | 2.2 | 1812 | 2.2 | 0.107 |
| 4 | 9.220 | 9.5833 | 166 | 1157 | 8.8 | 8603 | 8.0 | 0.096 |
| 5 | 11.382 | 7.7676 | 164 | 259 | 2.0 | 1374 | 1.7 | 0.089 |
| 6 | 12.118 | 7.3002 | 161 | 213 | 1.6 | 1282 | 1.5 | 0.099 |
| 7 | 12.758 | 6.9342 | 132 | 2884 | 22.0 | 16340 | 19.6 | 0.095 |
| 8 | 13.096 | 6.7547 | 230 | 1960 | 14.9 | 10664 | 12.8 | 0.090 |
| 9 | 15.680 | 5.6470 | 174 | 2779 | 21.1 | 17806 | 20.7 | 0.103 |
| 10 | 16.268 | 5.4440 | 165 | 291 | 2.2 | 1504 | 1.8 | 0.087 |
| 11 | 17.278 | 5.1281 | 169 | 1001 | 7.6 | 8605 | 9.7 | 0.134 |
| 12 | 18.770 | 4.7236 | 186 | 208 | 1.6 | 1580 | 1.8 | 0.126 |
| 13 | 19.384 | 4.5274 | 184 | 1078 | 8.2 | 9162 | 11.1 | 0.142 |
| 14 | 20.685 | 4.2905 | 160 | 1485 | 11.3 | 9832 | 12.8 | 0.111 |
| 15 | 22.918 | 3.8776 | 134 | 212 | 1.6 | 2057 | 2.5 | 0.165 |
| 16 | 23.287 | 3.8168 | 164 | 218 | 1.7 | 1130 | 1.4 | 0.087 |
| 17 | 23.884 | 3.7226 | 152 | 338 | 2.6 | 2640 | 3.2 | 0.132 |
| 18 | 24.755 | 3.5935 | 138 | 395 | 3.0 | 3362 | 4.1 | 0.143 |
| 19 | 25.327 | 3.5136 | 135 | 1103 | 8.4 | 8349 | 10.2 | 0.127 |
| 20 | 25.639 | 3.4716 | 129 | 206 | 1.6 | 1911 | 2.3 | 0.156 |
| 21 | 26.349 | 3.3797 | 113 | 275 | 2.1 | 1885 | 2.4 | 0.122 |
| 22 | 28.244 | 3.1571 | 139 | 249 | 1.9 | 1640 | 2.0 | 0.110 |
| 23 | 28.715 | 3.1063 | 140 | 249 | 1.9 | 1838 | 2.2 | 0.124 |
| 24 | 30.188 | 2.9580 | 138 | 120 | 0.9 | 1046 | 1.5 | 0.148 |

Figure 5A

[C13801812-Acetone-Dry.raw] Peak Search Report

SCAN: 4.0/39.9779/0.01973/18.6(sec), Cu(40kV,40mA), I(max)=11064, 10/30/17 10:15

PEAK: 13-pts/Parabolic Filter, Threshold=5.0, Cutoff=1.0%, BG=3/0.5, Peak-Top=Summit NOTE: Intensity = Counts, 2T(0)=0.0(°), Wavelength to Compute d-Spacing = 1.54056Å(Cu/K-alpha1)

| # | 2-Theta | d(A) | BG | Height | I% | Area | I% | FWHM |
|---|---|---|---|---|---|---|---|---|
| 1 | 5.676 | 15.5581 | 357 | 1845 | 17.1 | 13543 | 17.6 | 0.123 |
| 2 | 6.346 | 13.9124 | 321 | 10743 | 100.0 | 77179 | 100.0 | 0.120 |
| 3 | 7.803 | 11.3201 | 203 | 289 | 2.7 | 1703 | 2.2 | 0.098 |
| 4 | 9.187 | 9.6182 | 164 | 1015 | 9.4 | 6518 | 8.4 | 0.108 |
| 5 | 11.376 | 7.7717 | 135 | 267 | 2.5 | 1856 | 2.4 | 0.112 |
| 6 | 12.091 | 7.3139 | 189 | 276 | 2.6 | 1410 | 1.8 | 0.088 |
| 7 | 12.722 | 6.9525 | 187 | 2339 | 21.8 | 14910 | 19.3 | 0.107 |
| 8 | 13.074 | 6.7662 | 210 | 1753 | 16.3 | 10516 | 13.6 | 0.101 |
| 9 | 15.858 | 5.5849 | 157 | 2717 | 25.3 | 19029 | 24.7 | 0.117 |
| 10 | 16.253 | 5.4555 | 139 | 299 | 2.8 | 1940 | 2.5 | 0.108 |
| 11 | 17.258 | 5.1341 | 149 | 1057 | 9.8 | 9330 | 12.1 | 0.148 |
| 12 | 18.750 | 4.7288 | 195 | 247 | 2.3 | 1577 | 2.0 | 0.107 |
| 13 | 19.110 | 4.6404 | 164 | 991 | 9.2 | 8877 | 11.5 | 0.150 |
| 14 | 20.691 | 4.2875 | 138 | 1323 | 12.3 | 9357 | 12.1 | 0.119 |
| 15 | 22.891 | 3.8834 | 133 | 219 | 2.0 | 1911 | 2.3 | 0.133 |
| 16 | 23.232 | 3.8256 | 153 | 148 | 1.4 | 986 | 1.3 | 0.111 |
| 17 | 23.864 | 3.7257 | 137 | 351 | 3.3 | 3018 | 3.9 | 0.144 |
| 18 | 24.751 | 3.5941 | 138 | 331 | 3.1 | 2955 | 3.8 | 0.152 |
| 19 | 25.323 | 3.5143 | 131 | 1089 | 10.1 | 9154 | 11.9 | 0.141 |
| 20 | 25.663 | 3.4763 | 139 | 147 | 1.4 | 900 | 1.2 | 0.102 |
| 21 | 26.318 | 3.3840 | 106 | 222 | 2.1 | 1571 | 2.0 | 0.119 |
| 22 | 28.234 | 3.1582 | 150 | 220 | 2.0 | 1376 | 1.8 | 0.105 |
| 23 | 28.692 | 3.1082 | 137 | 242 | 2.3 | 2040 | 2.6 | 0.141 |
| 24 | 30.122 | 2.9644 | 108 | 132 | 1.2 | 1286 | 1.7 | 0.163 |

Figure 5B

| [C15051812-Ethanol-Dry.raw] | | | | | | | | Peak Search Report |
|---|---|---|---|---|---|---|---|---|
| SCAN: 4.0/39.9779/0.01972/18.6(sec), Cu(40kV,40mA), I(max)=7112, 10/20/17 10:15 | | | | | | | | |
| PEAK: 15-pts/Parabolic Filter, Threshold=5.0, Cutoff=1.0%, BG=3/0.5, Peak-Top=Summit | | | | | | | | |
| NOTE: Intensity = Counts, 2T(0)=0.0(°), Wavelength to Compute d-Spacing = 1.54056A(Cu/K-alpha1) | | | | | | | | |
| # | 2-Theta | d(A) | BG | Height | I% | Area | I% | FWHM |
| 1 | 4.729 | 18.6688 | 414 | 6698 | 100.0 | 54918 | 100.0 | 0.137 |
| 2 | 8.062 | 10.9575 | 162 | 240 | 3.6 | 1631 | 3.0 | 0.114 |
| 3 | 11.196 | 7.8965 | 152 | 2883 | 43.0 | 22883 | 41.7 | 0.133 |
| 4 | 14.061 | 6.2933 | 136 | 1280 | 19.1 | 10579 | 19.3 | 0.139 |
| 5 | 14.375 | 6.1564 | 151 | 361 | 5.4 | 3187 | 5.8 | 0.147 |
| 6 | 15.300 | 5.7862 | 133 | 672 | 10.0 | 6722 | 12.2 | 0.168 |
| 7 | 16.147 | 5.4847 | 145 | 126 | 1.9 | 705 | 1.3 | 0.094 |
| 8 | 17.117 | 5.1759 | 139 | 136 | 2.0 | 880 | 1.6 | 0.122 |
| 9 | 17.747 | 4.9937 | 131 | 373 | 5.6 | 4640 | 8.4 | 0.209 |
| 10 | 18.952 | 4.6787 | 130 | 353 | 5.3 | 2792 | 5.1 | 0.133 |
| 11 | 20.848 | 4.2574 | 185 | 220 | 3.3 | 2214 | 4.0 | 0.169 |
| 12 | 21.181 | 4.1911 | 154 | 838 | 12.5 | 9138 | 16.6 | 0.183 |
| 13 | 22.797 | 3.8975 | 185 | 279 | 4.2 | 2289 | 4.2 | 0.138 |
| 14 | 24.056 | 3.6964 | 137 | 148 | 2.2 | 1586 | 2.9 | 0.181 |
| 15 | 25.424 | 3.5005 | 138 | 105 | 1.6 | 1049 | 1.9 | 0.168 |
| 16 | 26.368 | 3.3773 | 153 | 278 | 4.2 | 2187 | 3.8 | 0.127 |
| 17 | 30.328 | 2.9448 | 116 | 141 | 2.1 | 1277 | 2.3 | 0.152 |

Figure 5C

| [C15051812-Ethanol-Wet.raw] | | | | | | | | Peak Search Report |
|---|---|---|---|---|---|---|---|---|
| SCAN: 4.0/39.9779/0.01972/18.6(sec), Cu(40kV,40mA), I(max)=20824, 10/20/17 10:15 | | | | | | | | |
| PEAK: 15-pts/Parabolic Filter, Threshold=5.0, Cutoff=1.0%, BG=3/0.5, Peak-Top=Summit | | | | | | | | |
| NOTE: Intensity = Counts, 2T(0)=0.0(°), Wavelength to Compute d-Spacing = 1.54056A(Cu/K-alpha1) | | | | | | | | |
| # | 2-Theta | d(A) | BG | Height | I% | Area | I% | FWHM |
| 1 | 4.691 | 18.8207 | 549 | 20275 | 100.0 | 127796 | 100.0 | 0.106 |
| 2 | 8.023 | 11.0111 | 219 | 828 | 4.1 | 5103 | 4.0 | 0.103 |
| 3 | 11.144 | 7.9333 | 245 | 10079 | 49.7 | 64524 | 50.5 | 0.107 |
| 4 | 14.020 | 6.3115 | 230 | 2939 | 14.5 | 24638 | 19.3 | 0.141 |
| 5 | 14.335 | 6.1734 | 271 | 887 | 4.4 | 7806 | 6.2 | 0.149 |
| 6 | 15.226 | 5.8141 | 214 | 1333 | 6.6 | 13490 | 10.6 | 0.170 |
| 7 | 16.107 | 5.4981 | 207 | 374 | 1.8 | 2554 | 2.0 | 0.114 |
| 8 | 17.672 | 5.0145 | 198 | 535 | 2.6 | 6253 | 4.9 | 0.196 |
| 9 | 18.915 | 4.6879 | 196 | 992 | 4.9 | 7461 | 5.8 | 0.126 |
| 10 | 20.842 | 4.2584 | 256 | 250 | 1.2 | 3120 | 2.4 | 0.210 |
| 11 | 21.142 | 4.1987 | 213 | 1531 | 7.6 | 17584 | 14.1 | 0.197 |
| 12 | 22.421 | 3.9620 | 184 | 149 | 0.7 | 1579 | 1.2 | 0.177 |
| 13 | 24.037 | 3.6993 | 161 | 325 | 1.6 | 2726 | 2.1 | 0.141 |
| 14 | 30.235 | 2.9535 | 104 | 219 | 1.1 | 2289 | 1.8 | 0.174 |

Figure 5D

| [C15031812-Ethanol-Wet.raw] | | | | | | | | Peak Search Report |
|---|---|---|---|---|---|---|---|---|
| SCAN: 4.0/38.97798,0.01972/18.6(sec), Cu(40kV,40mA), I(max)=20824, 10/20/17 10:15 | | | | | | | | |
| PEAK: 15-pts/Parabolic Filter, Threshold=3.0, Cutoff=1.0%, BG=3/0.5, Peak-Top=Summit | | | | | | | | |
| NOTE: Intensity = Counts, 2T(0)=0.0(°), Wavelength to Compute d-Spacing = 1.54056Å(Cu/K-alpha1) | | | | | | | | |
| # | 2-Theta | d(A) | BG | Height | I% | Area | I% | FWHM |
| 1 | 4.681 | 18.8867 | 549 | 20275 | 100.0 | 127758 | 100.0 | 0.108 |
| 2 | 8.022 | 11.0111 | 219 | 828 | 4.1 | 5162 | 4.0 | 0.103 |
| 3 | 11.144 | 7.9333 | 248 | 10078 | 49.7 | 64624 | 50.6 | 0.107 |
| 4 | 14.026 | 6.3118 | 230 | 2910 | 14.3 | 24638 | 19.3 | 0.141 |
| 5 | 14.338 | 6.1734 | 271 | 887 | 4.4 | 7806 | 6.1 | 0.149 |
| 6 | 15.226 | 5.8141 | 214 | 1333 | 6.6 | 13400 | 10.5 | 0.170 |
| 7 | 16.107 | 5.4981 | 207 | 374 | 1.8 | 2664 | 2.1 | 0.114 |
| 8 | 17.672 | 5.0149 | 198 | 515 | 2.5 | 5251 | 4.1 | 0.166 |
| 9 | 18.315 | 4.8370 | 186 | 910 | 4.5 | 4481 | 3.5 | 0.138 |
| 10 | 20.842 | 4.2584 | 256 | 250 | 1.2 | 3128 | 2.4 | 0.210 |
| 11 | 21.142 | 4.1987 | 213 | 1531 | 7.6 | 17804 | 14.1 | 0.197 |
| 12 | 22.421 | 3.9630 | 184 | 149 | 0.7 | 1575 | 1.2 | 0.177 |
| 13 | 24.637 | 3.6093 | 181 | 335 | 1.6 | 2726 | 2.1 | 0.141 |
| 14 | 30.236 | 2.9538 | 184 | 218 | 1.1 | 2289 | 1.8 | 0.174 |

Figure 5E

| [C15031812-IPA-Dry.raw] | | | | | | | | Peak Search Report |
|---|---|---|---|---|---|---|---|---|
| SCAN: 4.0/38.97798,0.01972/18.6(sec), Cu(40kV,40mA), I(max)=6170, 10/20/17 10:15 | | | | | | | | |
| PEAK: 15-pts/Parabolic Filter, Threshold=3.0, Cutoff=1.0%, BG=3/0.5, Peak-Top=Summit | | | | | | | | |
| NOTE: Intensity = Counts, 2T(0)=0.0(°), Wavelength to Compute d-Spacing = 1.54056Å(Cu/K-alpha1) | | | | | | | | |
| # | 2-Theta | d(A) | BG | Height | I% | Area | I% | FWHM |
| 1 | 4.631 | 19.0646 | 506 | 5664 | 100.0 | 52279 | 100.0 | 0.158 |
| 2 | 7.968 | 11.0813 | 212 | 161 | 2.8 | 1360 | 2.6 | 0.143 |
| 3 | 11.083 | 7.9775 | 168 | 1848 | 32.6 | 15284 | 29.3 | 0.139 |
| 4 | 13.961 | 6.3379 | 145 | 1018 | 18.0 | 8859 | 16.8 | 0.148 |
| 5 | 14.278 | 6.1990 | 166 | 251 | 4.4 | 1835 | 3.5 | 0.122 |
| 6 | 15.184 | 5.8301 | 140 | 674 | 11.9 | 6317 | 12.1 | 0.157 |
| 7 | 17.026 | 5.2037 | 191 | 193 | 3.4 | 1449 | 2.8 | 0.128 |
| 8 | 17.416 | 5.0880 | 134 | 129 | 2.3 | 3299 | 6.3 | 0.429 |
| 9 | 17.630 | 5.0265 | 175 | 387 | 6.8 | 4410 | 8.4 | 0.191 |
| 10 | 18.869 | 4.6991 | 121 | 212 | 3.7 | 2014 | 3.9 | 0.159 |
| 11 | 20.748 | 4.2775 | 175 | 220 | 3.9 | 2514 | 4.8 | 0.192 |
| 12 | 21.100 | 4.2070 | 157 | 604 | 10.7 | 6681 | 12.8 | 0.185 |
| 13 | 22.701 | 3.9138 | 166 | 320 | 5.6 | 2828 | 5.4 | 0.148 |
| 14 | 23.957 | 3.7114 | 137 | 86 | 1.5 | 930 | 1.8 | 0.179 |
| 15 | 25.340 | 3.5119 | 126 | 111 | 2.0 | 1180 | 2.3 | 0.178 |
| 16 | 26.268 | 3.3872 | 135 | 287 | 5.1 | 3129 | 6.0 | 0.183 |
| 17 | 30.158 | 2.9609 | 109 | 94 | 1.7 | 770 | 1.5 | 0.137 |

Figure 5F

| [C15051812-IPA-Wet.raw] | | | | | | | | Peak Search Report |
|---|---|---|---|---|---|---|---|---|
| SCAN: 4.0/39.9779/0.01972/18.6(sec), Cu(40kV,40mA), I(max)=7271, 10/20/17 10:15 | | | | | | | | |
| PEAK: 15-pts/Parabolic Filter, Threshold=5.0, Cutoff=1.0%, BG=3/0.5, Peak-Top=Summit | | | | | | | | |
| NOTE: Intensity = Counts, 2T(0)=0.0(°), Wavelength to Compute d-Spacing = 1.54056Å(Cu/K-alpha1) | | | | | | | | |

| # | 2-Theta | d(A) | BG | Height | I% | Area | I% | FWHM |
|---|---|---|---|---|---|---|---|---|
| 1 | 4.628 | 19.0783 | 477 | 6784 | 100.0 | 52904 | 100.0 | 0.131 |
| 2 | 7.980 | 11.0982 | 212 | 207 | 3.0 | 1449 | 2.7 | 0.117 |
| 3 | 8.749 | 10.0992 | 180 | 107 | 1.6 | 722 | 1.4 | 0.113 |
| 4 | 11.079 | 7.9796 | 194 | 2165 | 31.9 | 15368 | 29.0 | 0.119 |
| 5 | 13.942 | 6.3466 | 185 | 1611 | 23.7 | 11802 | 22.3 | 0.123 |
| 6 | 14.258 | 6.2067 | 182 | 381 | 5.6 | 2271 | 4.3 | 0.100 |
| 7 | 15.165 | 5.8378 | 140 | 903 | 13.3 | 7904 | 14.9 | 0.147 |
| 8 | 17.611 | 5.0318 | 134 | 438 | 6.4 | 4224 | 8.0 | 0.162 |
| 9 | 18.853 | 4.7031 | 121 | 258 | 3.8 | 1878 | 3.5 | 0.122 |
| 10 | 20.785 | 4.2702 | 143 | 184 | 2.7 | 2898 | 5.5 | 0.264 |
| 11 | 21.064 | 4.2142 | 142 | 814 | 12.0 | 9238 | 17.5 | 0.190 |
| 12 | 23.959 | 3.7112 | 109 | 87 | 1.3 | 565 | 1.1 | 0.109 |
| 13 | 25.324 | 3.5141 | 99 | 80 | 1.2 | 916 | 1.7 | 0.192 |
| 14 | 28.831 | 3.0940 | 87 | 72 | 1.1 | 650 | 1.2 | 0.151 |
| 15 | 30.175 | 2.9593 | 74 | 76 | 1.1 | 972 | 1.8 | 0.214 |

Figure 5G

DVS Isotherm Analysis Report

Date: 13 Nov 2015
Time: 7:13 PM
File: G:\Data-2015(PDS)\Preformulation\BPI-20150826\C15051812-DVS\DSC- (
Meth: G:\METHOD\General\method\0-90-0% dmdt0.01 step 10%(10-180min).sao
Sample: DSC-C15051812-blank 1-dry
Temp: 25.1 °C
MRef: 8.1768 from Mass at end of first 0.0 P/Po stage

| | Target | Change In Mass (%) - ref | | |
|---|---|---|---|---|
| | % P/Po | Sorption | Desorption | Hysteresis |
| Cycle 1 | 0.0 | 0.000 | 0.023 | |
| | 10.0 | 0.323 | 0.560 | 0.237 |
| | 20.0 | 2.094 | 3.527 | 1.433 |
| | 30.0 | 3.359 | 3.975 | 0.616 |
| | 40.0 | 3.963 | 4.471 | 0.509 |
| | 50.0 | 4.486 | 4.762 | 0.276 |
| | 60.0 | 4.717 | 4.944 | 0.227 |
| | 70.0 | 4.923 | 5.119 | 0.196 |
| | 80.0 | 5.125 | 5.271 | 0.146 |
| | 90.0 | 5.429 | 5.429 | |

Fig. 9B

| [Salt-C15051812-H2SO4(1-1)-dry.raw] | | | | | | | | Peak Search Report |
|---|---|---|---|---|---|---|---|---|
| SCAN: 4.0/39.9779/0.01972/18.6(sec), Cu(40kV,40mA), I(max)=2770, 10/20/17 10:14 | | | | | | | | |
| PEAK: 15-pts/Parabolic Filter, Threshold=5.0, Cutoff=0.0%, BG=3/0.5, Peak-Top=Summit | | | | | | | | |
| NOTE: Intensity = Counts, 2T(0)=0.0(°), Wavelength to Compute d-Spacing = 1.54056A(Cu/K-alpha1) | | | | | | | | |
| # | 2-Theta | d(A) | BG | Height | I% | Area | I% | FWHM |
| 1 | 4.079 | 21.6440 | 781 | 1989 | 100.0 | 26947 | 100.0 | 0.227 |
| 2 | 4.572 | 19.3112 | 788 | 19 | 1.0 | 38 | 0.1 | 0.100 |
| 3 | 5.479 | 16.1176 | 407 | 127 | 6.4 | 1661 | 6.2 | 0.219 |
| 4 | 9.483 | 9.3188 | 287 | 146 | 7.3 | 3713 | 13.8 | 0.426 |
| 5 | 9.854 | 8.9689 | 304 | 120 | 6.0 | 2704 | 10.0 | 0.378 |
| 6 | 11.953 | 7.3979 | 295 | 62 | 3.1 | 1149 | 4.3 | 0.292 |

Figure 13B

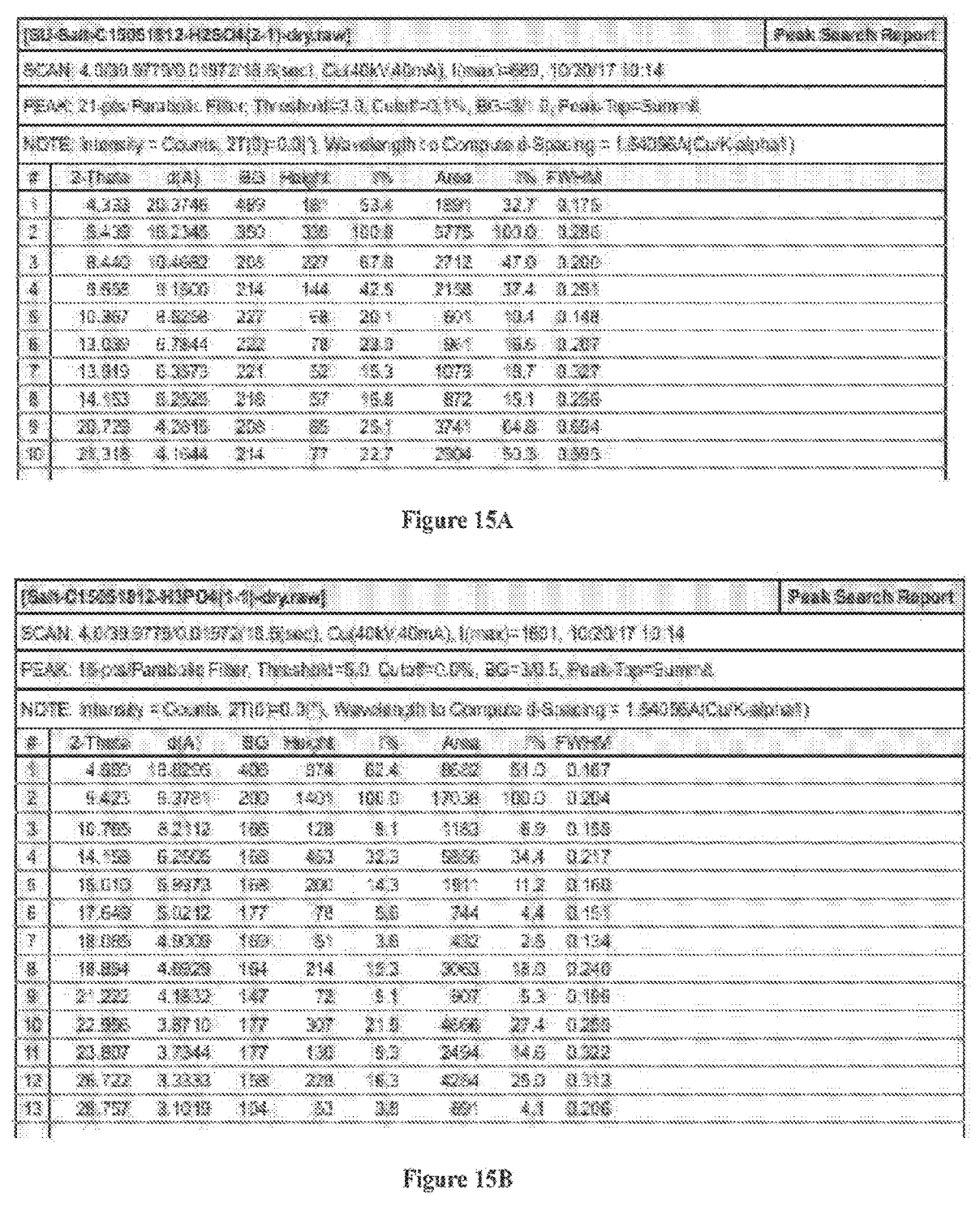

| [SU-Salt-C1505 1812-H2SO4(2-1)-dry.raw] | Peak Search Report |
|---|---|
| SCAN: 4.0/39.9779/0.01972/18.8(sec), Cu(40kV,40mA), I(max)=489, 10/20/17 10:14 | |
| PEAK: 21-pts/Parabolic Filter, Threshold=3.0, Cutoff=0.1%, BG=3/1.0, Peak-Top=Summit | |
| NOTE: Intensity = Counts, 2T(0)=0.0(°), Wavelength to Compute d-Spacing = 1.54056Å(Cu/K-alpha1) | |

| # | 2-Theta | d(A) | BG | Height | I% | Area | I% | FWHM |
|---|---|---|---|---|---|---|---|---|
| 1 | 4.333 | 20.3746 | 489 | 181 | 53.4 | 1891 | 32.7 | 0.176 |
| 2 | 8.438 | 10.2346 | 350 | 338 | 100.0 | 5775 | 100.0 | 0.285 |
| 3 | 8.440 | 10.4682 | 206 | 227 | 67.8 | 2712 | 47.0 | 0.200 |
| 4 | 9.652 | 9.1500 | 214 | 144 | 42.5 | 2158 | 37.4 | 0.251 |
| 5 | 10.367 | 8.5258 | 227 | 68 | 20.1 | 601 | 10.4 | 0.148 |
| 6 | 13.030 | 6.7844 | 222 | 78 | 23.0 | 961 | 16.6 | 0.207 |
| 7 | 13.919 | 6.3573 | 221 | 52 | 15.3 | 1079 | 18.7 | 0.327 |
| 8 | 14.153 | 6.2526 | 218 | 57 | 16.8 | 872 | 15.1 | 0.256 |
| 9 | 20.723 | 4.2818 | 208 | 85 | 25.1 | 3741 | 64.8 | 0.624 |
| 10 | 21.318 | 4.1644 | 214 | 77 | 22.7 | 2904 | 50.3 | 0.565 |

Figure 15A

| [Salt-C1505 1812-H3PO4(1-1)-dry.raw] | Peak Search Report |
|---|---|
| SCAN: 4.0/39.9779/0.01972/18.8(sec), Cu(40kV,40mA), I(max)=1601, 10/20/17 10:14 | |
| PEAK: 15-pts/Parabolic Filter, Threshold=5.0, Cutoff=0.0%, BG=3/0.5, Peak-Top=Summit | |
| NOTE: Intensity = Counts, 2T(0)=0.0(°), Wavelength to Compute d-Spacing = 1.54056Å(Cu/K-alpha1) | |

| # | 2-Theta | d(A) | BG | Height | I% | Area | I% | FWHM |
|---|---|---|---|---|---|---|---|---|
| 1 | 4.850 | 18.8206 | 408 | 974 | 62.4 | 8682 | 51.0 | 0.167 |
| 2 | 9.423 | 9.3781 | 200 | 1401 | 100.0 | 17038 | 100.0 | 0.204 |
| 3 | 10.765 | 8.2112 | 165 | 128 | 8.1 | 1153 | 6.9 | 0.158 |
| 4 | 14.159 | 6.2505 | 168 | 463 | 32.3 | 5856 | 34.4 | 0.217 |
| 5 | 16.010 | 5.5973 | 168 | 200 | 14.3 | 1911 | 11.2 | 0.160 |
| 6 | 17.648 | 5.0212 | 177 | 78 | 5.6 | 744 | 4.4 | 0.151 |
| 7 | 18.085 | 4.9009 | 169 | 51 | 3.6 | 432 | 2.5 | 0.134 |
| 8 | 18.894 | 4.6928 | 194 | 214 | 13.3 | 3063 | 18.0 | 0.240 |
| 9 | 21.222 | 4.1832 | 147 | 72 | 5.1 | 907 | 5.3 | 0.198 |
| 10 | 22.956 | 3.8710 | 177 | 307 | 21.9 | 4656 | 27.4 | 0.253 |
| 11 | 23.807 | 3.7344 | 177 | 130 | 9.3 | 2494 | 14.6 | 0.322 |
| 12 | 26.722 | 3.3333 | 158 | 228 | 16.3 | 4254 | 25.0 | 0.313 |
| 13 | 28.757 | 3.1019 | 134 | 53 | 3.8 | 691 | 4.1 | 0.206 |

Figure 15B

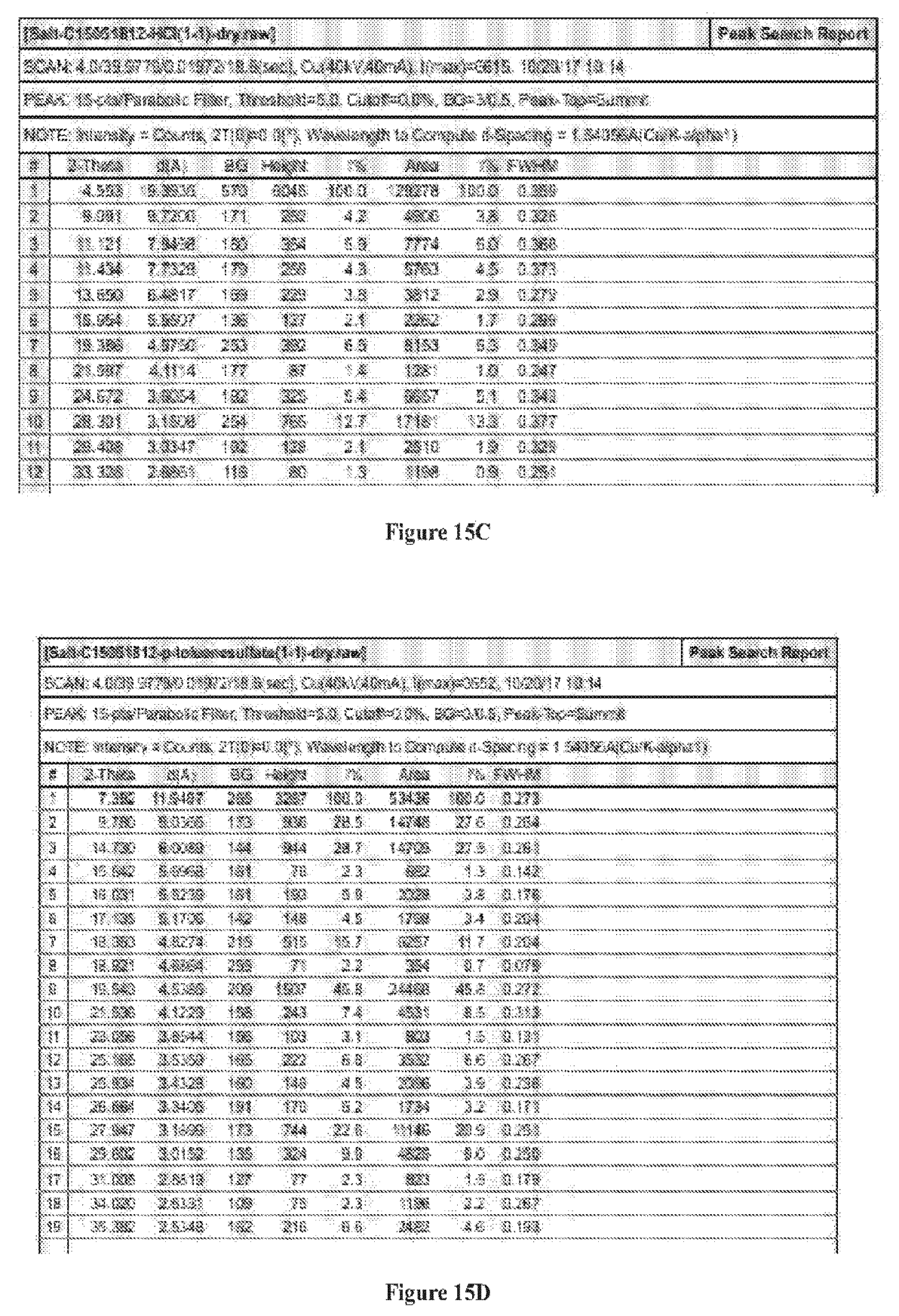

[Salt-C15551812-HCl(1-1)-dry.raw] — Peak Search Report

SCAN: 4.0/39.9779/0.01972/18.8(sec), Cu(40kV,40mA), I(max)=6615, 10/20/17 13:14

PEAK: 15-pts/Parabolic Filter, Threshold=3.0, Cutoff=0.0%, BG=3/0.5, Peak-Top=Summit NOTE: Intensity = Counts, 2T(0)=0.0(°), Wavelength to Compute d-Spacing = 1.54056A(Cu/K-alpha1)

| # | 2-Theta | d(A) | BG | Height | I% | Area | I% | FWHM |
|---|---|---|---|---|---|---|---|---|
| 1 | 4.553 | 19.3936 | 573 | 6045 | 100.0 | 129278 | 100.0 | 0.289 |
| 2 | 9.081 | 9.7300 | 171 | 255 | 4.2 | 4800 | 3.8 | 0.328 |
| 3 | 11.121 | 7.9498 | 180 | 354 | 5.9 | 7774 | 6.0 | 0.368 |
| 4 | 11.434 | 7.7328 | 179 | 259 | 4.3 | 5763 | 4.5 | 0.373 |
| 5 | 13.690 | 6.4617 | 169 | 229 | 3.8 | 3812 | 2.9 | 0.279 |
| 6 | 15.954 | 5.5507 | 136 | 127 | 2.1 | 2262 | 1.7 | 0.289 |
| 7 | 18.386 | 4.8750 | 253 | 392 | 6.5 | 8153 | 6.3 | 0.349 |
| 8 | 21.587 | 4.1114 | 177 | 87 | 1.4 | 1281 | 1.0 | 0.247 |
| 9 | 24.572 | 3.6254 | 182 | 325 | 5.4 | 6657 | 5.1 | 0.343 |
| 10 | 28.201 | 3.1626 | 254 | 765 | 12.7 | 17181 | 13.3 | 0.377 |
| 11 | 29.409 | 3.0347 | 182 | 129 | 2.1 | 2510 | 1.9 | 0.329 |
| 12 | 33.326 | 2.6861 | 118 | 80 | 1.3 | 1198 | 0.9 | 0.251 |

Figure 15C

[Salt-C15551812-p-toluenesulfonate(1-1)-dry.raw] — Peak Search Report

SCAN: 4.0/39.9779/0.01972/18.8(sec), Cu(40kV,40mA), I(max)=3552, 10/20/17 13:14

PEAK: 15-pts/Parabolic Filter, Threshold=3.0, Cutoff=0.0%, BG=3/0.5, Peak-Top=Summit NOTE: Intensity = Counts, 2T(0)=0.0(°), Wavelength to Compute d-Spacing = 1.54056A(Cu/K-alpha1)

| # | 2-Theta | d(A) | BG | Height | I% | Area | I% | FWHM |
|---|---|---|---|---|---|---|---|---|
| 1 | 7.382 | 11.9487 | 265 | 3287 | 100.0 | 53436 | 100.0 | 0.273 |
| 2 | 9.780 | 9.0365 | 173 | 936 | 28.5 | 14748 | 27.6 | 0.264 |
| 3 | 14.730 | 6.0093 | 144 | 944 | 28.7 | 14728 | 27.6 | 0.261 |
| 4 | 15.942 | 5.5549 | 161 | 76 | 2.3 | 682 | 1.3 | 0.142 |
| 5 | 16.031 | 5.5239 | 161 | 193 | 5.9 | 2028 | 3.8 | 0.176 |
| 6 | 17.135 | 5.1706 | 142 | 148 | 4.5 | 1798 | 3.4 | 0.204 |
| 7 | 18.363 | 4.8274 | 215 | 515 | 15.7 | 6267 | 11.7 | 0.204 |
| 8 | 18.921 | 4.6864 | 256 | 71 | 2.2 | 364 | 0.7 | 0.079 |
| 9 | 19.543 | 4.5385 | 206 | 1507 | 45.8 | 24460 | 45.8 | 0.272 |
| 10 | 21.536 | 4.1229 | 198 | 243 | 7.4 | 4581 | 8.5 | 0.313 |
| 11 | 23.066 | 3.8544 | 156 | 103 | 3.1 | 803 | 1.5 | 0.131 |
| 12 | 25.385 | 3.5059 | 165 | 222 | 6.8 | 3532 | 6.6 | 0.267 |
| 13 | 25.934 | 3.4328 | 160 | 148 | 4.5 | 2086 | 3.9 | 0.238 |
| 14 | 26.664 | 3.3405 | 191 | 170 | 5.2 | 1734 | 3.2 | 0.171 |
| 15 | 27.947 | 3.1899 | 173 | 744 | 22.6 | 11146 | 20.9 | 0.253 |
| 16 | 29.602 | 3.0152 | 135 | 324 | 9.9 | 4826 | 9.0 | 0.250 |
| 17 | 31.008 | 2.8819 | 127 | 77 | 2.3 | 803 | 1.5 | 0.179 |
| 18 | 34.020 | 2.6331 | 109 | 75 | 2.3 | 1196 | 2.2 | 0.267 |
| 19 | 35.382 | 2.5348 | 162 | 216 | 6.6 | 2463 | 4.6 | 0.193 |

Figure 15D

DVS Isotherm Analysis Report

Date: 16 Nov 2015
Time: 5:56 PM
File: G:\Data-2015(PDS)\Preformulation\BPI-20150826\C15051812-DVS\DSC-
Meth: G:\METHOD\General\method\0-90-0% dmdt0.01 step 10%(10-180min).sao
Sample: DSC-C15051812-HCl(1-1)-dry
Temp: 25.2 °C
MRef: 11.3845 from Mass at end of first 0.0 P/Po stage

| | Target | Change In Mass (%) - ref | | |
|---|---|---|---|---|
| | % P/Po | Sorption | Desorption | Hysteresis |
| Cycle 1 | 0.0 | -0.001 | 0.021 | |
| | 10.0 | 0.222 | 0.248 | 0.027 |
| | 20.0 | 0.466 | 0.935 | 0.469 |
| | 30.0 | 3.302 | 3.303 | 0.001 |
| | 40.0 | 3.410 | 3.426 | 0.016 |
| | 50.0 | 3.479 | 3.507 | 0.027 |
| | 60.0 | 3.530 | 3.569 | 0.038 |
| | 70.0 | 3.595 | 3.616 | 0.021 |
| | 80.0 | 3.644 | 3.683 | 0.039 |
| | 90.0 | 3.759 | 3.759 | |

Fig. 17B

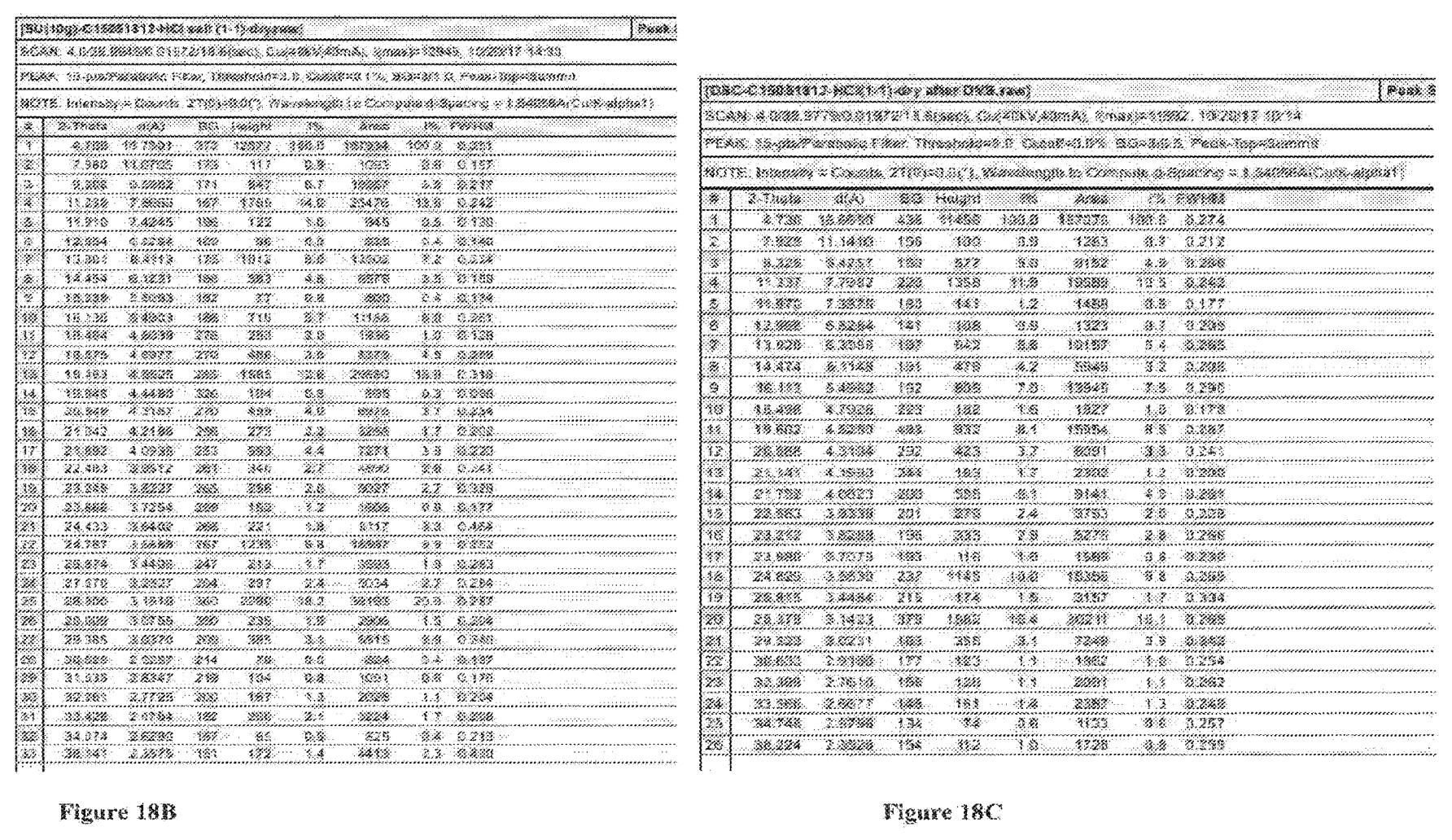

[SU]10g)-C15881312-HCl salt (1-1)-dry.raw] Peak

SCAN: 4.0/38.99/0.01572/18.6(sec), Cu(40kV,40mA), I(max)=12845, 10/20/17 14:33

PEAK: 15-pts/Parabolic Filter, Threshold=2.0, Cutoff=0.1%, BG=3/1.0, Peak-Top=Summit NOTE: Intensity = Counts, 2T(0)=0.0(°), Wavelength to Compute d-Spacing = 1.54059Å(Cu/K-alpha1)

| # | 2-Theta | d(A) | BG | Height | I% | Area | I% | FWHM |
|---|---|---|---|---|---|---|---|---|
| 1 | 4.708 | 18.7531 | 372 | 12577 | 100.0 | 187334 | 100.0 | 0.251 |
| 2 | 7.960 | 11.0725 | 173 | 117 | 0.9 | 1082 | 0.6 | 0.157 |
| 3 | 9.388 | 9.4062 | 171 | 847 | 6.7 | 10867 | 5.8 | 0.217 |
| 4 | 11.238 | 7.8655 | 167 | 1769 | 14.0 | 23476 | 12.5 | 0.242 |
| 5 | 11.910 | 7.4245 | 186 | 122 | 1.0 | 945 | 0.5 | 0.130 |
| 6 | 12.654 | 6.9894 | 180 | 86 | 0.8 | 888 | 0.4 | 0.140 |
| 7 | 13.304 | 6.6113 | 178 | 1012 | 8.0 | 13502 | 7.2 | 0.224 |
| 8 | 14.454 | 6.1221 | 198 | 583 | 4.6 | 6276 | 3.3 | 0.159 |
| 9 | 15.238 | 5.8083 | 182 | 77 | 0.6 | 883 | 0.4 | 0.194 |
| 10 | 16.126 | 5.4903 | 188 | 715 | 5.7 | 11166 | 6.0 | 0.261 |
| 11 | 18.464 | 4.8039 | 278 | 253 | 2.0 | 1896 | 1.0 | 0.128 |
| 12 | 18.876 | 4.6977 | 270 | 486 | 3.6 | 8372 | 4.5 | 0.289 |
| 13 | 19.353 | 4.5825 | 288 | 1585 | 12.6 | 20680 | 15.9 | 0.338 |
| 14 | 19.948 | 4.4480 | 326 | 184 | 0.9 | 398 | 0.2 | 0.088 |
| 15 | 20.949 | 4.2367 | 270 | 492 | 4.0 | 6974 | 3.7 | 0.234 |
| 16 | 21.042 | 4.2186 | 298 | 273 | 2.2 | 3268 | 1.7 | 0.202 |
| 17 | 21.892 | 4.0938 | 253 | 563 | 4.4 | 7371 | 3.9 | 0.228 |
| 18 | 22.403 | 3.9512 | 261 | 346 | 2.7 | 4890 | 2.6 | 0.241 |
| 19 | 23.388 | 3.8227 | 265 | 256 | 2.0 | 5037 | 2.7 | 0.329 |
| 20 | 23.868 | 3.7254 | 220 | 152 | 1.2 | 1656 | 0.9 | 0.177 |
| 21 | 24.433 | 3.6402 | 266 | 221 | 1.8 | 6117 | 3.3 | 0.468 |
| 22 | 24.787 | 3.5888 | 257 | 1238 | 9.8 | 16887 | 8.9 | 0.232 |
| 23 | 25.874 | 3.4406 | 247 | 213 | 1.7 | 3683 | 1.9 | 0.283 |
| 24 | 27.070 | 3.2927 | 204 | 297 | 2.4 | 5034 | 2.7 | 0.294 |
| 25 | 28.500 | 3.1918 | 260 | 2280 | 18.2 | 38183 | 20.6 | 0.287 |
| 26 | 29.088 | 3.0759 | 260 | 235 | 1.9 | 2806 | 1.5 | 0.204 |
| 27 | 29.385 | 3.0370 | 208 | 385 | 3.1 | 6615 | 3.4 | 0.360 |
| 28 | 30.889 | 2.9287 | 214 | 78 | 0.6 | 884 | 0.4 | 0.187 |
| 29 | 31.535 | 2.8347 | 219 | 134 | 0.8 | 1001 | 0.6 | 0.176 |
| 30 | 32.361 | 2.7725 | 250 | 167 | 1.3 | 2086 | 1.1 | 0.208 |
| 31 | 33.428 | 2.6784 | 182 | 288 | 2.1 | 3224 | 1.7 | 0.208 |
| 32 | 34.074 | 2.6290 | 167 | 65 | 0.5 | 825 | 0.4 | 0.213 |
| 33 | 35.341 | 2.5376 | 161 | 172 | 1.4 | 4413 | 2.3 | 0.433 |

Figure 18B

[DSC-C15881312-HCl(1-1)-dry after DVS.raw] Peak S

SCAN: 4.0/38.977/0.01972/13.8(sec), Cu(40kV,40mA), I(max)=11552, 10/20/17 10:14

PEAK: 15-pts/Parabolic Filter, Threshold=3.0, Cutoff=0.1%, BG=3/1.0, Peak-Top=Summit NOTE: Intensity = Counts, 2T(0)=0.0(°), Wavelength to Compute d-Spacing = 1.54059Å(Cu/K-alpha1)

| # | 2-Theta | d(A) | BG | Height | I% | Area | I% | FWHM |
|---|---|---|---|---|---|---|---|---|
| 1 | 4.738 | 18.6359 | 436 | 11458 | 100.0 | 187076 | 100.0 | 0.274 |
| 2 | 7.928 | 11.1430 | 156 | 100 | 0.9 | 1263 | 0.7 | 0.212 |
| 3 | 9.226 | 9.4257 | 180 | 577 | 5.0 | 9152 | 4.9 | 0.286 |
| 4 | 11.337 | 7.7987 | 220 | 1358 | 11.9 | 19588 | 10.5 | 0.242 |
| 5 | 11.870 | 7.3838 | 183 | 141 | 1.2 | 1458 | 0.8 | 0.177 |
| 6 | 12.666 | 6.9264 | 141 | 108 | 0.9 | 1323 | 0.7 | 0.209 |
| 7 | 13.028 | 6.3058 | 197 | 642 | 5.6 | 10157 | 5.4 | 0.265 |
| 8 | 14.474 | 6.1148 | 191 | 479 | 4.2 | 5945 | 3.2 | 0.208 |
| 9 | 16.182 | 5.4682 | 192 | 805 | 7.0 | 13945 | 7.5 | 0.290 |
| 10 | 18.498 | 4.7926 | 223 | 182 | 1.6 | 1827 | 1.0 | 0.178 |
| 11 | 19.603 | 4.5250 | 483 | 932 | 8.1 | 15954 | 8.5 | 0.287 |
| 12 | 20.668 | 4.3134 | 292 | 423 | 3.7 | 6291 | 3.3 | 0.241 |
| 13 | 21.141 | 4.1993 | 366 | 193 | 1.7 | 2308 | 1.2 | 0.206 |
| 14 | 21.792 | 4.0023 | 280 | 588 | 5.1 | 9141 | 4.9 | 0.264 |
| 15 | 22.863 | 3.8938 | 201 | 273 | 2.4 | 3753 | 2.0 | 0.228 |
| 16 | 23.242 | 3.8238 | 196 | 333 | 2.9 | 5278 | 2.8 | 0.266 |
| 17 | 23.088 | 3.7075 | 183 | 118 | 1.0 | 1588 | 0.8 | 0.230 |
| 18 | 24.625 | 3.6530 | 232 | 1145 | 10.0 | 18356 | 9.8 | 0.269 |
| 19 | 26.815 | 3.4464 | 215 | 174 | 1.5 | 3157 | 1.7 | 0.304 |
| 20 | 28.378 | 3.1423 | 378 | 1862 | 16.4 | 30211 | 16.1 | 0.268 |
| 21 | 29.523 | 3.0231 | 183 | 355 | 3.1 | 7249 | 3.9 | 0.342 |
| 22 | 30.653 | 2.9188 | 177 | 123 | 1.1 | 1862 | 1.0 | 0.254 |
| 23 | 32.360 | 2.7616 | 158 | 128 | 1.1 | 2001 | 1.1 | 0.262 |
| 24 | 33.395 | 2.6877 | 186 | 161 | 1.4 | 2387 | 1.3 | 0.248 |
| 25 | 34.748 | 2.5798 | 134 | 74 | 0.6 | 1133 | 0.6 | 0.257 |
| 26 | 38.224 | 2.3526 | 154 | 112 | 1.0 | 1728 | 0.9 | 0.259 |

Figure 18C

DVS Isotherm Analysis Report

Date: 13 Nov 2015
Time: 5:13 PM
File: G:\Data-2015(PDS)\Preformulation\BPI-20150826\C15051812-DVS\DSC- (
Meth: G:\METHOD\General\method\0-90-0% dmdt0.01 step 10%(10-180min).sao
Sample: DSC-C15051812-H2SO4(1-1)-dry
Temp: 25.5 °C
MRef: 12.2138 from Mass at end of first 0.0 P/Po stage

| | Target | Change In Mass (%) - ref | | |
|---|---|---|---|---|
| | % P/Po | Sorption | Desorption | Hysteresis |
| Cycle 1 | 0.0 | 0.01 | 1.06 | |
| | 10.0 | 3.09 | 4.92 | 1.83 |
| | 20.0 | 5.74 | 8.21 | 2.47 |
| | 30.0 | 7.84 | 11.01 | 3.17 |
| | 40.0 | 9.40 | 13.57 | 4.17 |
| | 50.0 | 11.40 | 16.17 | 4.77 |
| | 60.0 | 13.99 | 18.80 | 4.81 |
| | 70.0 | 18.88 | 22.79 | 3.91 |
| | 80.0 | 26.42 | 28.78 | 2.36 |
| | 90.0 | 39.29 | 39.29 | |

Fig. 21B

DVS Isotherm Analysis Report

Date: 20 Nov 2015
Time: 6:57 PM
File: G:\Data-2015(PDS)\Preformulation\BPI-20150826\C15051812-DVS\DSC- (
Meth: G:\METHOD\General\method\0-90-0% dmdt0.01 step 10%(10-180min).sao
Sample: DSC-C15051812-H3PO4(1-1)-dry
Temp: 25.3 °C
MRef: 13.6291 from Mass at end of first 0.0 P/Po stage

| | Target % P/Po | Change In Mass (%) - ref Sorption | Desorption | Hysteresis |
|---|---|---|---|---|
| Cycle 1 | 0.0 | 0.000 | 0.079 | |
| | 10.0 | 0.421 | 0.550 | 0.128 |
| | 20.0 | 0.792 | 0.976 | 0.184 |
| | 30.0 | 1.145 | 1.445 | 0.300 |
| | 40.0 | 1.472 | 1.904 | 0.432 |
| | 50.0 | 1.813 | 2.281 | 0.469 |
| | 60.0 | 2.147 | 2.640 | 0.493 |
| | 70.0 | 2.534 | 3.131 | 0.597 |
| | 80.0 | 3.158 | 3.794 | 0.636 |
| | 90.0 | 4.854 | 4.854 | |

Fig. 24B

DVS Isotherm Analysis Report

Date: 20 Nov 2015
Time: 6:56 PM
File: G:\Data-2015(PDS)\Preformulation\BPI-20150826\C15051812-DVS\DSC- (
Meth: G:\METHOD\General\method\0-90-0% DMDT0.01 step 10%
Sample: DSC-C15051812-p-toluenesulfate(1-1)-dry
Temp: 25.2 °C
MRef: 12.425 from Mass at end of first 0.0 P/Po stage

| | Target % P/Po | Change In Mass (%) - ref Sorption | Desorption | Hysteresis |
|---|---|---|---|---|
| Cycle 1 | 0.0 | 0.000 | 0.026 | |
| | 10.0 | 0.222 | 0.297 | 0.075 |
| | 20.0 | 0.450 | 0.552 | 0.102 |
| | 30.0 | 0.669 | 0.780 | 0.111 |
| | 40.0 | 0.897 | 0.998 | 0.101 |
| | 50.0 | 1.115 | 1.235 | 0.120 |
| | 60.0 | 1.300 | 1.431 | 0.131 |
| | 70.0 | 1.491 | 1.659 | 0.168 |
| | 80.0 | 1.665 | 1.900 | 0.235 |
| | 90.0 | 2.134 | 2.134 | |

Fig. 27B

CRYSTALLINE AND AMORPHOUS FORMS OF N-(5-((4-ETHYLPIPERAZIN-1-YL) METHYL)PYRIDINE-2-YL)-5-FLUORO-4-(3-ISOPROPYL-2-METHYL-2H-INDAZOL-5-YL)PYRIMIDIN-2-AMINE AND ITS SALTS, AND PREPARATION METHODS AND THERAPEUTIC USES THEREOF

CROSS-REFERENCE TO RELATED APPLICATIONS

This application is a National Stage application of PCT/US2020/023828, filed Mar. 20, 2020, which claims the benefit of U.S. Provisional Application No. 62/821,141, filed Mar. 20, 2019, both of which are incorporated by reference herein in their entirety.

FIELD OF THE INVENTION

The present invention relates to crystalline and amorphous forms of N-(5-((4-ethylpiperazin-1-yl)methyl)pyridine-2-yl)-5-fluoro-4-(3-isopropyl-2-methyl-2H-indazol-5-yl)pyrimidin-2-amine and pharmaceutically acceptable salts, and use thereof in the treatment or prevention of diseases or medical conditions mediated through certain cyclin-dependent kinases (CDKs), such as various cancers.

BACKGROUND OF THE INVENTION

Cyclin-dependent kinases (CDKs) are a family of protein kinases that regulate cell division and proliferation. Cell cycle progression is controlled by cyclins and their associated cyclin-dependent kinases, such as CDK1-CDK4 and CDK6, while other CDKs such as CDK7-CDK9 are critical to transcription. CDK binding to cyclins forms heterodimeric complexes that phosphorylate their substrates on serine and threonine residues, which in turn initiates events required for cell-cycle transcription and progression (Malumbres et al. *Trends Biochem. Sci.* 2005, 30, 630-641). Since uncontrolled cell proliferation is a hallmark of cancer, and most cancer cells exhibit deregulation of CDKs, inhibition of CDKs has emerged as a potential treatment for various cancers. While inhibitors with varying degrees of selectivity for CDKs have been reported, selective CDK4/6 inhibitors are currently viewed as a promising class of potential cancer therapeutic agents due to the critical role of CDK4/6 in regulating cell proliferation and the toxic effects associated with inhibition of other CDKs. Compound 1, namely N-(5-((4-ethylpiperazin-1-yl)methyl)pyridin-2-yl-5-fluoro-4-(3-isopropyl-2-methyl-2H-indazol-5-yl)pyrimidin-2-amine, is a potent, selective inhibitor of CDK4/6 useful in the treatment or prevention of diseases, disorders, or medical conditions mediated through certain CDKs, in particular CDK4 and CDK6, such as various types of cancers and inflammation-related conditions. See WO 2016/014904 A1 and U.S. Pat. No. 9,878,994, which are hereby incorporated by reference in their entireties.

1

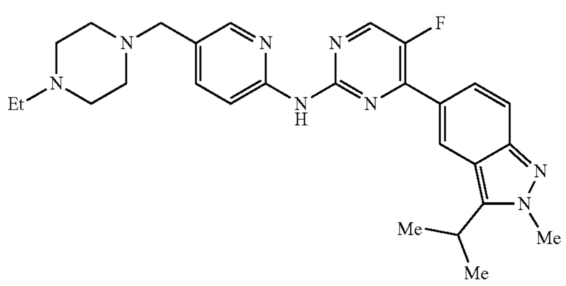

However, to develop Compound 1 into a viable therapeutic agent, there remains a need to identify a suitable solid-state form that may exhibit desirable chemical and physical properties.

It would also be essential to develop reliable and reproducible methods for the manufacture and purification of Compound 1 to the development of suitable formulations. Yet, finding a suitable salt and/or crystalline form for preparing formulation of a drug product that possesses suitable physical and biological properties, including but not limited to solubility, stability, melting point, bioavailability, etc., is often not entirely predictable. The present invention aims to meeting such needs.

SUMMARY OF THE INVENTION

The present invention provides various solid-state forms of the compound of formula 1 (Compound 1) in freebase or salt forms, including amorphous forms and crystalline polymorphs, and methods of preparing them. The present application discloses physical form data for the characterization of Compound 1 and its various pharmaceutical salt forms and polymorphs.

In one aspect, the present invention provides a solid-state form of Compound 1 as a freebase:

1

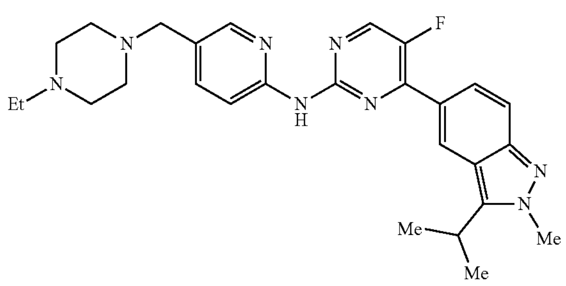

The freebase of Compound 1 exists in one or more crystalline forms, designated as crystal Form A, Form B, Form C, Form D, Form E, and Form F, respectively.

In other aspects, the present invention provides pharmaceutically acceptable salts of Compound 1, comprising Compound 1 and an acid, wherein the acid includes, but is not limited to, HCl, $H_2SO_4$, $H_3PO_4$, methanesulfonic acid, and p-toluenesulfonic acid. Any of the salts may exist in amorphous or various crystalline forms.

In one aspect, the present invention provides the hydrochloric acid salt of N-(5-((4-ethylpiperazin-yl)methyl)pyridin-2-yl-5-fluoro-4-(3-isopropyl-2-methyl-2H-indazol-5-yl)

pyrimidin-2-amine, in which the Compound 1 and hydrochloride are in about 1:1 molar ratio.

In another aspect, the present invention provides a sulfuric acid salt of N-(5-((4-ethylpiperazin-yl)methyl)pyridin-2-yl-5-fluoro-4-(3-isopropyl-2-methyl-2H-indazol-5-yl)pyrimidin-2-amine.

In one embodiment, the sulfuric acid salt comprises N-(5-((4-ethylpiperazin-yl)methyl)pyridin-2-yl-5-fluoro-4-(3-isopropyl-2-methyl-2H-indazol-5-yl)pyrimidin-2-amine and sulfuric acid in about 1:1 molar ratio.

In another embodiment, the sulfuric acid salt comprises N-(5-((4-ethylpiperazin-yl)methyl)pyridin-2-yl-5-fluoro-4-(3-isopropyl-2-methyl-2H-indazol-5-yl)pyrimidin-2-amine and sulfuric acid in about 2:1 molar ratio.

In some embodiments, the sulfuric acid salt, in either about 1:1 or about 2:1 molar ratio, exists in solid amorphous forms.

In some embodiments, the sulfuric acid salt, in either about 1:1 or about 2:1 molar ratio, exists in various crystalline forms (polymorphs).

In another aspect, the present invention provides a phosphoric acid salt of N-(5-((4-ethylpiperazin-yl)methyl)pyridin-2-yl-5-fluoro-4-(3-isopropyl-2-methyl-2H-indazol-5-yl)pyrimidin-2-amine.

In one embodiment, the phosphoric acid salt comprises N-(5-((4-ethylpiperazin-yl)methyl)pyridin-2-yl-5-fluoro-4-(3-isopropyl-2-methyl-2H-indazol-5-yl)pyrimidin-2-amine and phosphoric acid in about 1:1 molar ratio.

In another aspect, the present invention provides a toluenesulfonic acid (tosylate) salt of N-(5-((4-ethylpiperazin-yl)methyl)pyridin-2-yl-5-fluoro-4-(3-isopropyl-2-methyl-2H-indazol-5-yl)pyrimidin-2-amine.

In one embodiment, the tosylate salt comprises toluenesulfonic acid and N-(5-((4-ethylpiperazin-yl)methyl)pyridin-2-yl-5-fluoro-4-(3-isopropyl-2-methyl-2H-indazol-5-yl)pyrimidin-2-amine in about 1:1 molar ratio.

In another aspect, the present invention provides a methanesulfonic acid (mesylate) salt of N-(5-((4-ethylpiperazin-yl)methyl)pyridin-2-yl-5-fluoro-4-(3-isopropyl-2-methyl-2H-indazol-5-yl)pyrimidin-2-amine.

In one embodiment, the mesylate salt comprises N-(5-((4-ethylpiperazin-yl)methyl)pyridin-2-yl-5-fluoro-4-(3-isopropyl-2-methyl-2H-indazol-5-yl)pyrimidin-2-amine and methanesulfonic acid in about 1:2 molar ratio.

In another embodiment, the mesylate salt comprises N-(5-((4-ethylpiperazin-yl)methyl)pyridin-2-yl-5-fluoro-4-(3-isopropyl-2-methyl-2H-indazol-5-yl)pyrimidin-2-amine and methanesulfonic acid in about 1:1 molar ratio.

In some embodiments, the mesylate salt, in either about 1:1 or about 2:1 molar ratio, exists in solid amorphous forms.

In some embodiments, the mesylate salt, in either about 1:1 or about 2:1 molar ratio, exists in various crystalline forms (polymorphs).

In another aspect, the present invention provides methods of preparing solid amorphous forms of Compound 1 and salts thereof, in particular the HCl, $H_2SO_4$, $H_3PO_4$, methanesulfonic acid, and p-toluenesulfonic acid salts disclosed herein.

In another aspect, the present invention provides methods of preparing crystalline forms of Compound 1 and salts thereof, in particular the HCl, $H_2SO_4$, $H_3PO_4$, methanesulfonic acid, and p-toluenesulfonic acid salts disclosed herein.

In another aspect, the present invention provides pharmaceutical compositions comprising any of the amorphous form of Compound 1 or a salt thereof and a pharmaceutically acceptable carrier.

In another aspect, the present invention provides a pharmaceutical composition comprising a crystalline form of Compound 1 or a salt thereof and a pharmaceutically acceptable carrier.

In another aspect, the present invention provides a method of inhibiting a cyclin-dependent kinase (CDK) in a biological sample or in a subject by using an amorphous or crystalline form of of Compound 1 or a salt thereof.

In another aspect, the present invention provides a method of treating or preventing a disease or disorder in a subject associated with a CDK activity, comprising administering to the subject a pharmaceutical composition comprising an amorphous or crystalline form of Compound 1, and a pharmaceutical acceptable carrier.

In another aspect, the present invention provides a method of treating or preventing a disease or disorder in a subject associated with a CDK activity, comprising administering to the subject a pharmaceutical composition comprising an amorphous or crystalline form of a pharmaceutical salt of Compound 1, and a pharmaceutical acceptable carrier.

In any of the above aspects or embodiments, the pharmaceutical salt is preferably selected from the group consisting of HCl, $H_2SO_4$, $H_3PO_4$, methanesulfonic acid, and p-toluenesulfonic acid salts.

In some preferred embodiments, the crystalline forms of pharmaceutically acceptable salts of Compound 1 include, but are not limited to, Crystalline Form A, Crystalline Form B, Crystalline Form C, Crystalline Form D, or Crystalline Form E of the compound of Formula 1 or salts thereof, where applicable.

The disease or disorder associated with CDKs, that can be treated according to the present invention includes, but is not limited to, brain cancer, metastatic brain cancer, squamous cell cancer, bladder cancer, gastric cancer, pancreatic cancer, hepatic cancer, glioblastoma multiforme breast cancer, head cancer, neck cancer, esophageal cancer, prostate cancer, colorectal cancer, lung cancer, renal cancer, kidney cancer, ovarian cancer, gynecological cancer, thyroid cancer, non-small cell lung cancer (NSCLC), refractory ovarian cancer, or head and neck cancer. In one embodiment, the cyclin-dependent kinase (CDK) is CDK4 or CDK6.

Other aspects and benefits of the present invention will be better appreciated in view of the following detailed description, drawings, and claims.

BRIEF DESCRIPTION OF THE DRAWINGS

FIGS. 2A and 2B show X-ray powder diffraction patterns (A) of the freebase of the Compound 1 (Form A); and (B) peak printout.

FIGS. 5A, 5B, 5C, 5D, 5E, 5F and 5G show the peak lists corresponding to the X-ray powder diffraction patterns of the freebase polymorphs of the compound of Formula 1 shown in FIG. 4. Panels A-B correspond to Form C of Compound 1, and panels C-G correspond to Form B of Compound 1.

FIG. 9A and 9B show Dynamic vapor sorption (DVS) isotherm analysis of the freebase of Compound 1 (Form D).

FIGS. 13A and 13B show (A) the X-ray powder diffraction patterns (dry samples) and (B) the peak printout for 50 mg scale Compound 1-$H_2SO_4$ (1:1; Form A).

FIGS. 15A, 15B, 15C, and 15D show the peak printouts for of the 500 mg scale salt screen (freebase:acid) for Compound 1 (dry samples) shown in FIG. 14: (A) $H_2SO_4$ (2:1; Form A) salt, (B) $H_3PO_4$ (1:1; Form A) salt, (C) HCl (1:1; Form A) salt, (D) p-toluenesulfonic acid (1:1; Form A) salt.

FIG. 17A and 17B show the DVS isotherm analysis of Compound 1 •HCl (1:1; Form A).

FIGS. 18A, 18B and 18C show (A) X-ray powder diffraction patterns of Compound 1 •HCl (1:1; Form A) before and after DVS. (B) Peak printout before DVS. (C) Peak printout after DVS.

FIG. 21A and 21B show the DVS isotherm analysis of Compound 1 •$H_2SO$ (1:1; Form A) from the 50 mg scale.

FIG. 27A and 27B show DVS isotherm analysis of Compound 1 •p-toluenesulfonic acid (1:1; Form A)

DETAILED DESCRIPTION OF THE INVENTION

In one aspect, the present invention provides Compound 1 freebase in various solid-state forms:

1

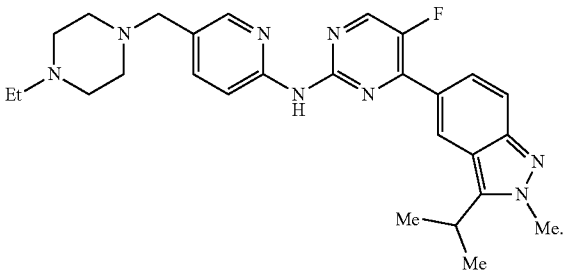

The freebase of Compound 1 exists in one or more crystalline forms, designated as crystalline Form A, Form B, Form C, and Form D, respectively.

In one embodiment, the present invention provides a crystalline form of Compound 1 freebase (Form A) that exhibits an X-ray powder diffraction pattern comprising characteristic peaks at diffraction angles 2θ of approximately 5.9°, 11.9°, and 25.6°, each ±0.2°.

In one embodiment, the X-ray powder diffraction pattern of the Compound 1 freebase in crystalline Form A comprises characteristic peaks, expressed in terms of the interplanar distance, at 14.9 A, 7.5 A, and 3.5 A.

In one embodiment, the X-ray powder diffraction pattern of the Compound 1 freebase in crystalline Form A comprises characteristic peaks at diffraction angles 2θ of approximately 5.6°, 5.9°, 11.9°, 16.5°, 25.6° and 26.2°, each ±0.2°.

In one embodiment, the X-ray powder diffraction pattern of the Compound 1 freebase in crystalline Form A comprises characteristic peaks, expressed in terms of the interplanar distance, at 15.7 A, 14.9 A, 7.5 A, 5.4 A, 3.5 A and 3.4 A.

Figure 2A:
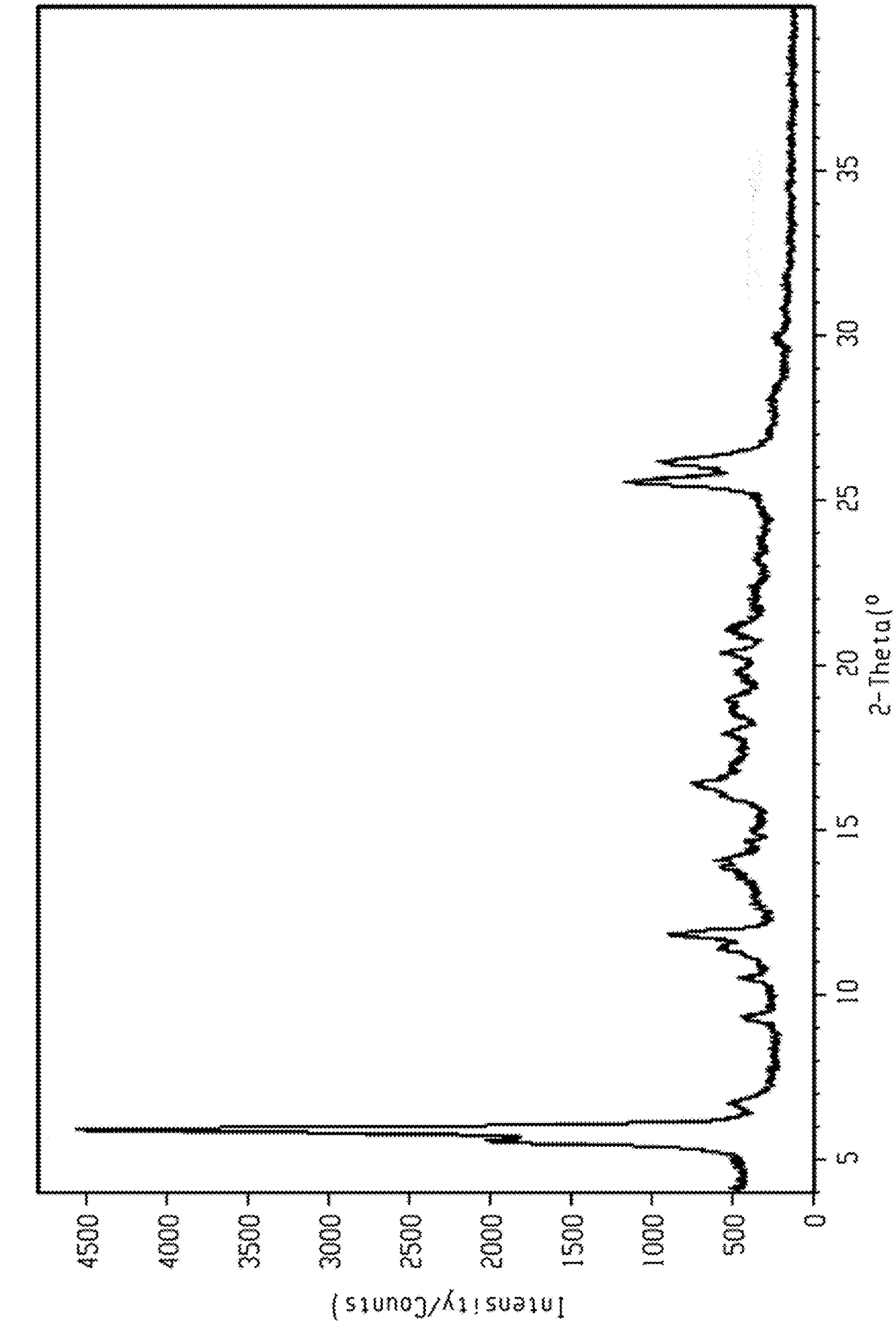

In one embodiment, the X-ray powder diffraction pattern of the Compound 1 freebase in crystalline Form A is substantially shown as in FIG. 2A.

The X-ray diffraction pattern depicted in FIG. 2A is summarized in FIG. 2B.

Figure 3:
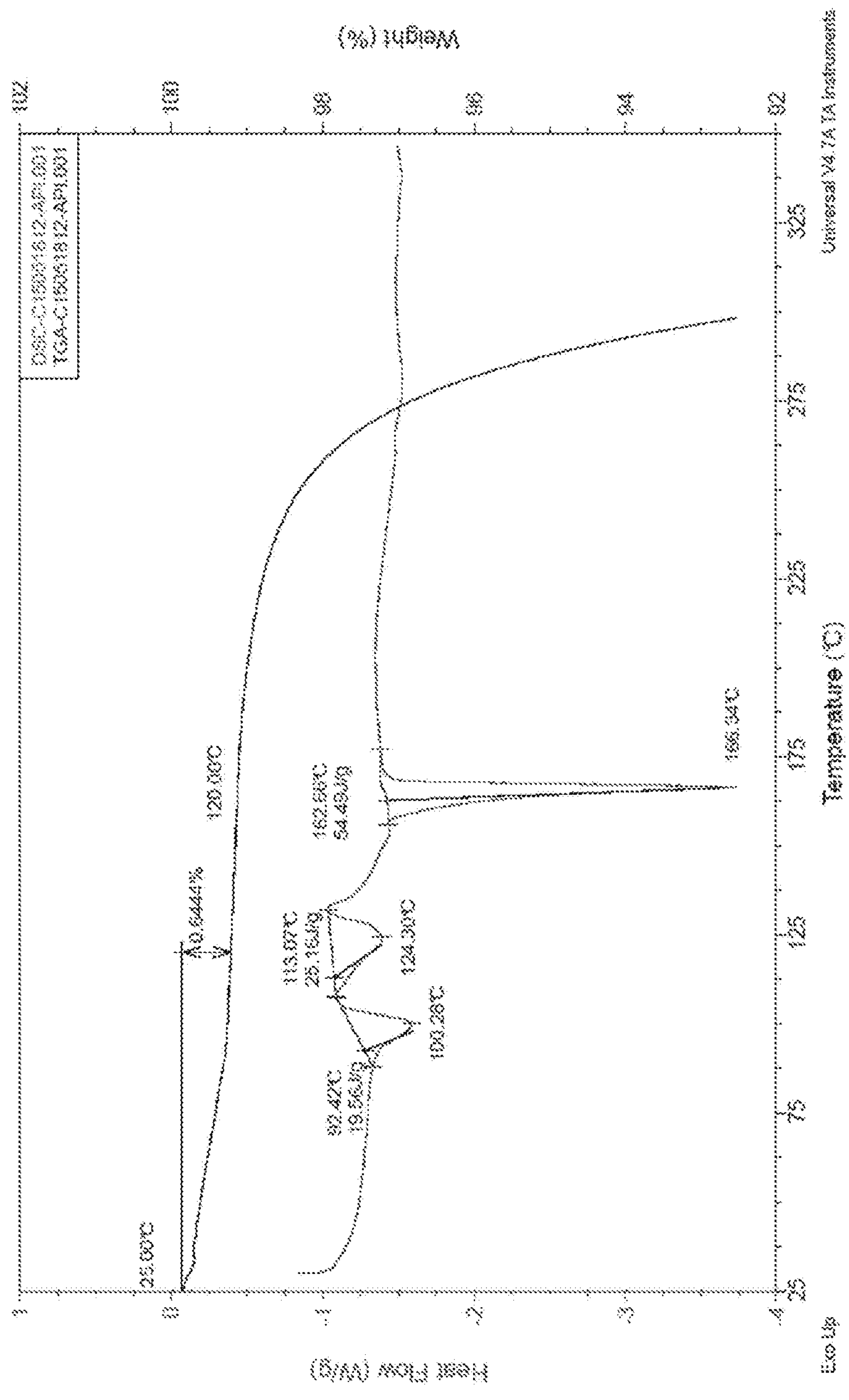
FIG. 3 shows the DSC and TGA profiles of the freebase of Compound 1 (Form A).

In one embodiment, the Compound 1 freebase in crystalline Form A has the TGA profile substantially as shown in FIG. 3.

In one embodiment, the Compound 1 freebase in crystalline Form A has the DSC profile substantially as show in FIG. 3.

In one embodiment, the Compound 1 freebase in crystalline Form A has a DSC profile having characteristic peaks at 100.3° C., 124.3° C. and 166.3° C.

In one embodiment, the Compound 1 freebase in crystalline Form A has a melting point with an onset temperature of approximately 162.3° C.

In another embodiment, the present invention provides a crystalline form of the Compound 1 freebase (Form B) that exhibits an X-ray diffraction pattern comprising characteristic peaks at diffraction angles 2θ of approximately 4.7°, 11.2°, 14.1°, 15.3° and 21.2°, each ±0.2°.

In one embodiment, the X-ray powder diffraction pattern of the Compound 1 freebase in crystalline Form B comprises characteristic peaks, expressed in terms of the interplanar distance, at 18.7 A, 7.9 A, 6.3 A, 5.8 A and 4.2 A.

Figure 6:
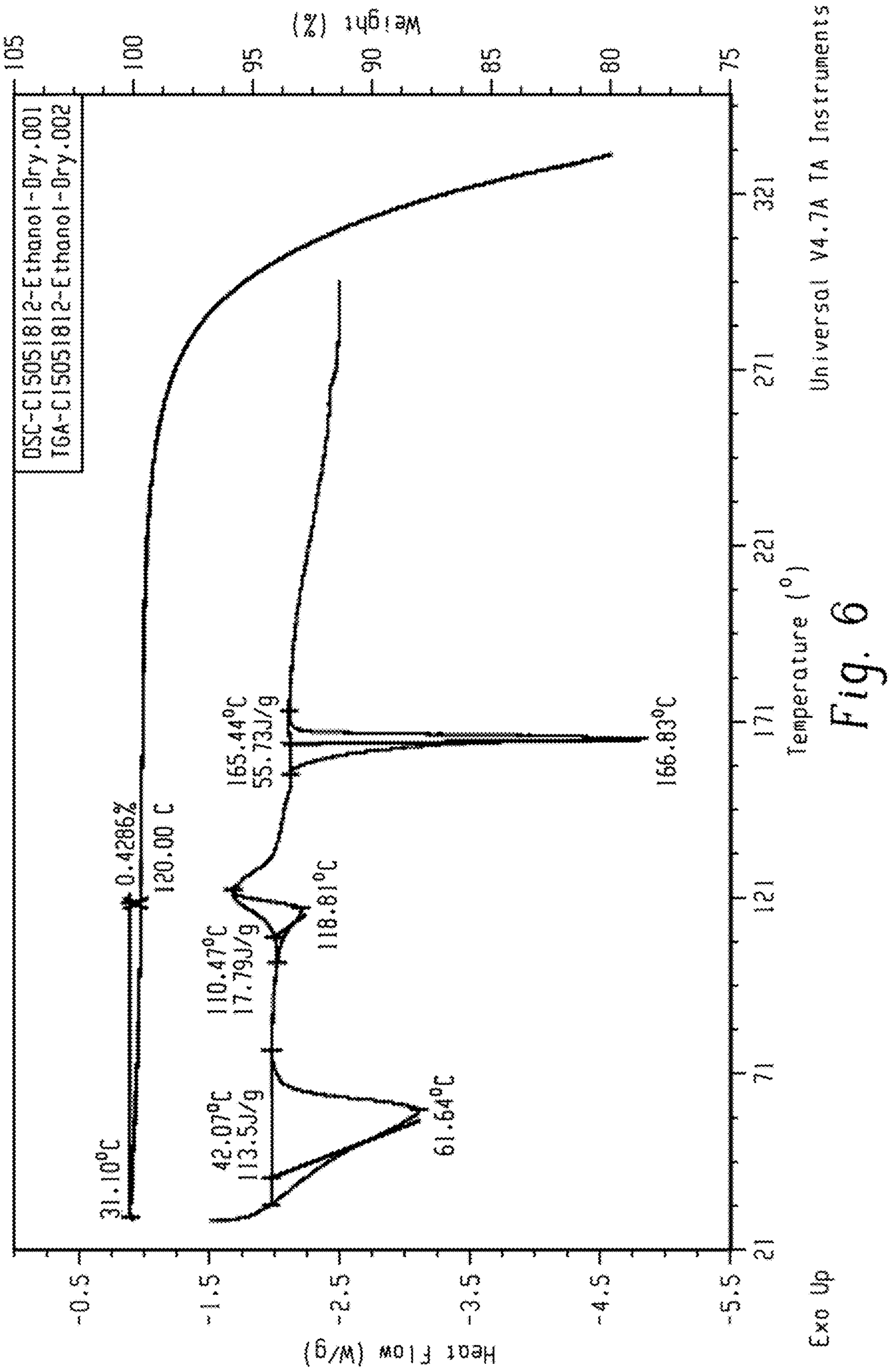
FIG. 6 shows TGA and DSC profiles for the freebase of Compound 1 (Form B).

In one embodiment, the Compound 1 freebase in crystalline Form B has a TGA profile substantially as shown in FIG. 6.

In one embodiment, the Compound 1 freebase in crystalline Form B has a DSC profile substantially as shown in FIG. 6.

In one embodiment, the Compound 1 freebase in crystalline Form B has a DSC profile having characteristic peaks at 61.5° C., 118.8° C. and 166.8° C.

In one embodiment, the Compound 1 freebase in crystalline Form B has a melting point having an onset temperature of approximately 165.4° C.

In another embodiment, the present invention provides a method of preparing the crystalline Form B of the Compound 1 freebase, comprising the steps of slurrying the Compound 1 freebase in crystalline Form A, as illustrated in Table 1, in ethanol, isopropanol or a mixed solvent of ethanol:water (3:1) at about 50° C. for about 24 hours; and isolating the resulting crystalline polymorph B.

In another embodiment, the present invention provides a crystalline polymorph of the Compound 1 freebase (Form C) that exhibits an X-ray powder diffraction pattern comprising characteristic peaks at diffraction angles 2θ of approximately 5.7°, 6.4°, 9.2°, 12.8°, 15.7° and 20.7°, each ±0.2°.

In one embodiment, the X-ray powder diffraction pattern of the Compound 1 freebase in crystalline Form C comprises characteristic peaks expressed in terms of the interplanar distance, at 15.5 A, 13.8 A, 9.6 A, 6.9 A, 5.6 A and 4.3 A.

In one embodiment, the X-ray powder diffraction pattern of the Compound 1 freebase in crystalline Form C comprises characteristic peaks at diffraction angles 2θ of approximately 6.4°, 12.8° and 20.7°, each ±0.2°.

In one embodiment, the X-ray diffraction pattern of the Compound 1 freebase in crystalline Form C comprises characteristic peaks, expressed in terms of the interplanar distance, at 13.8 A, 6.9 A and 5.6 A.

Figure 7:
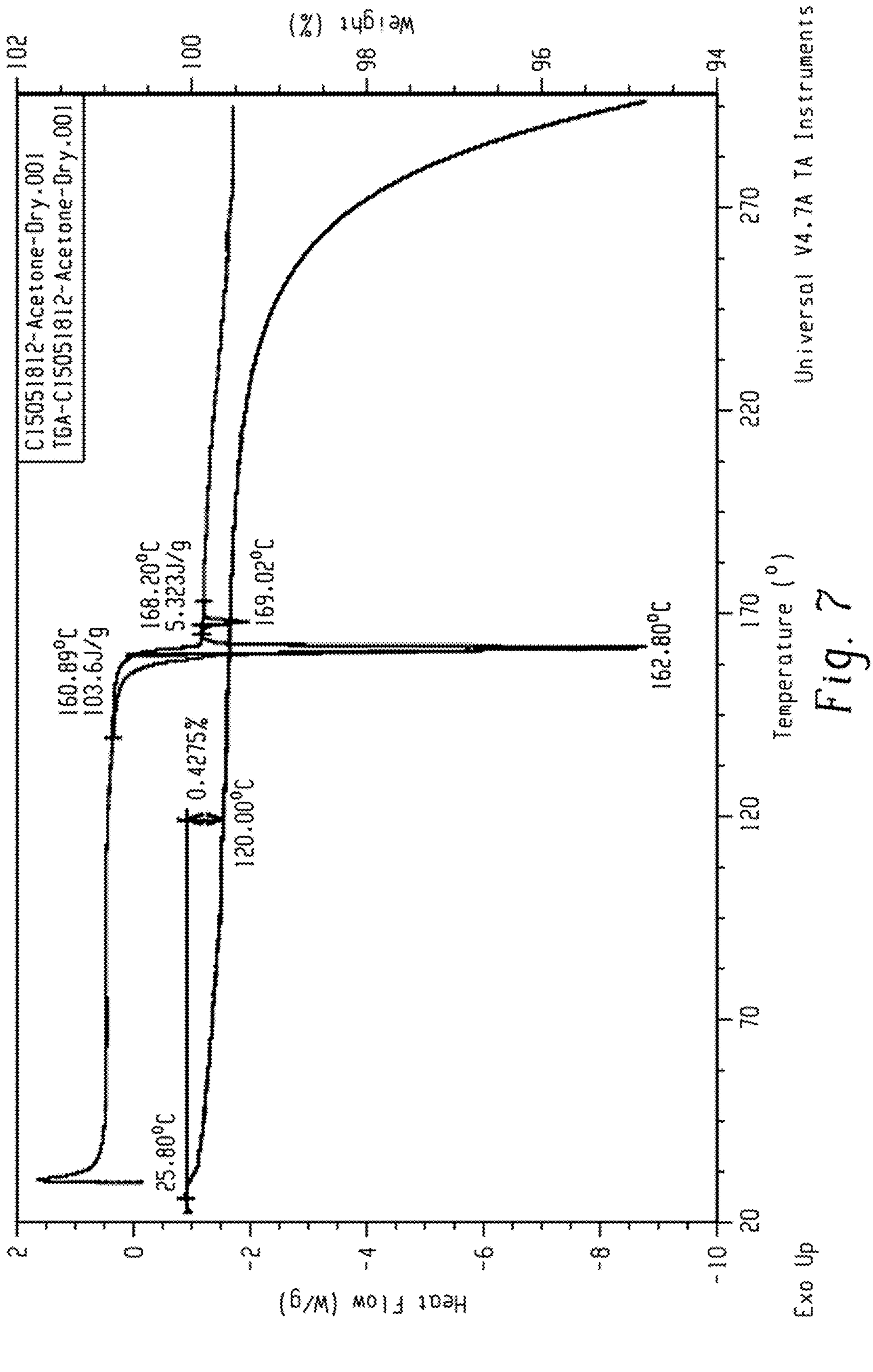
FIG. 7 shows the TGA and DSC profiles for the freebase of Compound 1 (Form C).

In one embodiment, the Compound 1 freebase in crystalline Form C is characterized by a TGA profile substantially as shown in FIG. 7.

In one embodiment, the Compound 1 freebase in crystalline Form C is characterized by a DSC profile substantially as shown in FIG. 7.

In one embodiment, the Compound 1 freebase in crystalline Form C is characterized by a DSC profile having a characteristic peak at 162.8° C.

In one embodiment, the Compound 1 freebase in crystalline Form C has a melting point having an onset temperature of approximately 160.9° C.

In another embodiment, the present invention provides a method of preparing the crystalline polymorph of the Compound 1 freebase in crystalline Form C, comprising the steps of slurrying the Compound 1 freebase in crystalline Form A, as illustrated in Table 1, in acetone at about 50° C. for about 24 hours, and isolating the resulting crystalline polymorph.

Figure 10:
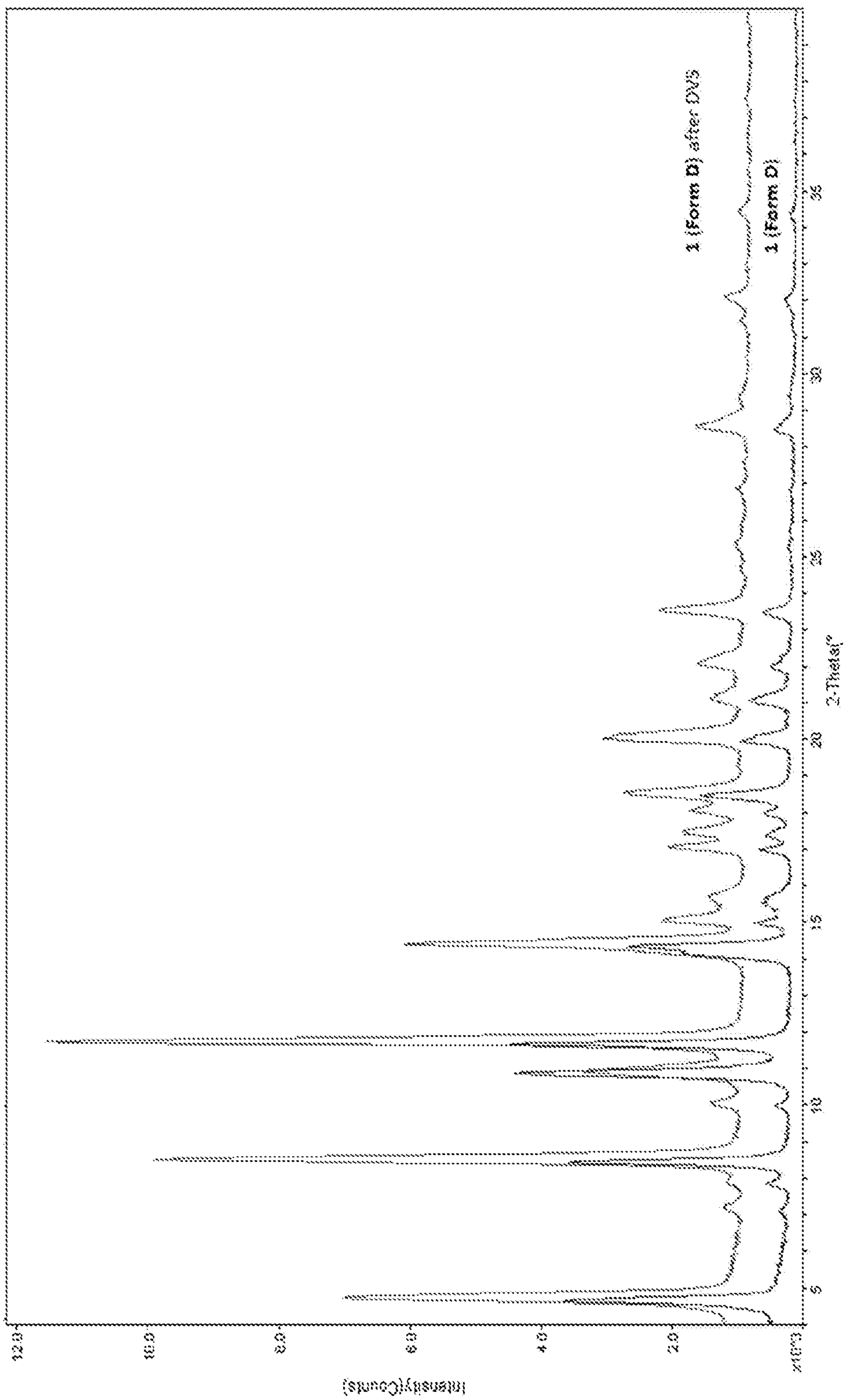
FIG. 10 shows the X-ray powder diffraction patterns of the freebase of Compound 1 (Form D) before and after DVS.
Figure 11:
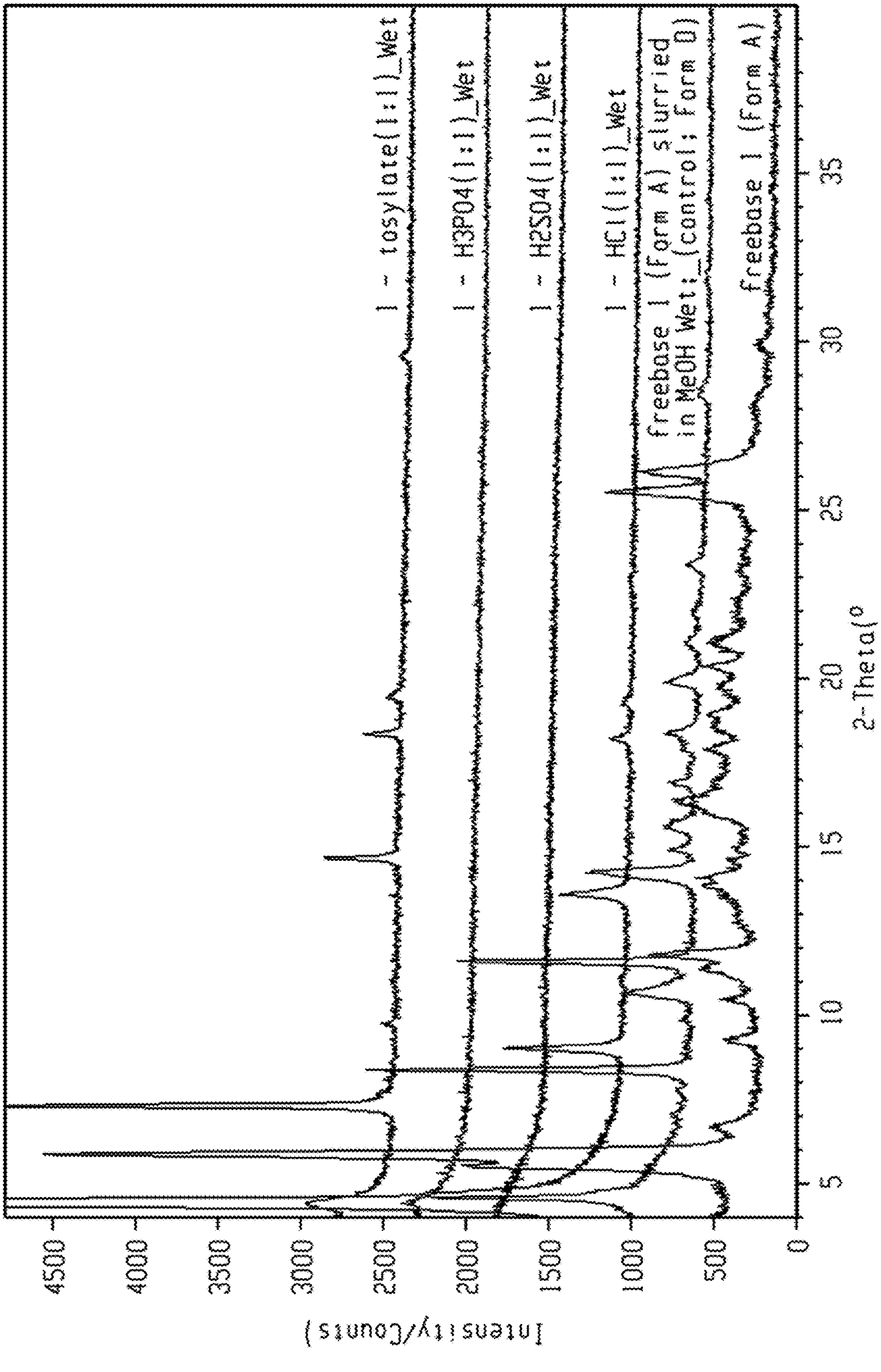
FIG. 11 shows the X-ray powder diffraction patterns (wet samples) of the 50 mg salt screen (freebase:acid) for Compound 1.

In another embodiment, the present invention provides a crystalline polymorph of the Compound 1 freebase (Form D) characterized by the X-ray powder diffraction pattern substantially as shown in FIG. 10, having diffraction pattern comprising characteristic peaks at diffraction angles 2θ of approximately 4.8°, 8.3°, 10.5°, 11.5°, 14.0°, 18.2°, 20.0°, 23.5°, and 28.5°.

Figure 8:
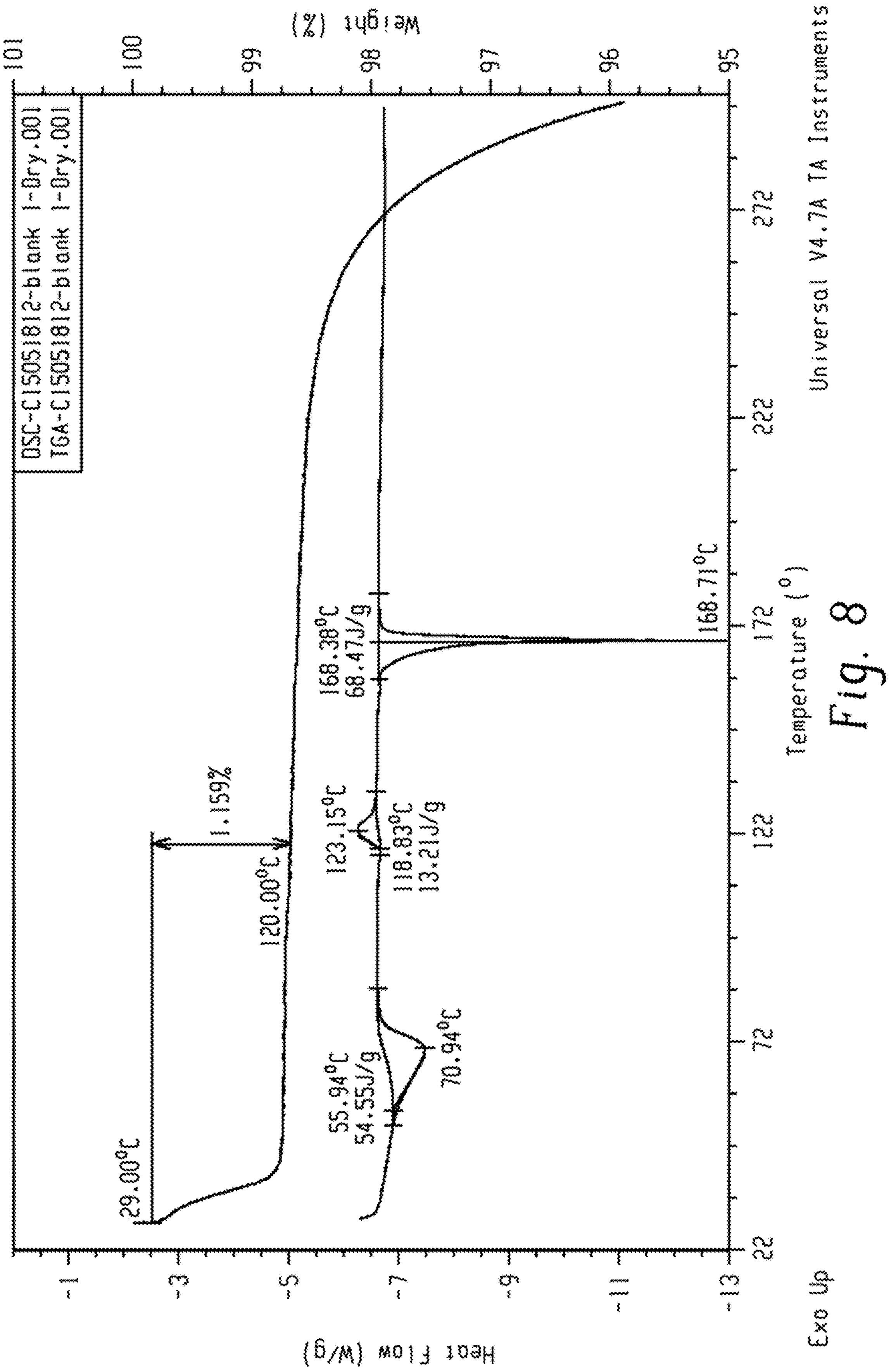
FIG. 8 shows the TGA and DSC profiles for the freebase of the compound of Compound 1 (Form D).

In one embodiment, the Compound 1 freebase in crystalline Form D is characterized by a TGA profile substantially as shown in FIG. 8.

In one embodiment, the Compound 1 freebase in crystalline Form D is characterized by a DSC profile substantially as shown in FIG. 8.

In one embodiment, the Compound 1 freebase in crystalline Form D is characterized by a DSC profile having characteristic peaks at 55.9° C., 118.8° C. and 168.4° C.

Figure 9A:
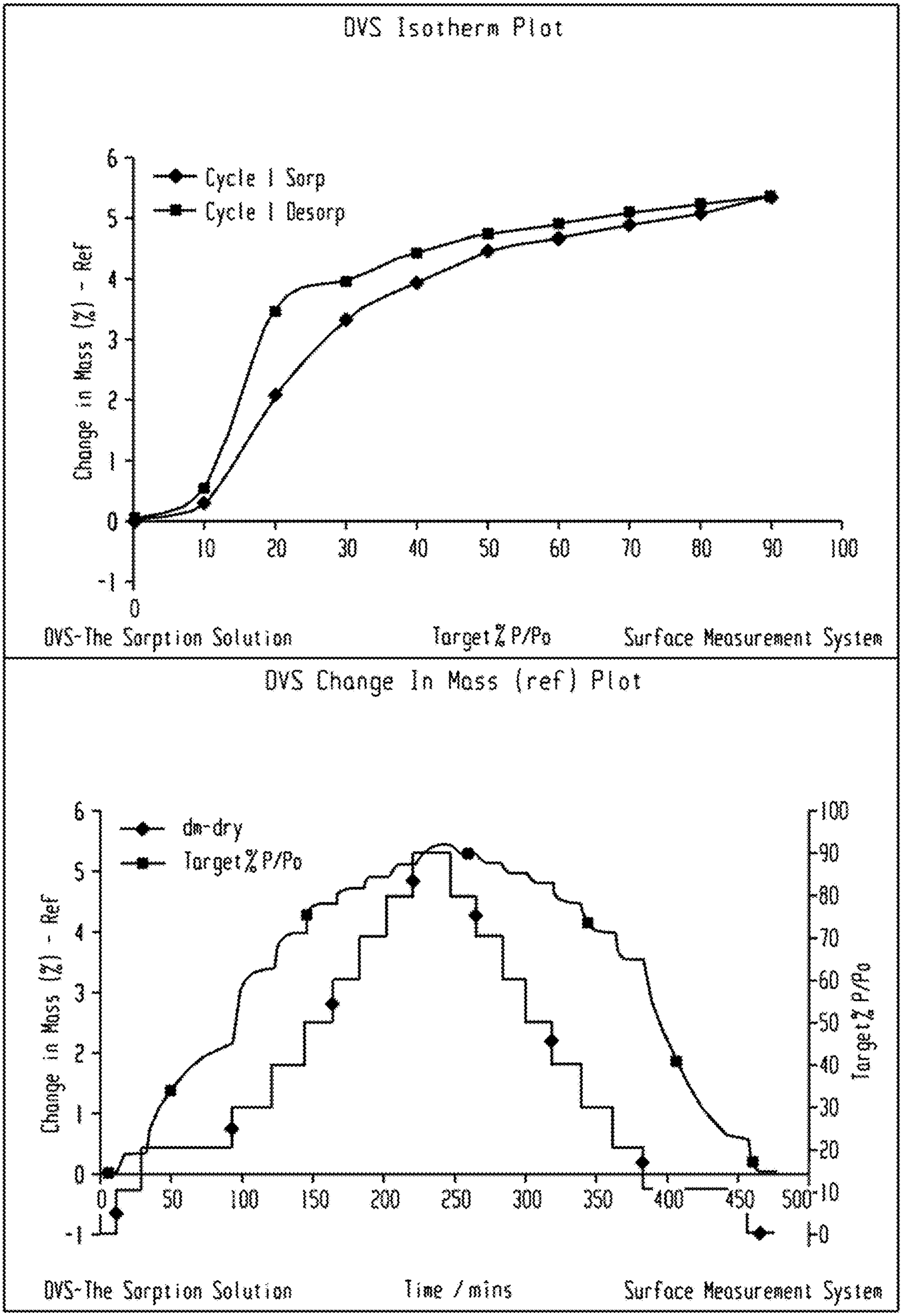

In one embodiment, the Compound 1 freebase in crystalline Form D is characterized by a dynamic vapor sorption isotherm as shown in FIG. 9.

In one aspect, the present invention provides processes for the preparation of crystalline forms of the Compound 1 free base, comprising dissolving or slurrying the Compound 1 in one or two crystallization solvents selected from the group consisting of alcohols, ketones, esters, ethers, aromatic hydrocarbons, nitriles, halogenated hydrocarbons, and water, through a crystallization method selected from slurrying, evaporating solvent, adding anti-solvent, and/or cooling, with or without seeding, and combinations thereof.

In some embodiment, controlled or slow addition of anti-solvent such as water and/or gradual cooling may help control the formation of crystalline forms.

In some embodiments, seeding may help formation or facilitate formation of certain desired crystalline forms. All these or other techniques as known to those skilled in the art may be combined to obtain desired results. For example, in some embodiments, such crystallization processes can start from dissolving the compound 1 in an organic solvent, followed by adding an anti-solvent, cooling, with or without seeding.

In another embodiment, the present invention provides a method of preparing the crystalline polymorph of Compound 1 freebase in crystalline Form D, comprising the steps of slurrying the Compound 1 freebase in crystalline Form A, as illustrated in Table 1, in methanol at about room temperature for about 24 hours, and isolating the resulting crystalline polymorph.

The present invention further provides crystalline polymorphic salts of Compound 1.

The present invention provides salts of Compound 1, comprising a compound of Formula 1 and an acid, wherein the acid is selected from HCl, $H_2SO_4$, $H_3PO_4$, methanesulfonic acid and p-toluenesulfonic acid.

In one aspect, the present invention also provides processes for the preparation of crystalline forms of pharmaceutically acceptable salts of the Compound 1, comprising mixing, and stirring a mixture of, the Compound 1 and an appropriate acid, for example, HCl, $H_2SO_4$, $H_3PO_4$, methanesulfonic acid and p-toluenesulfonic acid, in one or two crystallization solvents selected from the group consisting of alcohols, ketones, esters, ethers, aromatic hydrocarbons, nitriles, halogenated hydrocarbons, and water, through a crystallization method selected from slurrying, evaporating solvent, adding anti-solvent, and/or cooling, with or without seeding, and combinations thereof.

In some embodiments, seeding may help formation or facilitate formation of certain desired crystalline forms. For example, in some embodiments, a crystallization process can start from dissolving the compound 1 in an organic solvent at an elevated temperature, followed by adding an anti-solvent, cooling, with or without seeding.

In some embodiments, seeding may help formation or facilitate formation of certain desired crystalline form. For water soluble salts, some non-polar organic solvents may serve as anti-solvents, such as aliphatic hydrocarbons. All these or other techniques known to those skilled in the art may be combined to obtain desired results.

In one embodiment, the present invention provides a crystalline hydrochloride salt of N-(5-((4-ethylpiperazin-1-yl)methyl)pyridin-2-yl-5-fluoro-4-(3-isopropyl-2-methyl-2H-indazol-5-yl)pyrimidin-2-amine.

In one embodiment, the crystalline hydrochloride salt has a molar ratio of N-(5-((4-Ethylpiperazin-yl)methyl)pyridin-2-yl-5-fluoro-4-(3-isopropyl-2-methyl-2H-indazol-5-yl)pyrimidin-2-amine to hydrochloride of 1:1.

In one embodiment, the hydrochloride salt of Compound 1 in crystalline Form A has an X-ray powder diffraction pattern comprising characteristic peaks at diffraction angles 2θ of approximately 4.7°, 9.2°, 11.2°, 19.4° and 28.3°, each ±0.2°.

Figure 18A:
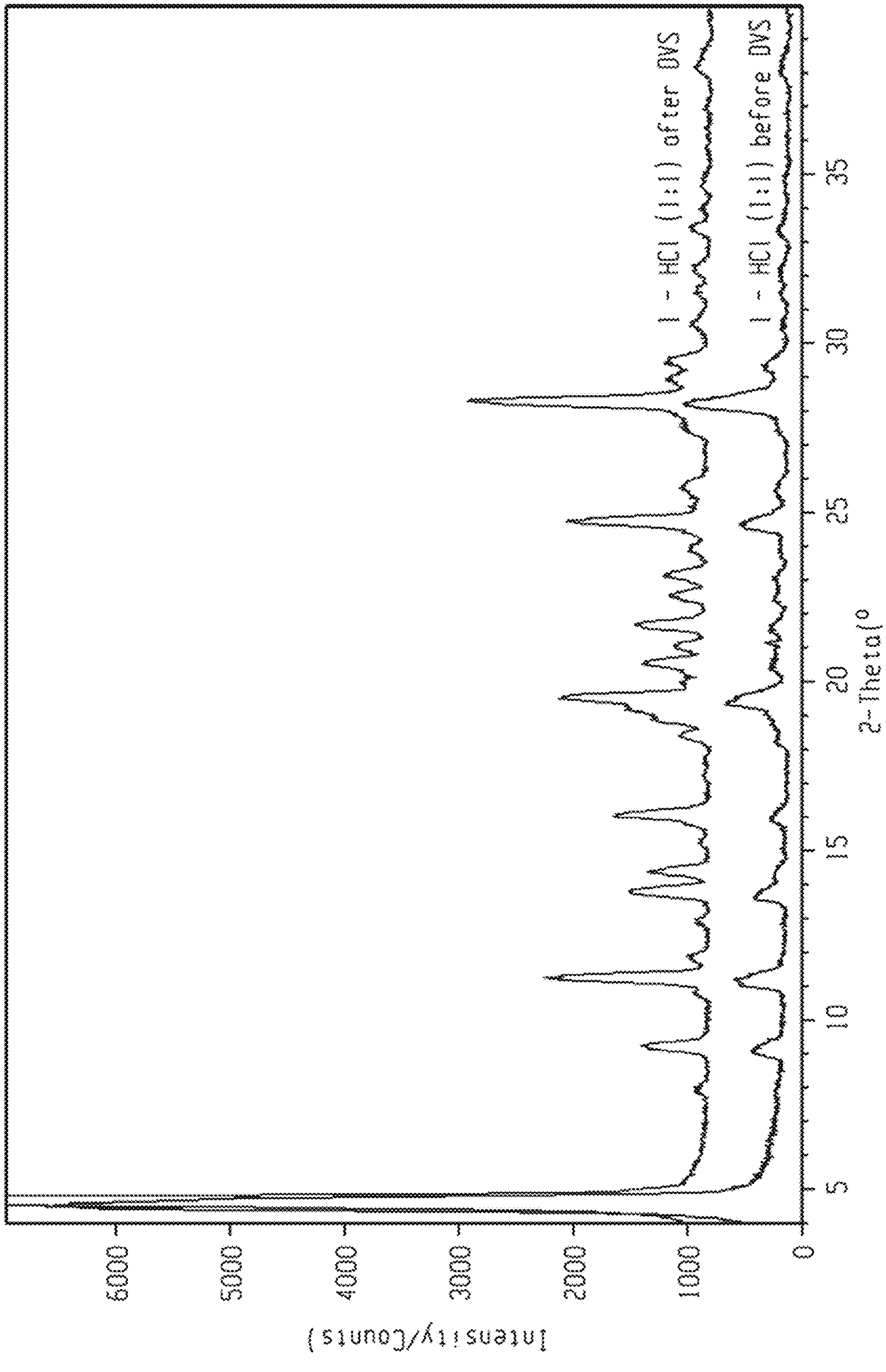

In one embodiment, the X-ray powder diffraction pattern of the hydrochloride salt of Compound 1 in crystalline Form A is substantially shown as in FIG. 18.

Figure 16:
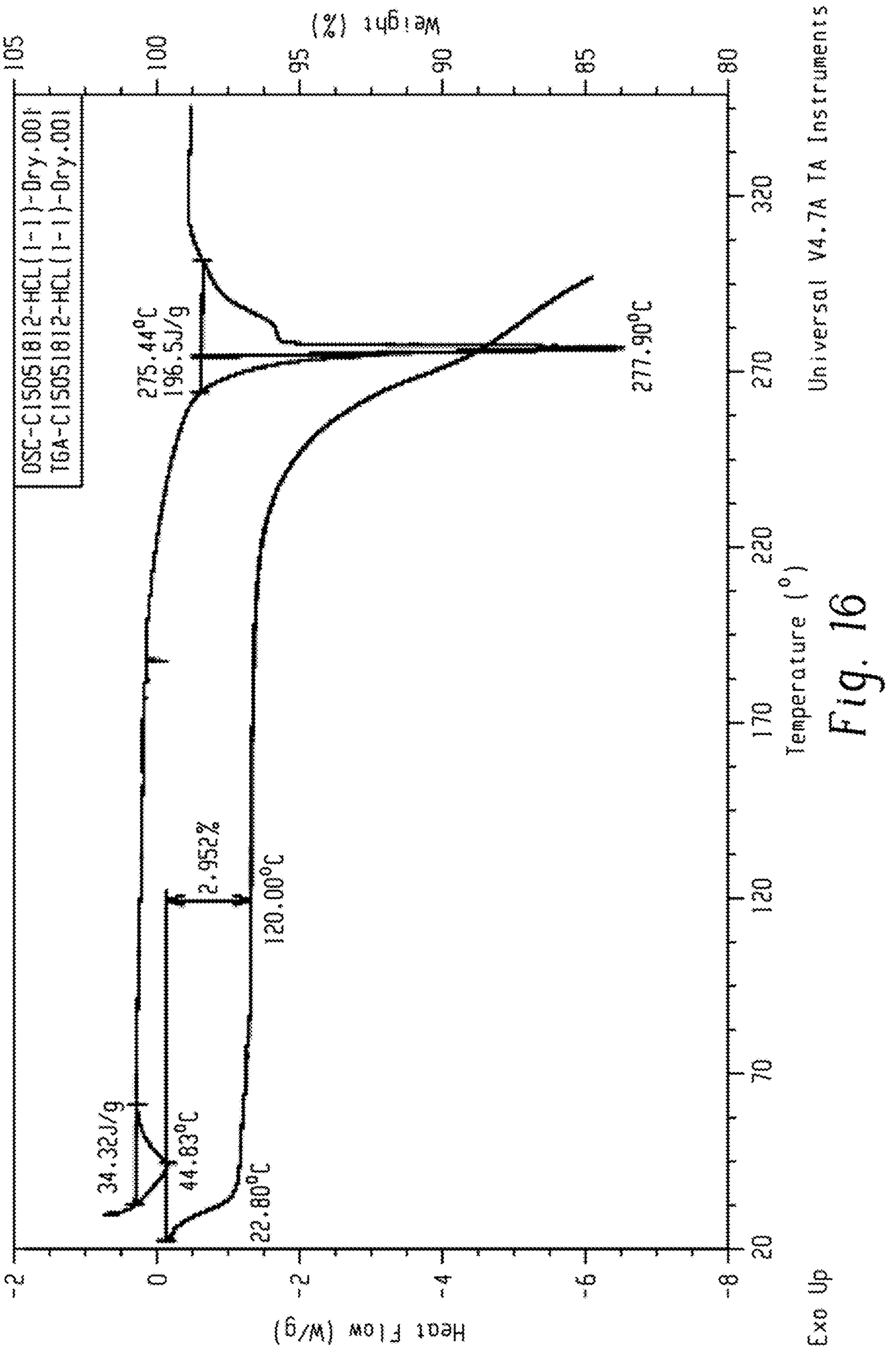
FIG. 16 shows the TGA and DSC profiles (dry sample) of Compound 1 •HCl (1:1; Form A).

In one embodiment, the crystalline hydrochloride salt of Compound 1 in crystalline Form A is characterized by a TGA profile substantially as shown in FIG. 16.

In one embodiment, the crystalline hydrochloride salt of Compound 1 in crystalline Form A is characterized by a DSC profile substantially as shown in FIG. 16.

In one embodiment, the crystalline hydrochloride salt of Compound 1 in crystalline Form A is characterized by a DSC profile having characteristic peaks at 44.8° C. and 277.9° C.

In one embodiment, the crystalline hydrochloride salt of Compound 1 in crystalline Form A is characterized by a melting point having an onset temperature of approximately 275.4° C.

Figure 17A:
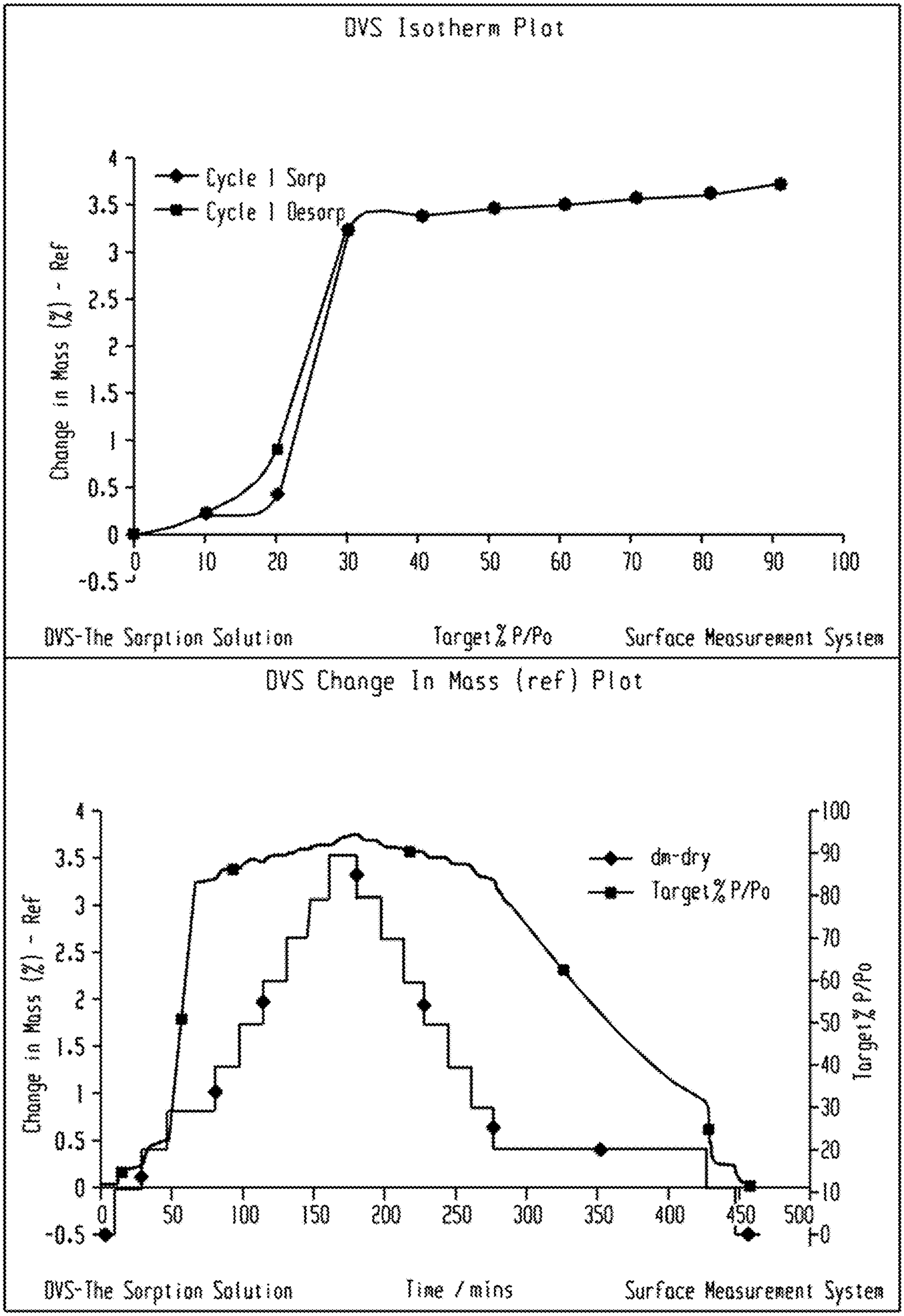

In one embodiment the crystalline hydrochloride salt of Compound 1 in crystalline Form A has a dynamic vapor sorption isotherm substantially as shown in FIG. 17.

In another embodiment, the invention provides a method of preparing the crystalline hydrochloride (Form A) of Compound 1, comprising:

(a) adding a solution of HCl/methanol to a mixture of the compound of Formula 1 (Form A used, though not so limited) in methanol;

(b) stirring for about 24 hours at about room temperature; and (c) isolating the resulting crystalline HCl salt of the Compound 1.

Figure 35:
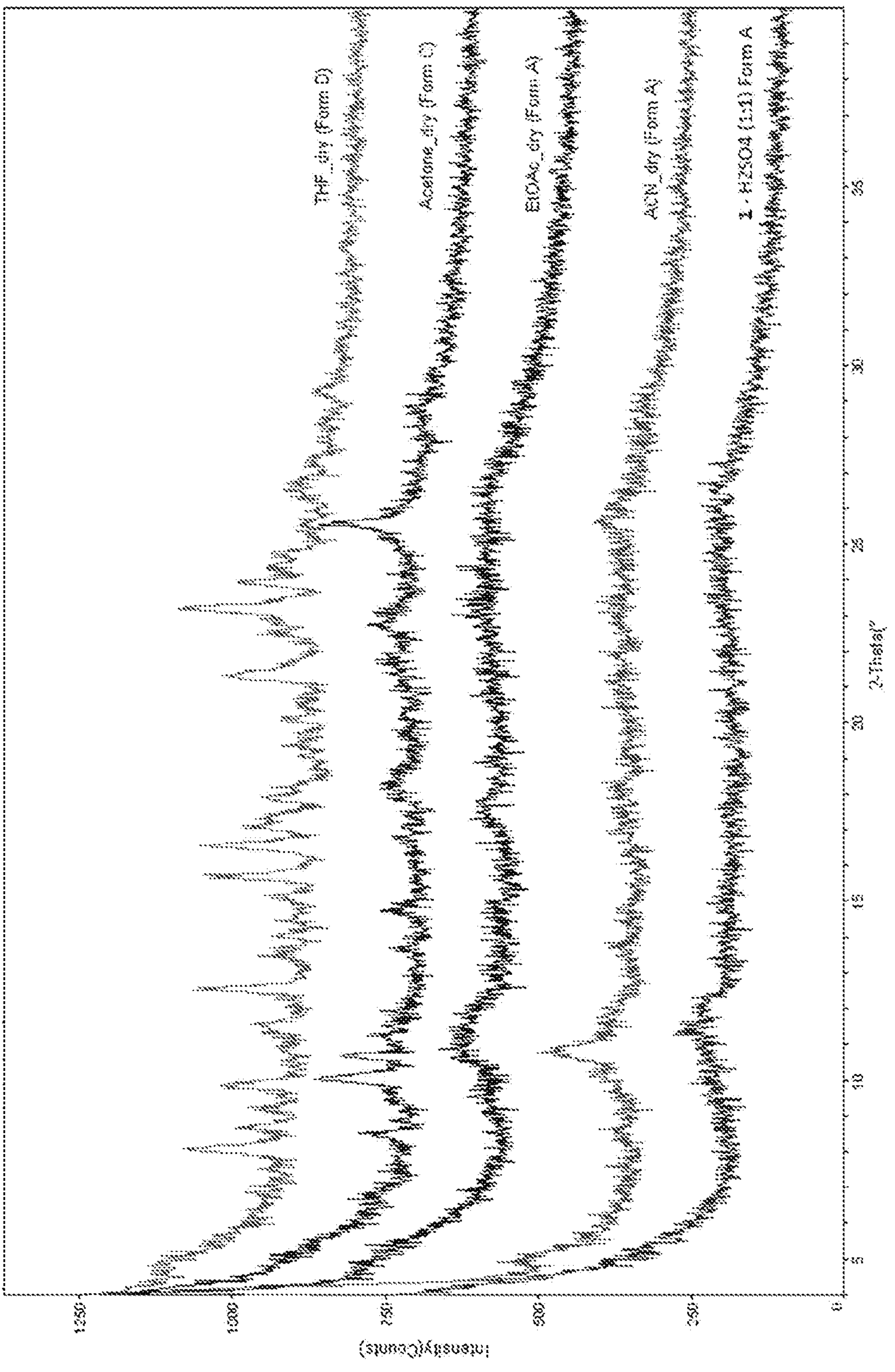
FIG. 35 shows the X-ray powder diffraction patterns of dry samples of Compound 1. $H_2SO_4$ (1:1) polymorphs Forms A, C and D derived from stirring a slurry of Form A in 100 μL of various solvents for 1 day at 40° C. Form B converted to Form A after heating at 40° C.
Figure 36:
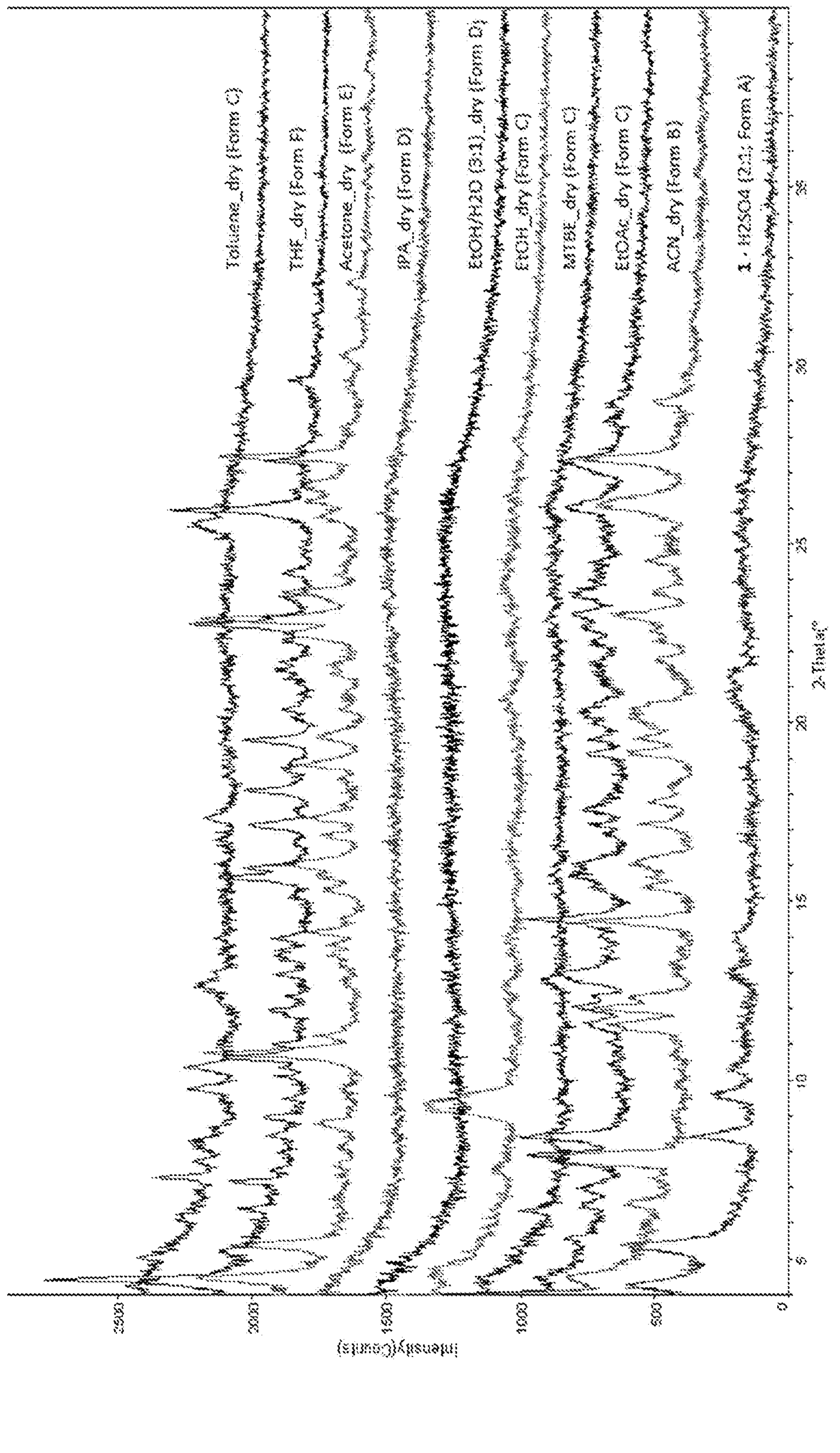
FIG. 36 shows the X-ray powder diffraction patterns of dry samples of new crystalline polymorphs Forms B, C, E and F of Compound 1 •$H_2SO_4$ (2:1) derived from stirring a slurry of Form A in 100 μL of various solvents for 1 day at 40° C. Form D was amorphous and was isolated after evaporation of EtOH:$H_2O$ (3:1) over several hours
Figure 37:
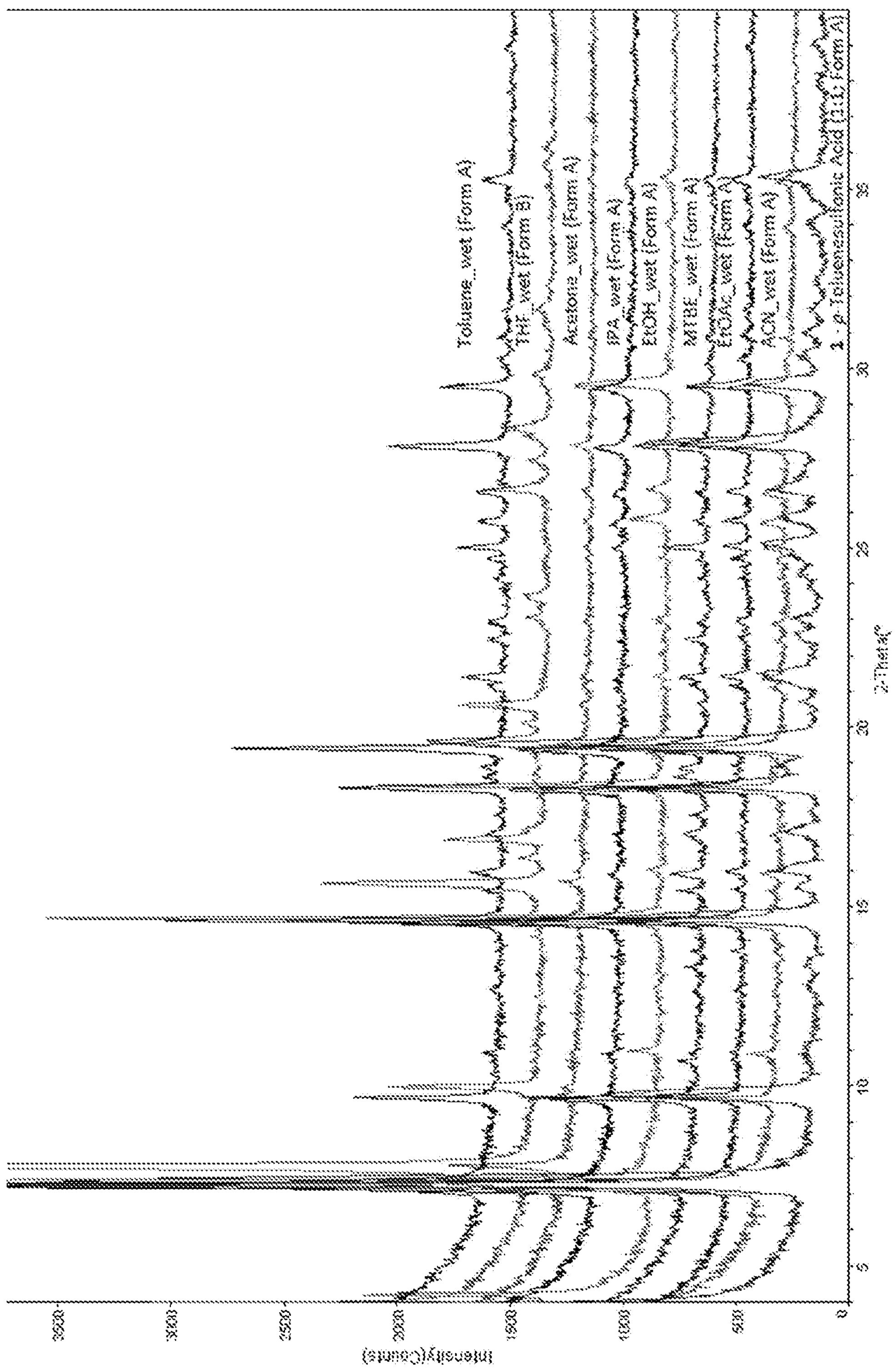
FIG. 37 shows the X-ray powder diffraction patterns of wet samples from the polymorph screening study for Compound 1•p-toluenesulfonic acid derived from stirring a slurry of Form A in 100 μL of various solvents for 1 day at 40° C. Form C was mostly amorphous and was isolated after evaporation of EtOH:$H_2O$ (3:1) over several hours.
Figure 38:
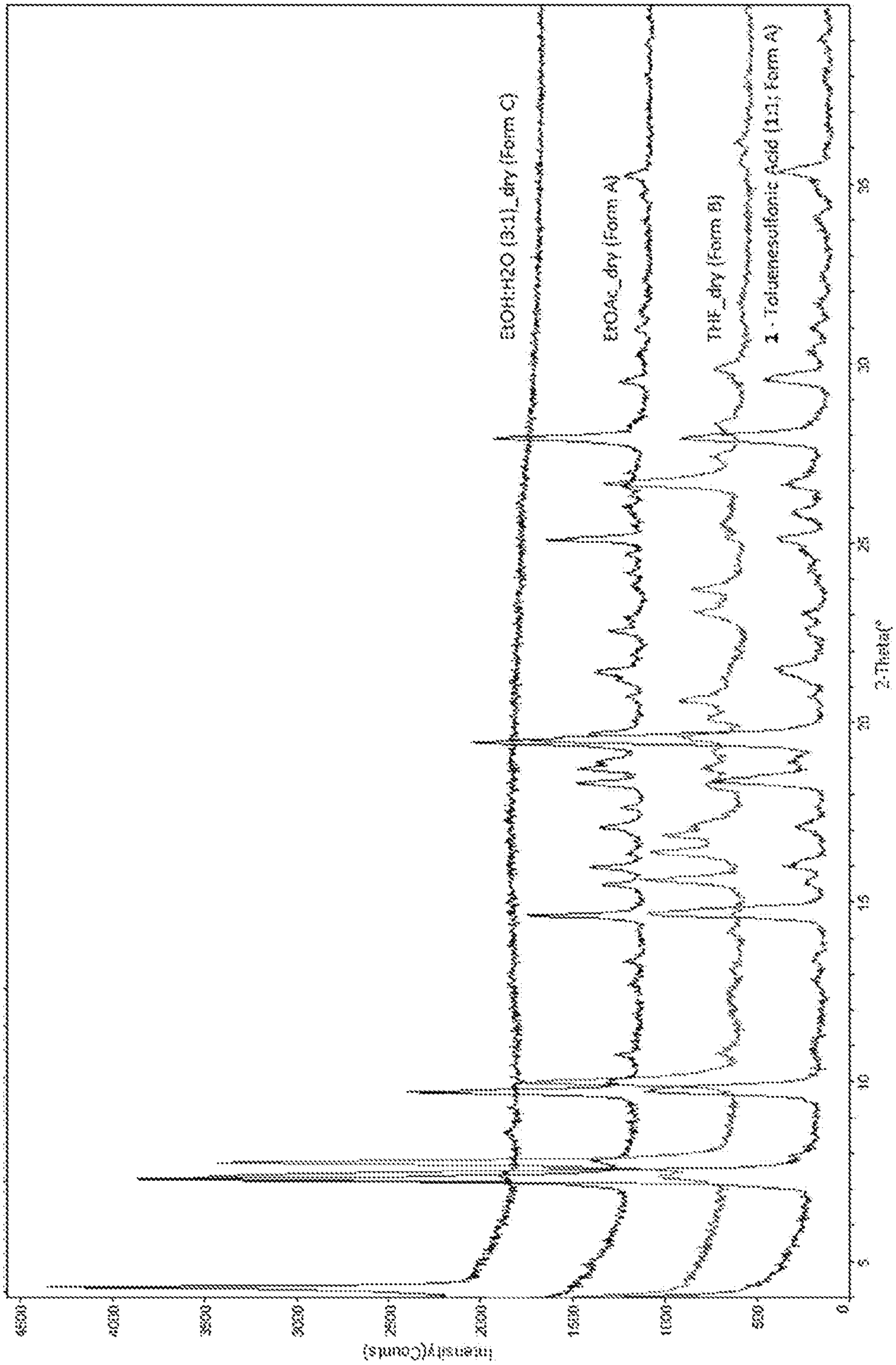
FIG. 38 shows the X-ray powder diffraction patterns of dry samples from a polymorph screening study for Compound 1•p-toluenesulfonic acid derived from stirring a slurry of Form A in 100 μL of various solvents for 1 day at 40° C. Form C was mostly amorphous and was isolated after evaporation of EtOH:$H_2O$ (3:1) over several hours.

In some embodiments, the acid addition salt of Compound 1 is a sulfuric acid salt with the Compound 1 and $H_2SO_4$ in about 1:1 molar ratio, in a crystalline form selected from the group consisting of Form B, Form C, or Form D substantially as shown in FIG. 35 or 36, wherein: Form B is characterized by an X-ray powder diffraction pattern comprising any three (3) of characteristic peaks at diffraction angles 2θ of approximately 4.2°, 4.8°, 7.0°, 9.1°, 10.8°, 11.3°, and 12.0°; wherein Form C is characterized by an X-ray powder diffraction pattern comprising any three (3) of characteristic peaks at diffraction angles 2θ of approximately 5.0°, 8.6°, 10.2°, 18.3°, and 25.7°; and wherein Form D is characterized by an X-ray powder diffraction pattern comprising any three (3) of characteristic peaks at diffraction angles 2θ of approximately 8.1°, 9.8°, 12.6°, 15.8°, 16.6°, 21.4°, and 23.2°.

In another embodiment, the present invention provides a crystalline sulfate salt of N-(5-((4-ethylpiperazin-1-yl)methyl)pyridin-2-yl-5-fluoro-4-(3-isopropyl-2-methyl-2H-indazol-5-yl)pyrimidin-2-amine.

In one embodiment, the crystalline sulfate salt has a molar ratio of crystalline sulfate salt of N-(5-((4-ethylpiperazin-1-yl)methyl)pyridin-2-yl-5-fluoro-4-(3-isopropyl-2-methyl-2H-indazol-5-yl)pyrimidin-2-amine to sulfate of 1:1.

In one embodiment, the crystalline sulfate salt has a molar ratio of crystalline sulfate salt of N-(5-((4-ethylpiperazin-1-yl)methyl)pyridin-2-yl-5-fluoro-4-(3-isopropyl-2-methyl-2H-indazol-5-yl)pyrimidin-2-amine to sulfate of 2:1.

In some embodiments, the acid addition salt of Compound 1 is a sulfuric acid salt with the Compound 1 and $H_2SO_4$ in about 2:1 molar ratio, in a crystalline form selected from the group consisting of Form A, Form B, Form C, Form E, and Form F, or substantially as shown in FIG. 36, wherein: Form A is characterized by an X-ray powder diffraction pattern comprising characteristic peaks at diffraction angles 2θ of approximately 4.3°, 5.4° and 8.4°; Form B is characterized by an X-ray powder diffraction pattern comprising any three (3) of characteristic peaks at diffraction angles 2θ of approximately 7.9°, 11.6°, 12.1°, 14.5°, 16.1°, 20.4°, 23.10, 26.1°, and 27.4°; Form C is characterized by an X-ray powder diffraction pattern comprising any three (3) of characteristic peaks at diffraction angles 2θ of approximately 4.6°, 7.5°, 9.3°, 12.3°, and 12.6°; and wherein Form E is characterized by an X-ray powder diffraction pattern comprising any three (3) of characteristic peaks at diffraction angles 2θ of approximately 4.5°, 5.4°, 10.8°, 14.2°, 16.1°, 18.9°, 22.6°, 23.0°, 23.7°, and 27.5°; Form F is characterized by an X-ray powder diffraction pattern comprising any three (3) of characteristic peaks at diffraction angles 2θ of approximately 4.5°, 7.2°, 10.7°, 15.7°, 16.0°, 17.2°, 18.2°, 19.5°, 22.8°, and 26.0°; wherein Form G is characterized by an X-ray powder diffraction pattern comprising any three (3) of characteristic peaks at diffraction angles 2θ of approximately 7.3°, 8.3°, 9.7°, 10.4°, 12.8°, and 25.6°.

Figure 22:
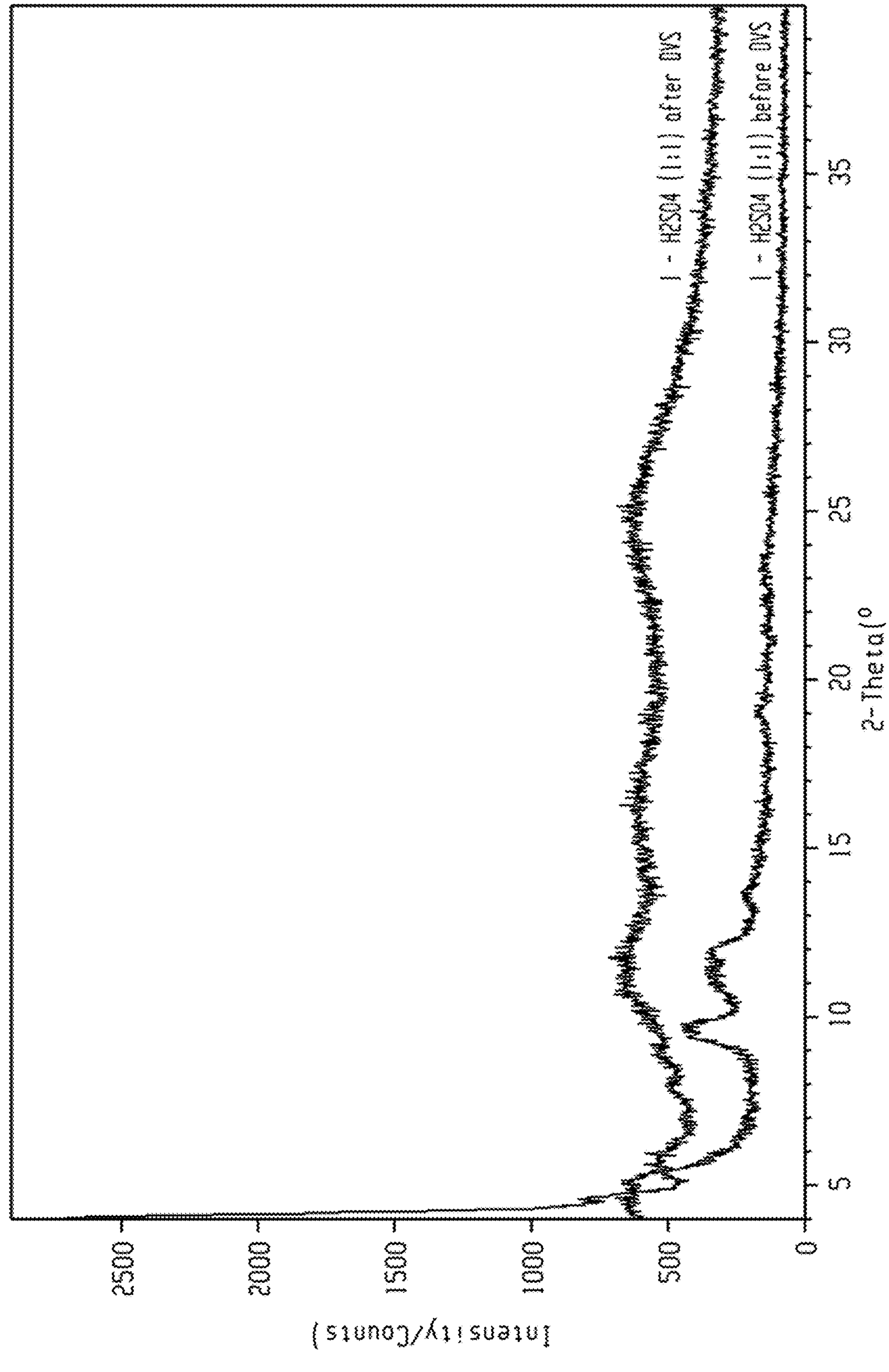
FIG. 22 shows the X-ray powder diffraction patterns of Compound 1 •$H_2SO_4$ (1:1; Form A) from the 50 mg scale before and after DVS isotherm analysis.

In one embodiment, the crystalline sulfate salt of Compound 1 in crystalline Form A is characterized by the X-ray powder diffraction pattern comprising characteristic peaks at diffraction angles 2θ of approximately 4.3°, 5.4° and 8.4°, each ±0.2°, and/or as substantially shown in FIG. 22 (bottom line, before DVS).

Figure 20:
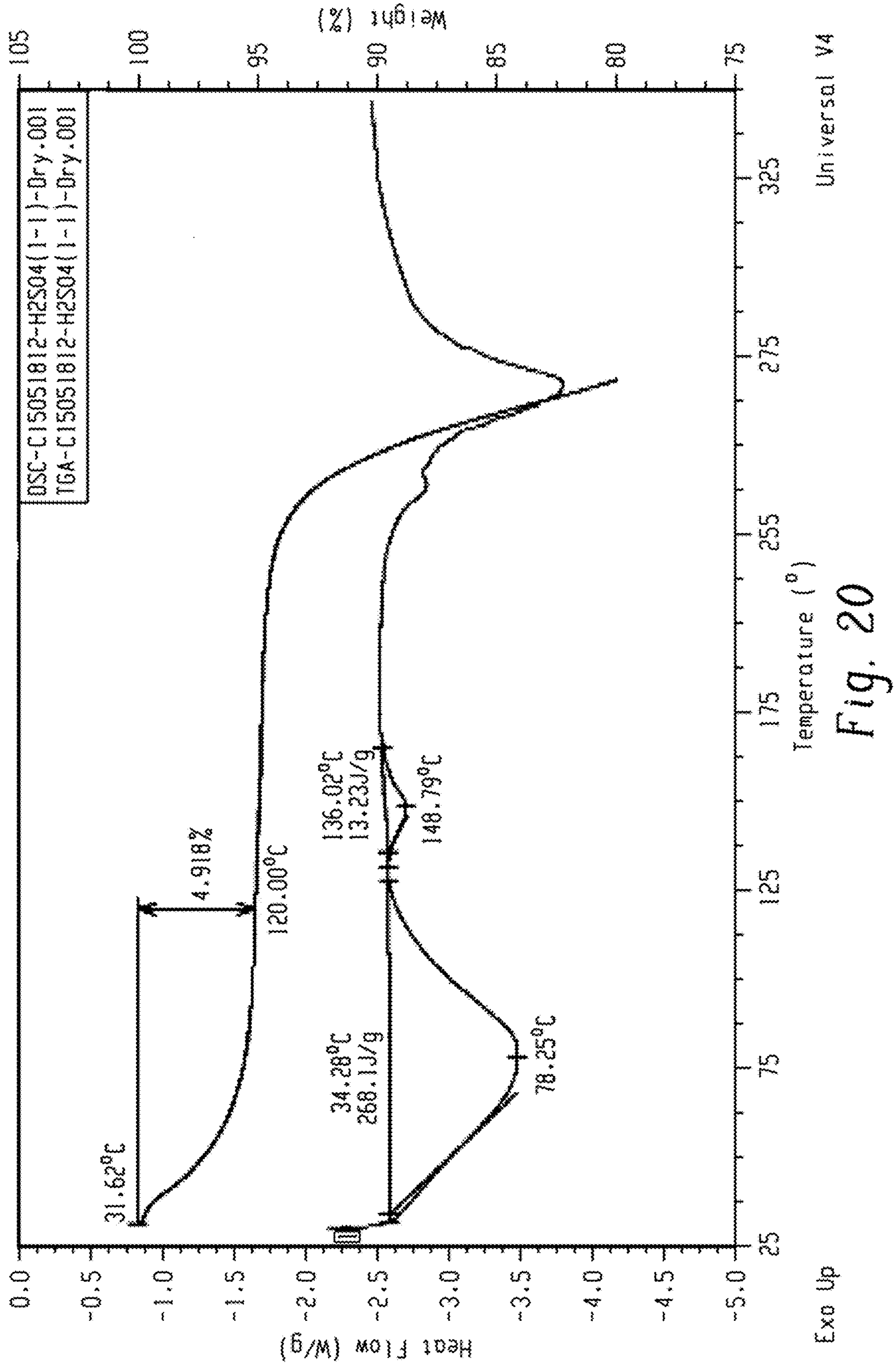
FIG. 20 shows the TGA and DSC profiles of Compound 1 •$H_2SO_4$ (1:1; Form A) from the 50 mg scale salt screen.

In one embodiment, the crystalline sulfate sale of Compound 1 in crystalline Form A is characterized by a DSC and/or TGA profile substantially as shown in FIG. 20.

In another embodiment, the present invention provides a method of preparing the crystalline sulfate (Form A) of Compound A, comprising:

(a) adding a solution of $H_2SO_4$/methanol to a mixture of the compound of Formula 1 (Form A used, but not limiting) in methanol;

(b) stirring for about 24 hours at about room temperature; and (c) isolating the resulting crystalline $H_2SO_4$ salt of the Compound 1.

In one embodiment, the present invention provides a crystalline phosphate salt of N-(5-((4-ethylpiperazin-1-yl)methyl)pyridin-2-yl-5-fluoro-4-(3-isopropyl-2-methyl-2H-indazol-5-yl)pyrimidin-2-amine.

In one embodiment, the crystalline phosphate salt has a molar ratio of crystalline phosphate salt of N-(5-((4-Ethylpiperazin-yl)methyl)pyridin-2-yl-5-fluoro-4-(3-isopropyl-2-methyl-2H-indazol-5-yl)pyrimidin-2-amine to phosphate of about 1:1.

In one embodiment, the crystalline phosphate salt of Compound 1 (crystalline Form A) has an X-ray powder diffraction pattern comprising characteristic peaks at diffraction angles 2θ of approximately 4.7°, 9.4°, 14.2°, 23.0° and 26.7°, each ±0.2°.

Figure 25:
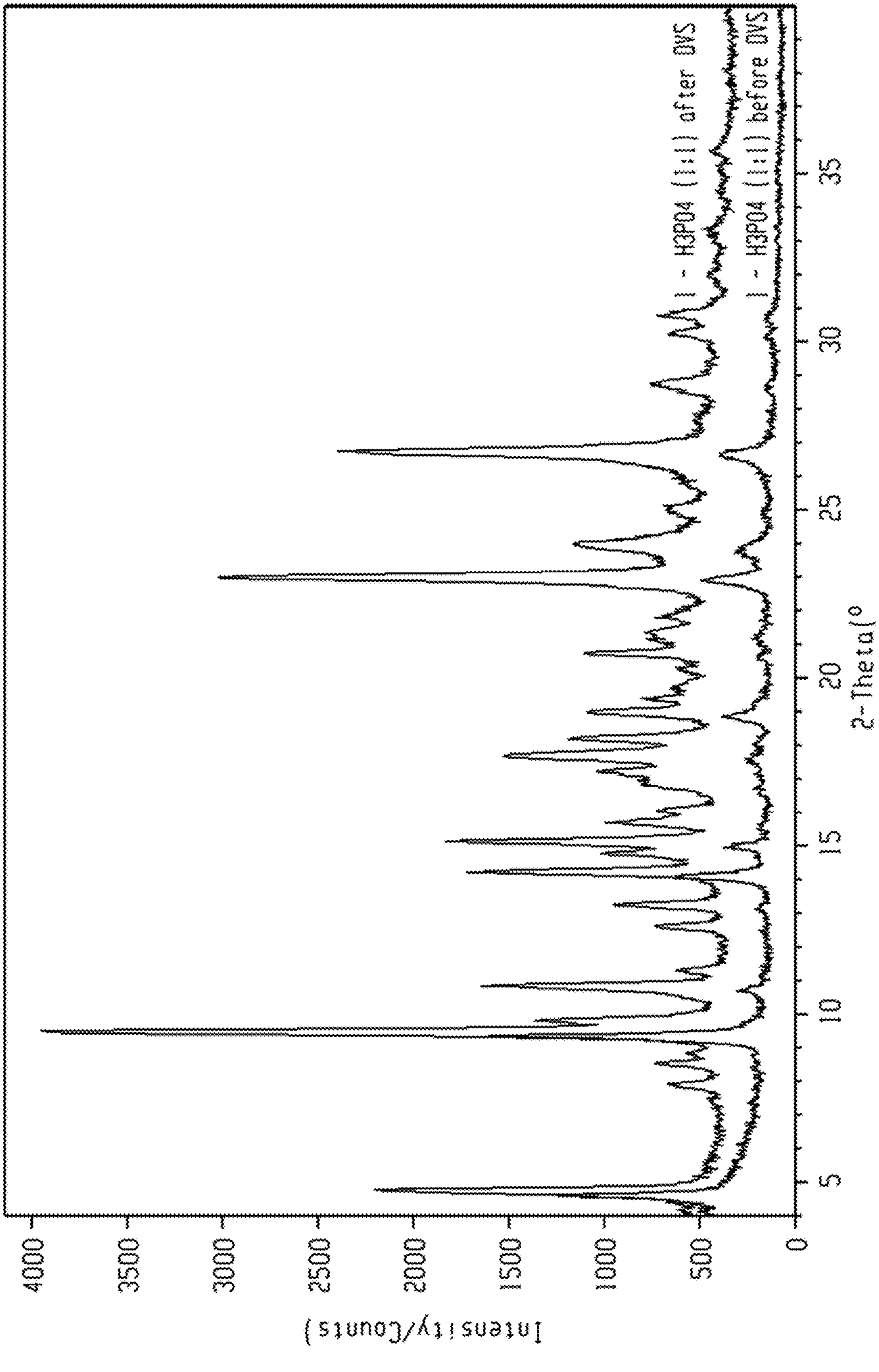
FIG. 25 shows the X-ray powder diffraction patterns of Compound 1 •$H_3PO_4$ (1:1; Form A) before and after DVS.

In one embodiment, the X-ray powder diffraction pattern of the phosphate salt of Compound 1 in crystalline Form A is substantially as shown in FIG. 25.

Figure 23:
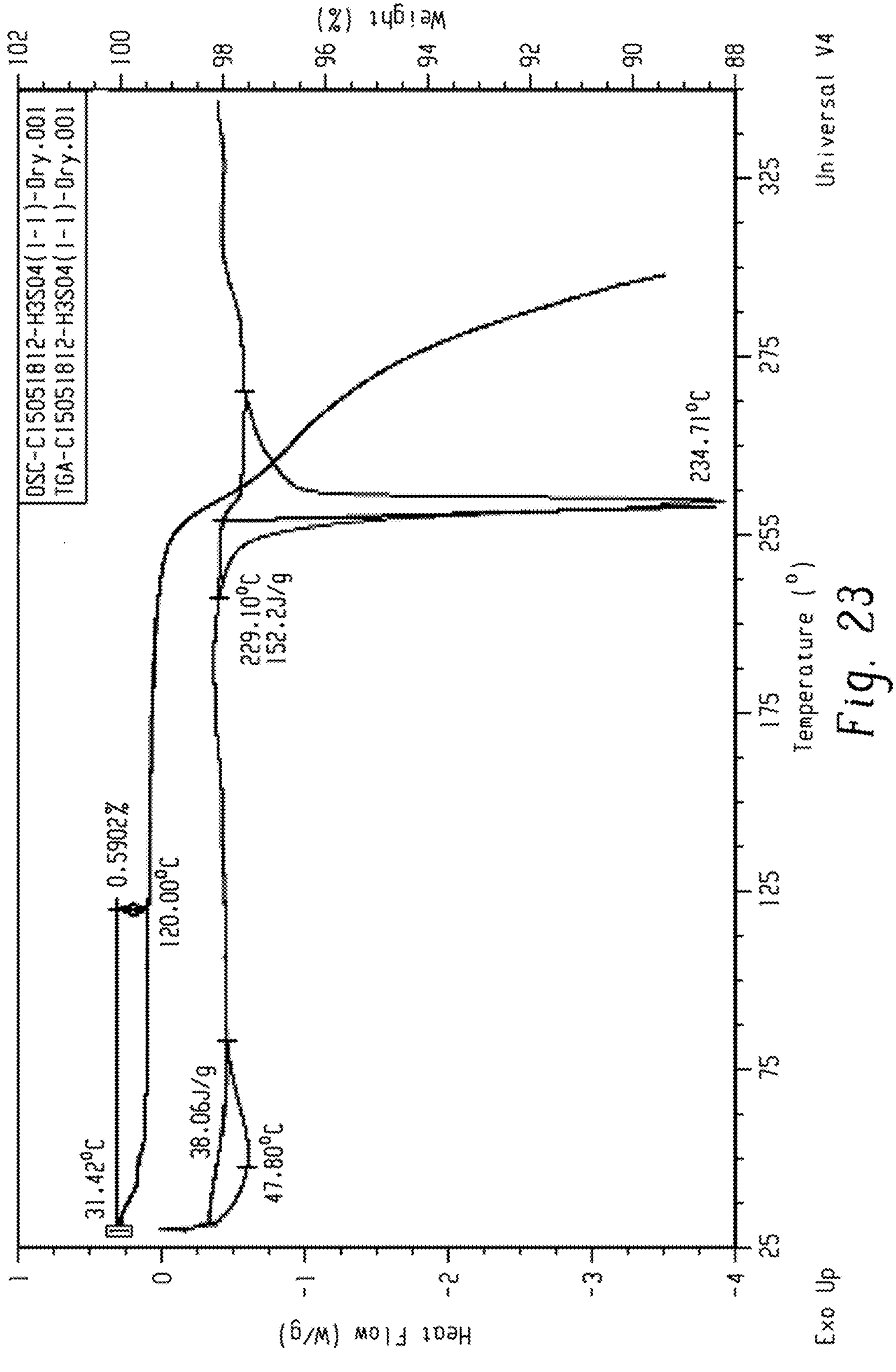
FIG. 23 shows the TGA and DSC profiles of Compound 1•$H_3PO_4$ (1:1; Form A).

In one embodiment, the crystalline phosphate salt of Compound 1 (crystalline Form A) is characterized by a TGA profile substantially as shown in FIG. 23.

In one embodiment, the crystalline phosphate salt of Compound 1 (crystalline Form A) is characterized by a melting point having an onset temperature of 229.1° C.

In one embodiment, the crystalline phosphate salt of Compound 1 (crystalline Form A) is characterized by a DSC profile substantially as shown in FIG. 23.

In one embodiment, the crystalline phosphate salt of Compound 1 (crystalline Form A) is characterized by a DSC profile having peaks at about 47.8° C. and 234.7° C.

Figure 24A:
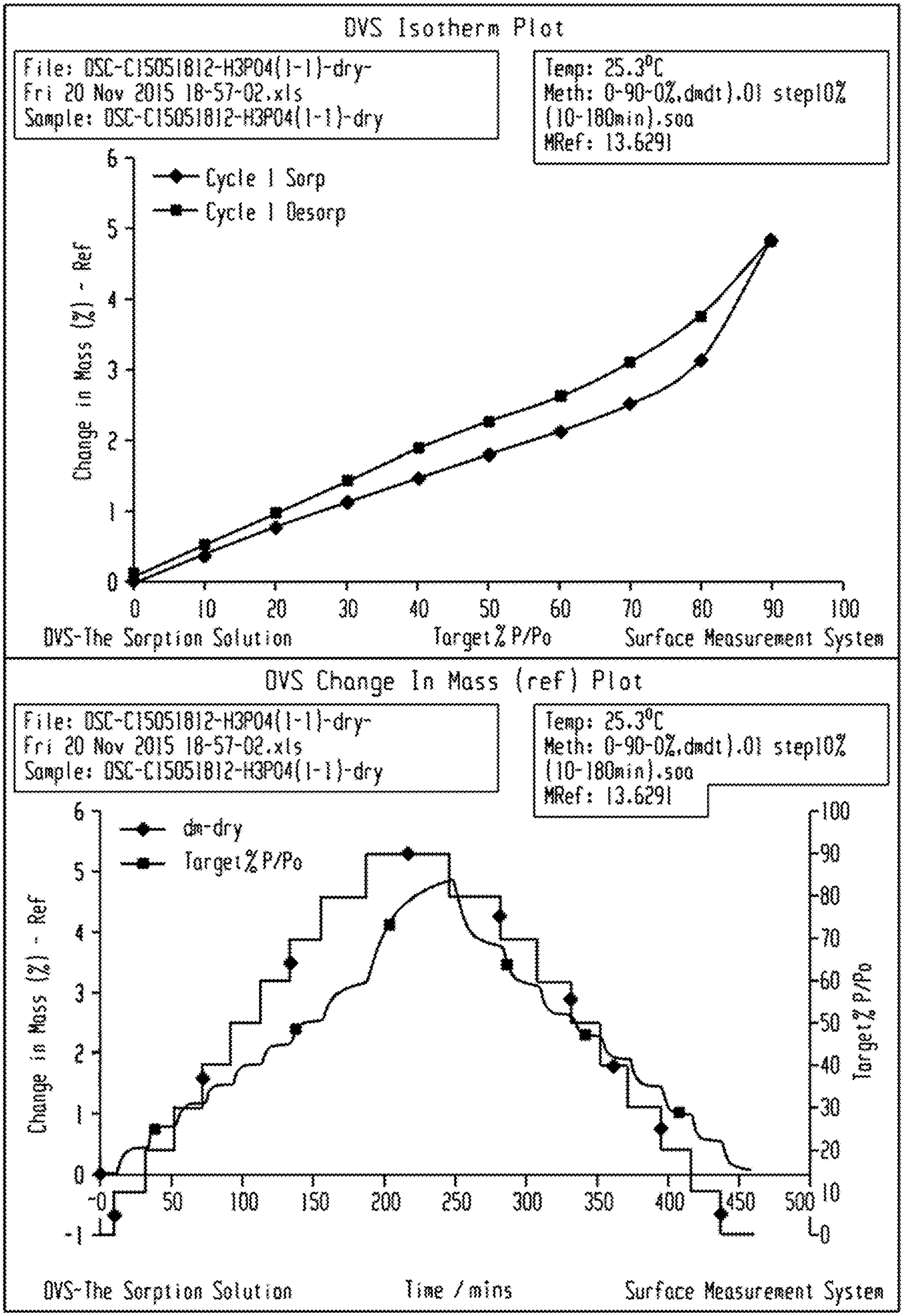
FIG. 24 and 24B show the DVS isotherm analysis of Compound 1 $H_3PO_4$ (1:1; Form A).

In one embodiment, the crystalline phosphate salt of Compound 1 (crystalline Form A) is characterized by a dynamic vapor sorption isotherm substantially as shown in FIG. 24.

In another aspect, the present invention provides a method of preparing the crystalline phosphate (Form A) salt of Compound 1, comprising:

(a) adding a solution of $H_3PO_4$/methanol to a mixture of the compound of Formula 1 (Form A, not limiting) in methanol;

(b) stirring for about 24 hours at about room temperature; and (c) isolating the resulting crystalline $H_3PO_4$ salt of the Compound 1.

In one embodiment, the present invention provides a crystalline tosylate salt of N-(5-((4-ethylpiperazin-yl)methyl)pyridin-2-yl-5-fluoro-4-(3-isopropyl-2-methyl-2H-indazol-5-yl)pyrimidin-2-amine.

In one embodiment, the crystalline tosylate salt comprises a molar ratio of N-(5-((4-ethylpiperazin-1-yl)methyl)pyridin-2-yl-5-fluoro-4-(3-isopropyl-2-methyl-2H-indazol-5-yl)pyrimidin-2-amine to tosylate of 1:1.

In one embodiment, the crystalline tosylate salt of Compound 1 (crystalline Form A) has an X-ray powder diffraction pattern comprising characteristic peaks at diffraction angles 2θ of approximately 7.4°, 9.8°, 14.7°, 18.4°, 19.5°, and 28.0°, each ±0.2°.

Figure 28:
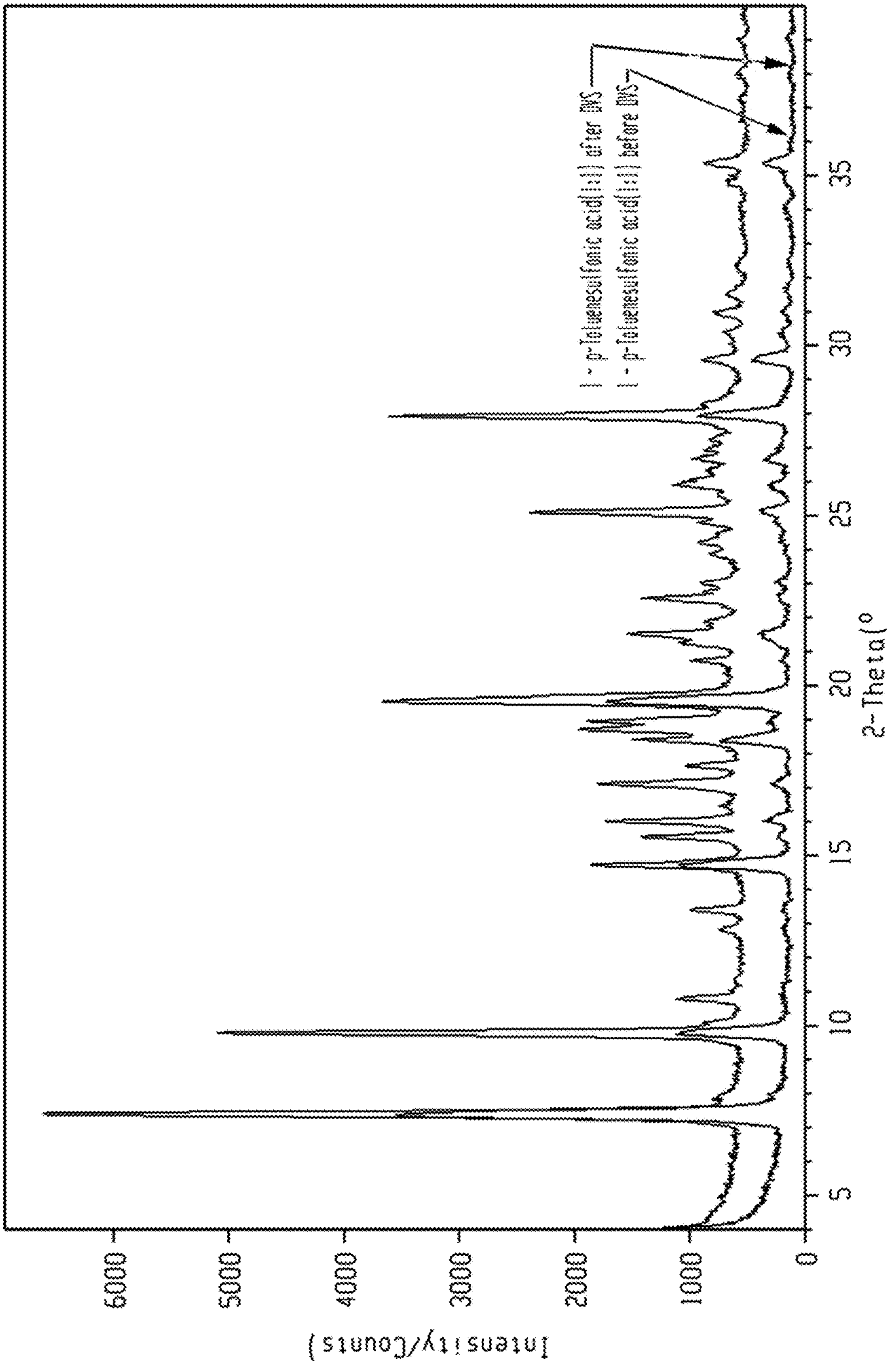
FIG. 28 shows the X-ray powder diffraction patterns of Compound 1 •p-toluenesulfonic acid (1:1; Form A) before and after DVS.
Figure 29:
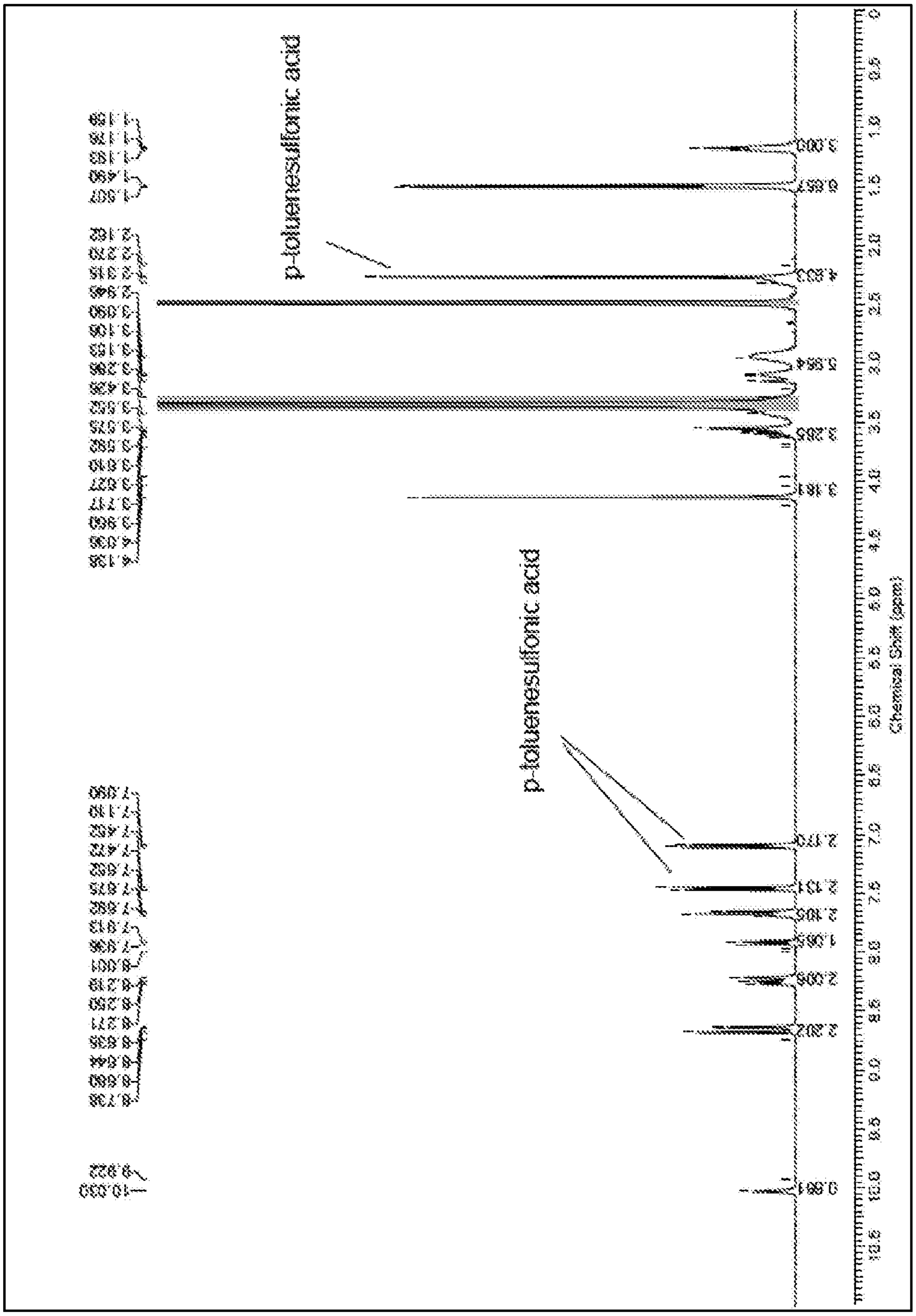
FIG. 29 shows the 400 MHz 1H NMR characterization for 1•p-toluenesulfonic acid (1:1; Form A) in DMSO-d6.

In one embodiment, the X-ray powder diffraction pattern of the tosylate salt of Compound 1 in crystalline Form A is substantially as shown in FIG. 28.

Figure 26:
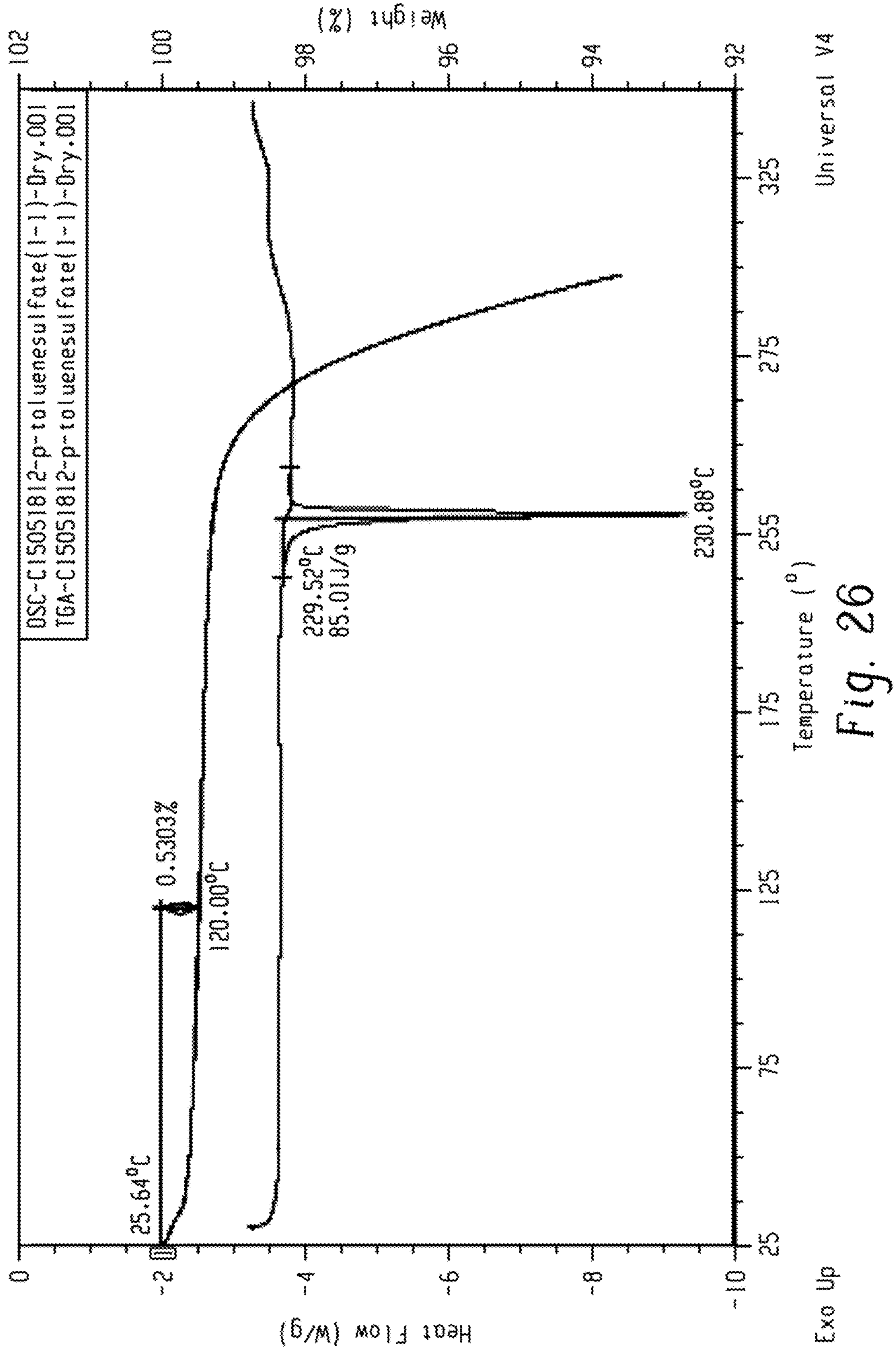
FIG. 26 shows the TGA and DSC profiles of Compound 1•p-toluenesulfonic acid (1:1; Form A).

In one embodiment, the crystalline tosylate salt of Compound 1 (crystalline Form A) is characterized by a TGA profile substantially as shown in FIG. 26.

In one embodiment, the crystalline tosylate salt of Compound 1 (crystalline Form A) is characterized by a DSC profile substantially as shown in FIG. 26.

In one embodiment, the crystalline tosylate salt of Compound 1 (crystalline Form A) is characterized by a DSC profile having a peak at about 230.9° C.

In one embodiment, the crystalline tosyalte salt of Compound 1 (crystalline Form A) is characterized by a melting point having an onset temperature of about 229.5° C.

Figure 27A:
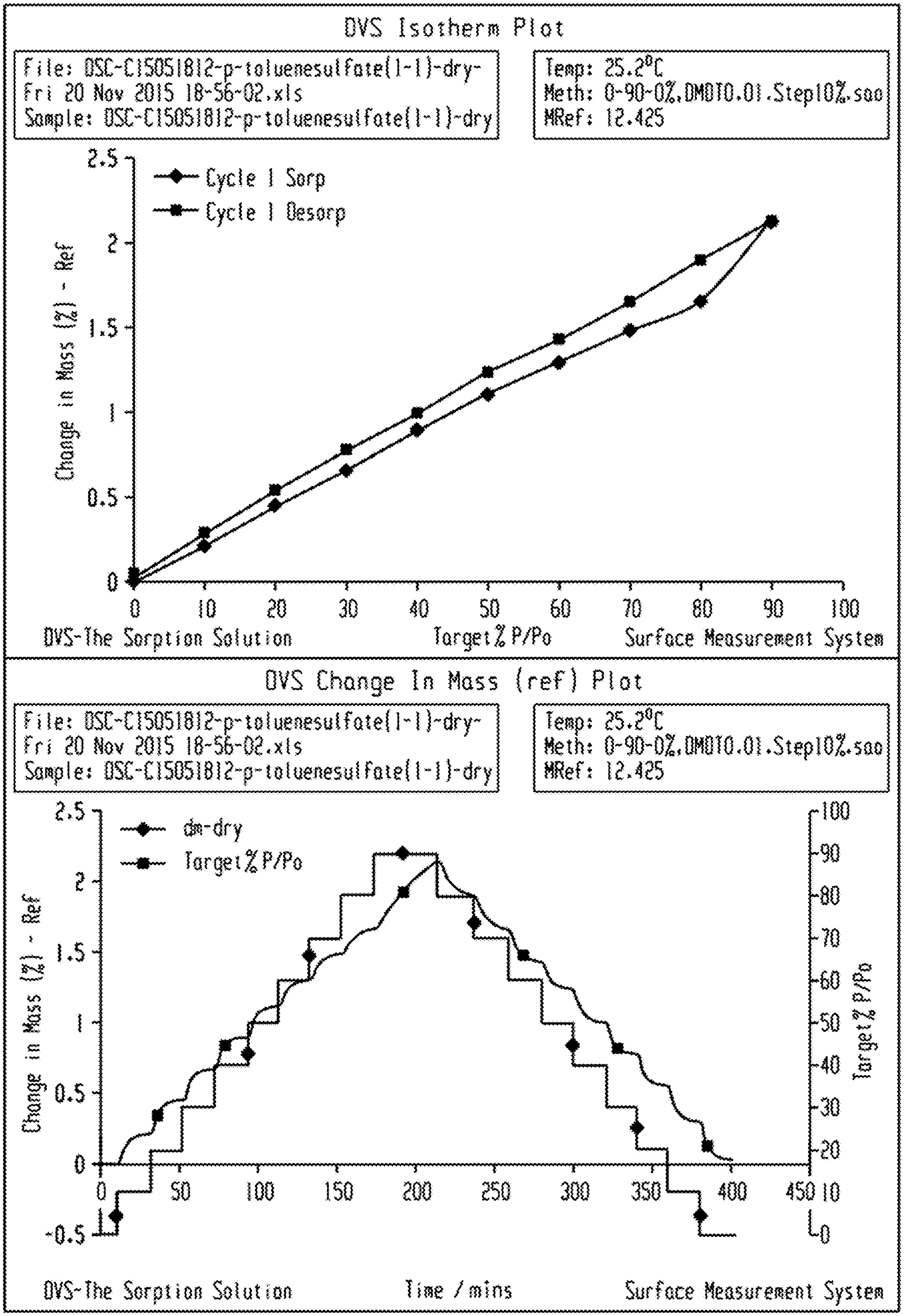

In one embodiment, the crystalline tosylate salt of Compound 1 (crystalline Form A) is characterized by a dynamic vapor sorption isotherm substantially as shown in FIG. 27.

Figure 39:
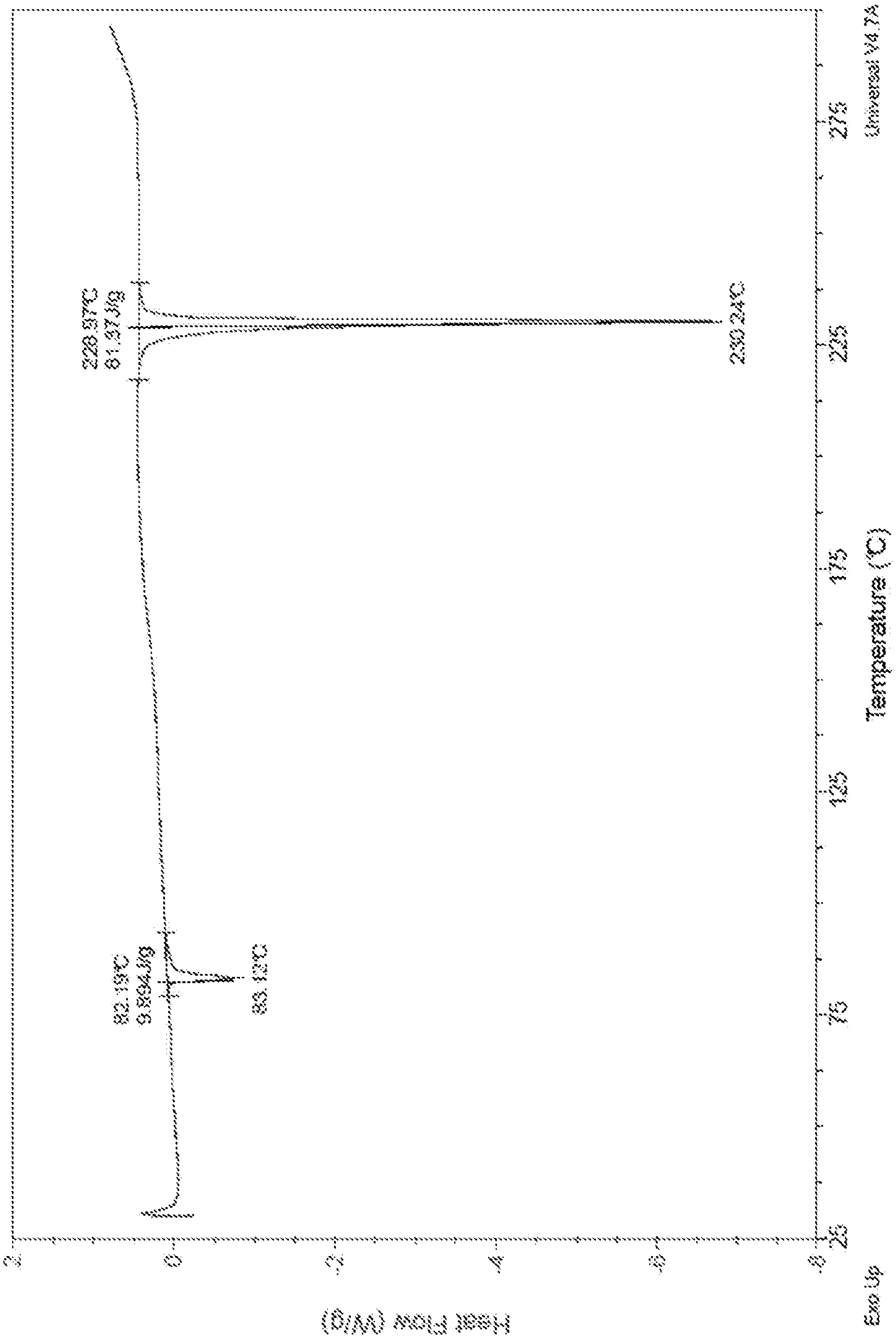
FIG. 39 shows the DSC profile of Compound 1•p-toluenesulfonic acid (1:1; Form B).

In another embodiment, the present invention provides a crystalline tosyalte salt of Compound 1 (crystalline Form B) characterized by a DSC profile substantially as shown in FIG. 39.

In one embodiment, the crystalline tosylate salt of Compound 1 (crystalline Form B) is characterized by (a) an X-ray powder diffraction pattern comprising any three (3) of characteristic peaks at diffraction angles 2θ of approximately 7.8°, 10.0°, 15.7°, 16.9°, 19.7°, and 20.6°; and/or (b) a DSC profile having peaks at 82.2° C. and 229.0° C.

The present invention also provides a method of preparing the crystalline p-toluenesulfonic acid (Form A) salt of Compound 1 comprising:

(a) adding a solution of p-toluenesulfonic acid/methanol to a mixture of the compound of Formula 1 (Form A, not limiting) in methanol;

(b) stirring for about 24 hours at about room temperature; and (c) isolating the resulting crystalline p-toluenesulfonic acid salt of the compound 1.

In one embodiment, the present invention provides a crystalline methanesulfonic acid salt of N-(5-((4-Ethylpiperazin-yl)methyl)pyridin-2-yl-5-fluoro-4-(3-isopropyl-2-methyl-2H-indazol-5-yl)pyrimidin-2-amine.

In one embodiment, the crystalline methanesulfonic acid salt has a molar ratio of crystalline N-(5-((4-Ethylpiperazin-yl)methyl)pyridin-2-yl-5-fluoro-4-(3-isopropyl-2-methyl-2H-indazol-5-yl)pyrimidin-2-amine to tosylate of 1:2.

Figure 31:
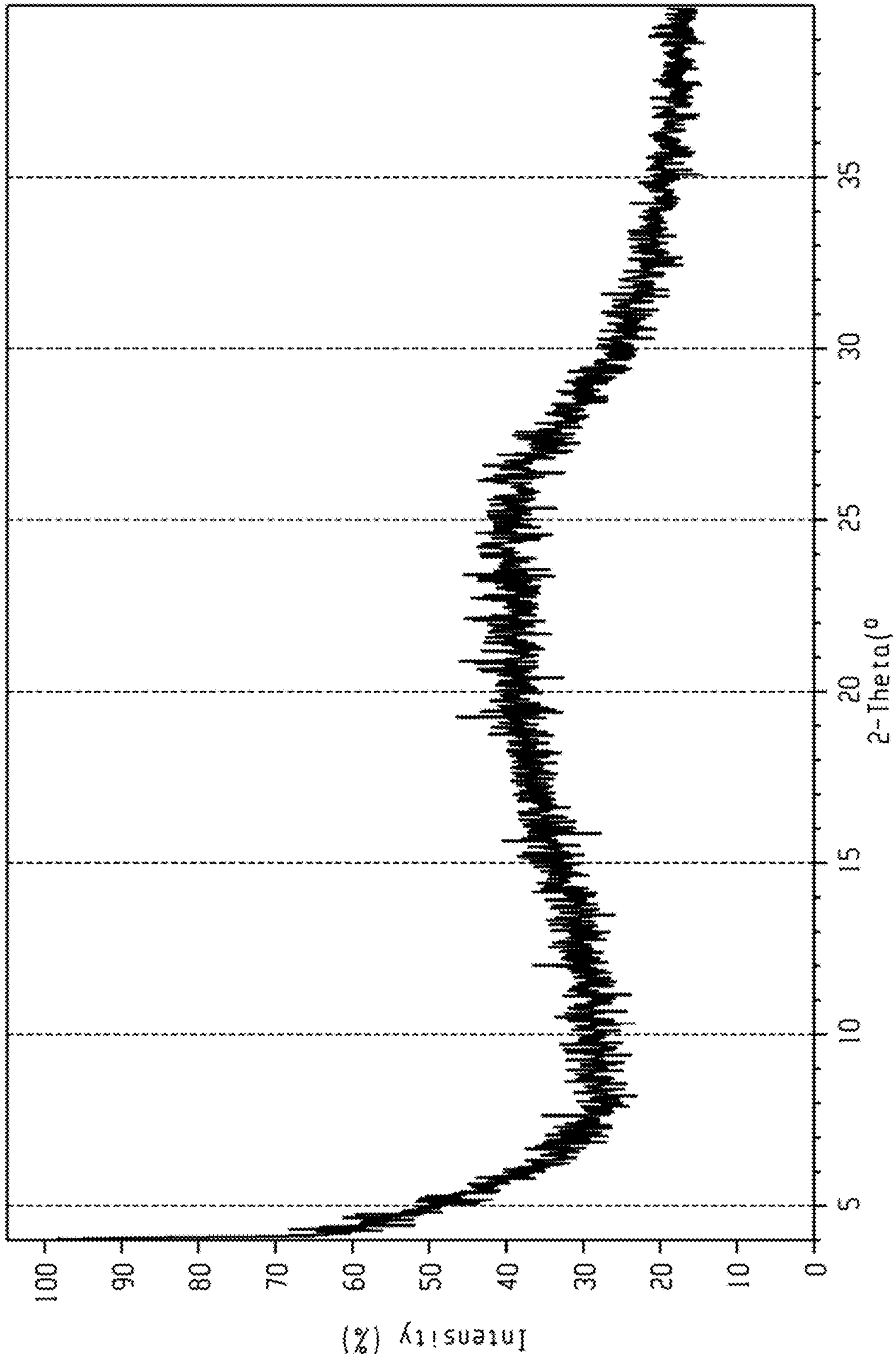
FIG. 31 shows the X-ray powder diffraction pattern of the dry sample of Compound 1•methanesulfonic acid (1:2; Form A).

In one embodiment, the X-ray powder diffraction pattern of the mesylate salt of Compound 1 comprising the Compound 1 and mesylate in about 1:2 molar ratio in crystalline Form A is substantially as shown in FIG. 31.

Figure 30:
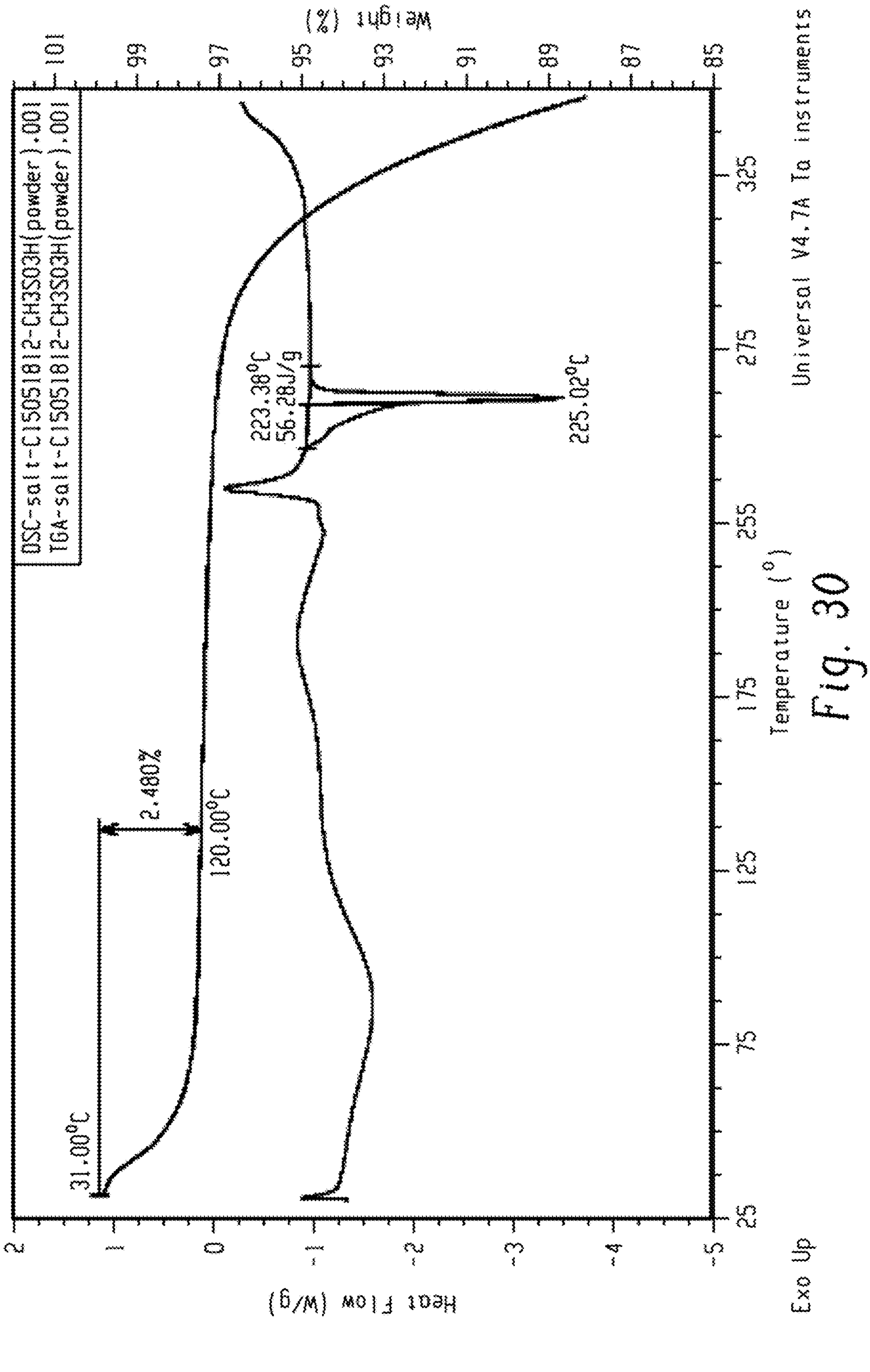
FIG. 30 shows the TGA and DSC profiles of Compound 1 methanesulfonic acid (1:2; Form A).

In one embodiment, the crystalline methanesulfonic acid salt of Compound 1 comprising the Compound 1 and mesylate in about 1:2 molar ratio in crystalline Form A is characterized by a TGA profile substantially as shown in FIG. 30.

In one embodiment, the crystalline methanesulfonic acid salt of Compound 1 comprising the Compound 1 and mesylate in about 1:2 molar ratio in crystalline Form A is characterized by a DSC profile substantially as shown in FIG. 30.

In one embodiment, the crystalline methanesulfonic acid salt of Compound 1 comprising the Compound 1 and mesylate in about 1:2 molar ratio in crystalline Form A is characterized by a DSC profile having a peak at about 225.0° C.

In one embodiment, the cystalline methanesulfonic acid salt of Compound 1 comprising the Compound 1 and mesylate in about 1:2 molar ratio in crystalline Form A is characterized by a melting point having an onset temperature of about 223.4° C.

In another embodiment, the present invention provides a method of preparing the crystalline methanesulfonic acid of Compound 1 comprising the Compound 1 and mesylate in about 1:2 molar ratio (Form A) salt of Compound 1, comprising:

(a) adding a solution of methanesulfonic acid/methanol to a mixture of the compound of Formula 1 (Form A, not limiting) in methanol;

(b) stirring for about 24 hours at about room temperature; and (c) isolating the resulting crystalline methanesulfonic acid salt of the compound 1.

In another aspect, the present invention provides methods of preparing solid amorphous forms of Compound 1 and salts thereof, in particular the HCl, $H_2SO_4$, $H_3PO_4$, methanesulfonic acid, and p-toluenesulfonic acid salts disclosed herein.

In one embodiment, the present invention provides a solid amorphous form of N-(5-((4-Ethylpiperazin-yl)methyl)pyridin-2-yl-5-fluoro-4-(3-isopropyl-2-methyl-2H-indazol-5-yl)pyrimidin-2-amine sulfate.

In one embodiment, the solid amorphous form of N-(5-((4-Ethylpiperazin-yl)methyl)pyridin-2-yl-5-fluoro-4-(3-isopropyl-2-methyl-2H-indazol-5-yl)pyrimidin-2-amine sulfate has a molar ratio of N-(5-((4-Ethylpiperazin-yl)methyl)pyridin-2-yl-5-fluoro-4-(3-isopropyl-2-methyl-2H-indazol-5-yl)pyrimidin-2-amine to sulfate of 1:1.

In one embodiment, the solid amorphous form of N-(5-((4-Ethylpiperazin-yl)methyl)pyridin-2-yl-5-fluoro-4-(3-isopropyl-2-methyl-2H-indazol-5-yl)pyrimidin-2-amine sulfate has a molar ratio of N-(5-((4-Ethylpiperazin-yl)methyl)pyridin-2-yl-5-fluoro-4-(3-isopropyl-2-methyl-2H-indazol-5-yl)pyrimidin-2-amine to sulfate of 2:1.

In one embodiment, the present invention provides a method for preparing an amorphous sulfate salt of the compound 1, comprising:

(a) adding a solution of $H_2SO_4$ acid/methanol to a mixture of the compound of Formula 1 (Form A, not limiting) in methanol;

(b) stirring for about 24 hours at about room temperature; and (c) isolating the resulting amorphous $H_2SO_4$ acid salt of the compound 1.

In one embodiment, the present invention provides a solid amorphous form of N-(5-((4-ethylpiperazin-1-yl)methyl)pyridin-2-yl-5-fluoro-4-(3-isopropyl-2-methyl-2H-indazol-5-yl)pyrimidin-2-amine methanesulfonate.

In one embodiment, the solid amorphous form of N-(5-((4-ethylpiperazin-1-yl)methyl)pyridin-2-yl-5-fluoro-4-(3-isopropyl-2-methyl-2H-indazol-5-yl)pyrimidin-2-amine methanesulfonate has a molar ratio of N-(5-((4-ethylpiperazin-yl)methyl)pyridin-2-yl-5-fluoro-4-(3-isopropyl-2-methyl-2H-indazol-5-yl)pyrimidin-2-amine to methanesulfonate of 1:1.

In another embodiment, the present invention provides a method for preparing an amorphous methanesulfonic acid salt of the compound 1, comprising:

(a) adding a solution of methane sulfonic acid/methanol to a mixture of the compound of Formula 1 (Form A) in methanol;

(b) stirring for about 24 hours at about room temperature; and (c) isolating the resulting amorphous methane sulfonic acid salt of the compound 1.

All the crystalline polymorphs of the present invention are substantially pure.

The term "substantially pure" as herein used refers to at least 85 wt %, preferably at least 95 wt %, more preferably at least 99 wt % of the compound of Formula 1, or a salt thereof, exists in a crystal form of the present invention, particularly in the crystal forms of Form A, Form B, Form C, Form D, Form E, and Form F.

The main peaks described in X-ray powder diffraction (XRPD) pattern of the crystalline polymorphs above are reproducible and are within the error limit (the specified value ±0.2° for a 2θ or 2-theta value), for example, whether a term "about" or "approximately" is used as modification word, a 2θ value of 11.5 would indicate that the peak has a value within the range of 11.3° to 11.7°, or the like.

Figure 1:
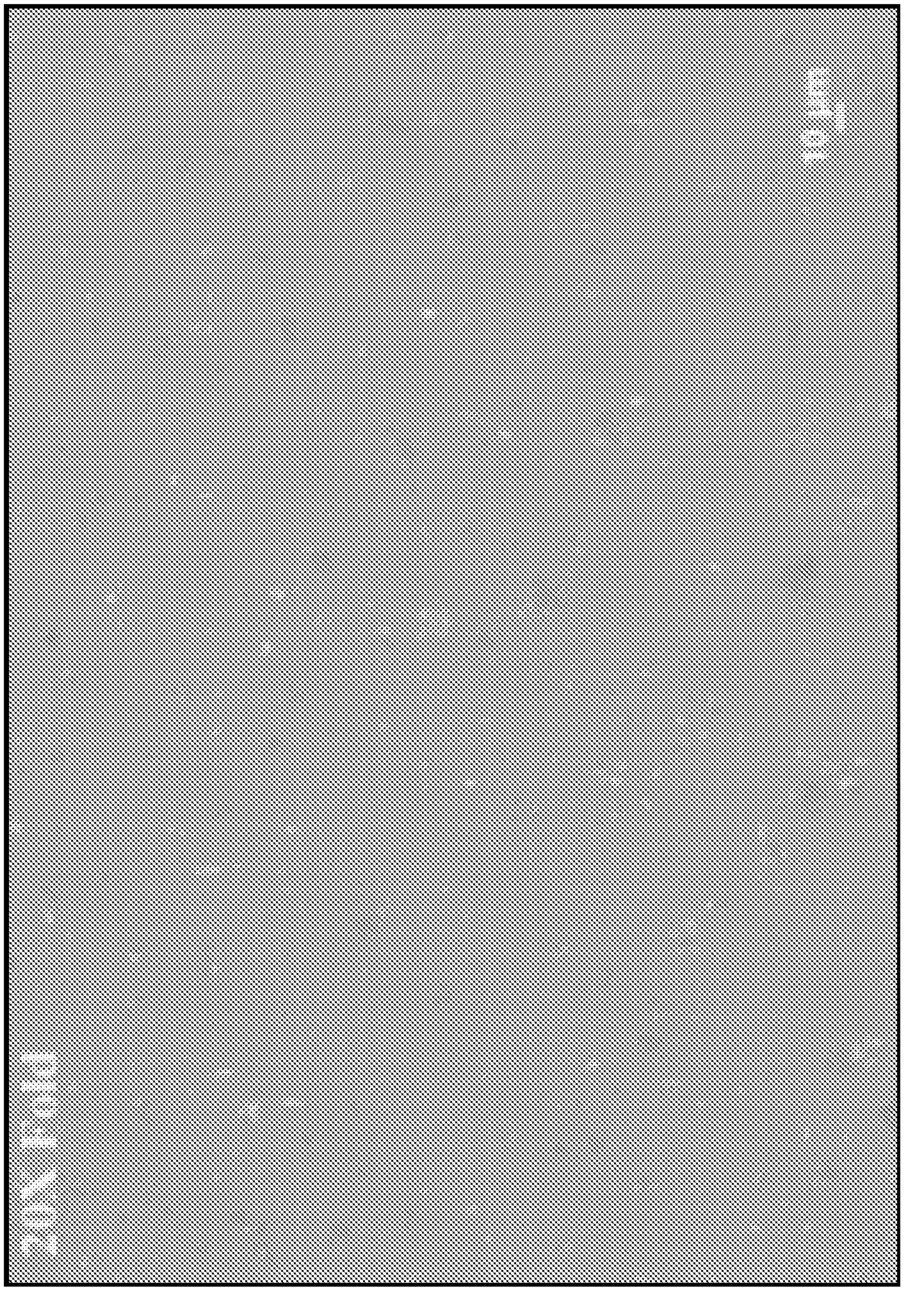
FIG. 1 shows the PLM image of the freebase of Compound 1 (Form A) raw material.

In the present invention, "the X-ray powder diffraction pattern shown as in FIG. 2A" refers to the X-ray powder diffraction pattern that show major peaks as in FIG. 2A, wherein major peaks refer to those with the relative intensity greater than 10%, preferably greater than 30%, relative to the highest peak (with its relative intensity designated to be 100%) in FIG. 1. Likewise, in the present invention, the X-ray powder diffraction pattern shown as in FIG. 10, 11, 12, 13, 14, 18, 22, 25, 28, 31, 33, 34, 35, 36, 37 or 38, refers to the X-ray powder diffraction pattern that show major peaks as in FIG. 10, 11, 12, 13, 14, 18, 22, 25, 28, 31, 33, 34, 35, 36, 37 or 38, wherein major peaks refer to those with the relative intensity greater than 10%, preferably greater than 30%, relative to the highest peak (with its relative intensity designated to be 100%) in FIG. 10, 11, 12, 13, 14, 18, 22, 25, 28, 31, 33, 34, 35, 36, 37 or 38, respectively.

The present invention also provides a method of preparing Crystalline Form A, Crystalline Form B, Crystalline Form C, Crystalline Form D, Crystalline Form E, and Crystalline Form F. Crystallizing the compound of the present invention from a suitable solvent system comprising at least one solvent, can be achieved by methods of spontaneous precipitation (evaporation), cooling, and/or adding anti-solvent (in which the compound of the present invention has relatively lower solubility), in order to achieve oversaturation in solvent system.

The present invention also provides a method of preparing salt forms of Compound 1, wherein the salt can be the HCl, $H_2SO_4$, $H_3PO_4$, methanesulfonic acid or p-toluenesulfonic acid salt.

Crystallization also can be achieved by using or not using crystal seeds that are suitable for crystallizing the compound of the present invention.

The present invention also provides a method of preparing the compound of Formula, as follows:

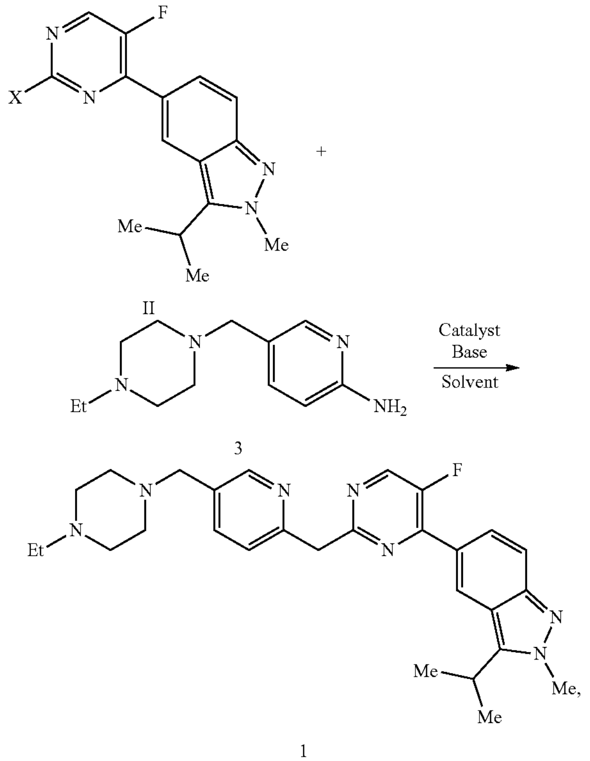

II + 3 → 1 wherein X is halogen, preferably Br or Cl.

In one embodiment, the method of preparing the crystalline form A of the Compound 1 comprises the steps of: (a) reacting a compound of Formula II with the compound of formula 3 in the present of a catalyst to obtain a reaction mixture comprising Compound 1; (b) working up the reaction mixture and isolating a crude product of Compound 1; (c) dissolving the crude product of Compound 1 an aqueous HCl solution and washing the aqueous solution with an ester; and (d) basifying the aqueous solution with a base to above 7 to precipitate out the freebase of Compound 1; and isolating a product of Compound 1 freebase in Form A.

For a general method to prepare Compound 1, see WO 2016/014904 A1, which is incorporated herein by reference in its entirety for all purposes as if the whole publication were set forth herein. A particular embodiment of the method to prepare Compound 1 in crystalline form A is described in Example 1.

In one embodiment, the method of preparing the crystalline form B of the Compound 1 comprises the steps of: (a) slurrying the compound of Formula 1 freebase in ethanol, isopropanol, or a mixed solvent of ethanol:water (3:1 v/v) at an elevated temperature for a period of time; (b) cooling down the slurry of step (a) to room temperature; and (c) isolating the resulting crystalline form B by filtration; and (d) optionally drying the crystalline form B isolated in the step (c). In one embodiment, the compound of Formula 1 freebased in step (a) is in crystalline Form A. In one embodiment, the elevated temperature is about 50° C.; and in one embodiment, the time of slurring is about 24 hours.

In one embodiment, the method of preparing the crystalline form C of the Compound 1 comprises the steps of: (a) slurrying the compound of Formula 1 freebase in acetone at an elevated temperature for a period of time; (b) cooling down the slurry of step (a) to room temperature; and (c) isolating the resulting crystalline form C by filtration; and (d) optionally drying the crystalline form C isolated in the step (c). In one embodiment, the compound of Formula 1 freebased in step (a) is in crystalline Form A. In one embodiment, the elevated temperature is about 50° C.; and in one embodiment, the time of slurring is about 24 hours.

In one embodiment, the method of preparing the crystalline form D of the Compound 1 comprises the steps of: (a) slurrying the compound of Formula 1 freebase in acetone at room temperature for a period of time; (b) isolating the resulting crystalline form D by filtration; and (c) optionally drying the crystalline form D isolated in the step (c). In one embodiment, the compound of Formula 1 freebased in step (a) is in crystalline Form A. In one embodiment, the time of slurring is about 24 hours.

In one embodiment, the method of preparing the crystalline hydrochloride salt of Compound 1 in Form A, comprising the steps of: (a) stirring a mixture of the compound of Formula 1 freebase (Form A) and HCl in methanol at room temperature for a period of time to obtain a slurry comprising the crystalline hydrochloride salt in Form A; and (b) isolating the resulting crystalline HCl salt of the compound of Formula 1 in Form A.

In one embodiment, the method of preparing the crystalline sulfate salt of Compound 1 in Form A, comprising the steps of: (a) stirring a mixture of the compound of Formula 1 freebase (Form A) and sulfuric acid ($H_2SO_4$) in methanol at room temperature to obtain a slurry comprising the crystalline sulfate salt in Form A; (b) isolating the resulting crystalline $H_2SO_4$ salt (Form A) of the compound of Formula 1; and (c) optionally drying the crystalline Form A of $H_2SO_4$ salt isolated.

In one embodiment, the method of preparing the crystalline phosphate salt of Compound 1 in Form A, comprising the steps of: (a) stirring a mixture of the compound of Formula 1 freebase (Form A) and phosphoric acid ($H_3PO_4$) in methanol at room temperature to obtain a slurry comprising the crystalline phosphate salt in Form A; (b) isolating the resulting crystalline $H_3PO_4$ salt (Form A) of the compound of Formula 1; and (c) optionally drying the crystalline Form A of $H_3PO_4$ salt isolated.

In one embodiment, the method of preparing the crystalline p-toluenesulfonic acid salt of Compound 1 in Form A, comprising the steps: (a) stirring a mixture of the compound of Formula 1 freebase (Form A) and p-toluenesulfonic acid in methanol at room temperature to obtain a slurry comprising the crystalline p-toluenesulfonic acid salt in Form A; (b) isolating the resulting crystalline p-toluenesulfonic acid salt (Form A) of the compound of Formula 1; and (c) (c) optionally drying the crystalline Form A of p-toluenesulfonic acid salt isolated.

In one embodiment, the method of preparing the crystalline methanesulfonic acid salt of Compound 1 in Form A, comprising the steps of: (a) stirring a mixture of the compound of Formula 1 freebase (Form A) and methanesulfonic acid in methanol at room temperature to obtain a slurry comprising the crystalline methanesulfonic acid salt in Form A; (b) isolating the resulting crystalline methanesulfonic acid salt (Form A) of the compound of Formula 1; and (c) optionally drying the crystalline Form A of methanesulfonic acid salt isolated.

In one embodiment, the method of preparing an amorphous sulfate salt of the compound of Formula 1, comprising the steps of: (a) stirring a mixture of the compound of Formula 1 freebase (Form A) and $H_2SO_4$ acid in about 2:1 molar ratio in an organic solvent (e.g., methanol) at an elevated or room temperature; and (b) removing the solvent (e.g., methanol) by evaporation or centrifugation to dryness to obtain the resulting amorphous $H_2SO_4$ acid salt of the compound of Formula 1 in about 2:1 molar ratio.

In one embodiment, the method of preparing an amorphous sulfate salt of the compound of Formula 1, comprising the steps of: (a) stirring a mixture of the compound of Formula 1 freebase (Form A) and $H_2SO_4$ acid in about 1:1 molar ratio in an organic solvent (e.g., methanol) at an elevated or room temperature; and (b) removing the solvent (e.g., methanol) by evaporation or centrifugation to obtain the resulting amorphous $H_2SO_4$ acid salt of the compound of Formula 1 in about 1:1 molar ratio.

In one embodiment, the method of preparing an amorphous phosphate salt of the compound of Formula 1, comprising the steps of: (a) stirring a mixture of the compound of Formula 1 freebase (Form A) and $H_3PO_4$ acid in about 1:1 molar ratio in an organic solvent (e.g., methanol) at an elevated or room temperature; and (b) removing the solvent (e.g., methanol) by evaporation or centrifugation to obtain the resulting amorphous $H_3PO_4$ acid salt of the compound of Formula 1 in about 1:1 molar ratio.

In one embodiment, the method of preparing an amorphous methanesulfonic acid salt of the compound of Formula 1, comprising the steps of: (a) stirring a mixture of the compound of Formula 1 freebase (Form A) and methanesulfonic acid in about 1:1 molar ratio in an organic solvent (e.g., methanol) at an elevated or room temperature to obtain a clear solution; and (b) removing the solvent (e.g., methanol) by evaporation or centrifugation to dryness to obtain the resulting amorphous methanesulfonic acid salt of the compound of Formula 1 in about 1:1 molar ratio.

The present invention also provides a pharmaceutical composition comprising a therapeutically effective amount of one or more crystalline polymorphs of Crystalline Form A, Crystalline Form B, Crystalline Form C, Crystalline Form D, or Crystalline Form E of the compound of Formula 1, and a pharmaceutically acceptable excipient, adjuvant or carrier.

The present invention also provides a pharmaceutical composition comprising a therapeutically effective amount of one or more salts of the compound of Formula 1, and a pharmaceutically acceptable excipient, adjuvant or carrier. In an embodiment, the pharmaceutical composition is used in an oral administration. In a preferred embodiment, the composition is used in tablets or capsules. Wherein, the pharmaceutical comprises 1 wt %-99 wt % of the crystalline polymorph of claim 1, or more preferably 1 wt %-70 wt % of the crystalline polymorph, or more preferably 1 wt %-30 wt % of Crystalline Form A, Crystalline Form B, Crystalline Form C, Crystalline Form D, or Crystalline Form E of the compound of Formula 1, Further, the present invention provides a method of inhibiting a cyclin-dependent kinase in a subject by administering to the subject a crystalline polymorph of Crystalline Form A, Crystalline Form B, Crystalline Form C, Crystalline Form D, or Crystalline Form E of the compound of Formula 1, or a salt thereof. Preferably, the cyclin-dependent kinase is CDK4 or CDK6.

In another embodiment, the method provides methods of treating or preventing cancer or an inflammation-related condition in a subject by administering to the subject a crystalline polymorph of Crystalline Form A, Crystalline Form B, Crystalline Form C, Crystalline Form D, or Crystalline Form E of the compound of Formula 1.

Further, the present invention also provides method of inhibiting a cyclin-dependent kinase in a subject by administering to the subject a salt of the compound of Formula 1, wherein the salt is selected from the HCl, $H_2SO_4$, $H_3PO_4$, methanesulfonic acid and p-toluenesulfonic acid salt.

In one embodiment, the method provides a method of treating a CDK4 or CDk6-associated inflammation or cancer, wherein the cancer is selected from the group consisting of brain cancer, metastatic brain cancer, squamous cell cancer, bladder cancer, gastric cancer, pancreatic cancer, hepatic cancer, glioblastoma multiforme breast cancer, head cancer, neck cancer, esophageal cancer, prostate cancer, colorectal cancer, lung cancer, renal cancer, kidney cancer, ovarian cancer, gynecological cancer, thyroid cancer, non-small cell lung cancer (NSCLC), refractory ovarian cancer, or head and neck cancer. In a particular embodiment, the cancer is a glioblastoma or metastatic brain cancer.

In another aspect, the invention provides use of any of the crystalline or amorphous forms of the compound of Formula I or a pharmaceutically acceptable salt thereof in the manufacture of a medicament for the treatment of a CDK4 or CDk6-associated inflammation or cancer, wherein the cancer is selected from the group consisting of brain cancer, metastatic brain cancer, squamous cell cancer, bladder cancer, gastric cancer, pancreatic cancer, hepatic cancer, glioblastoma multiforme breast cancer, head cancer, neck cancer, esophageal cancer, prostate cancer, colorectal cancer, lung cancer, renal cancer, kidney cancer, ovarian cancer, gynecological cancer, thyroid cancer, non-small cell lung cancer (NSCLC), refractory ovarian cancer, or head and neck cancer. In a particular embodiment, the cancer is a glioblastoma or metastatic brain cancer.

The terms in the present invention, if not specifically defined, take their ordinary meanings as would be understood by those skilled in the art.

For example, the term "alcohol," "alcoholic solvent," or the like, refers to C1-C6 alkyl alcohol, preferably C1-C4 alkyl alcohol, for example, in some embodiments preferably, methanol, ethanol, isopropanol, or the like.

The term "ketone," "alkylketone," or the like, refers to C3-C7 alkanone, having a formula RCOR', wherein R and R' are each independently C1-C4 alkyl, for example, in some embodiments preferably, acetone, butanone, 2-pentanone, 3-pentanone, methyl isobutyl ketone (MIBK), or the like.

The term "ester," or the like, refers to a lower alkyl aliphatic acid ester having a formula RCOOR', wherein R and R' are each independently C1-C4 alkyls, for example, in some embodiments preferably, ethyl acetate, ethyl propionate, methyl acetate, propyl acetate, ispropyl acetate, or the like.

The term "ether," or the like, refers to a lower alkyl ether or cyclic ether (each alkyl having 1 to 4 carbon atoms), including but not limited to diethyl ether, di-isopropyl ether, ethyl propyl ether, methyl t-butyl ether (MTBE), tetrahydrofuran (THF), 1,4-dioxane, or the like.

The term "aromatic hydrocarbon," or the like, refers to benzene optionally substituted by 1 to 3 methyl or ethyl groups, for example, in some embodiments preferably, toluene, 1,2-xylene, 1,4-xylene, 1,3-xylene, cumene, ethylbenzene, or the like.

The term "halogenated hydrocarbon," or the like, refers to C1-C6 alkane substituted by one to six, preferably one to four, F and/or Cl atoms, for example, in some embodiments preferably, dichloromethane, chloroform, 1,1,1-trifluoroethane, or the like. The term "nitrile," "nitrile solvent," or the like, refers to C2-C4 alkyl nitrile, i.e., $CH_3CN$, $CH_3CH_2CN$, $CH_3CH_2CH_2CN$, or $CH_3CH(CN)CH_3$, preferably $CH_3CN$.

The term "room temperature", as used herein, unless otherwise noted, means a temperature in the range of about 20 to about 25° C., with an average of about 23° C.

Any of the crystalline or amorphous forms, especially the former, of the Compound free base or a salt thereof may exist in a solvate form, which can be readily determined by those skilled in the art through various conventional analytical methods. Such solid forms of solvates are encompassed by the present invention.

The term "solvate," as used herein, means a physical association of a compound of this invention with a stoichiometric or non-stoichiometric amount of solvent molecules. For example, one molecule of the compound associates with one or more, preferably one to three, solvent molecules. It is also possible that multiple (e.g., 1.5 or 2) molecules of the compound share one solvent molecule. This physical association may include hydrogen bonding. In certain instances the solvates will be capable of isolation as crystalline solid. The solvent molecules in the solvate may be present in a regular arrangement and/or a non-ordered arrangement. Exemplary solvates include, but are not limited to, hydrates, ethanolates, methanolates, and isopropanolates. Methods of solvation are generally known in the art.

The term "treatment" or "treating" refers to the management and care of a patient for the purpose of combating the disease, condition or disorder.

The term "therapeutically effective amount" refers to an amount of a drug or a therapeutic agent that will elicit the desired biological and/or medical response of a tissue, system or an animal (including man) that is being sought by a researcher or clinician.

The term "subject" or "patient" refers to a mammalian animal.

The term "mammal" or "mammalian animal" includes, but is not limited to, humans, dogs, cats, horses, pigs, cows, monkeys, rabbits and mice. The preferred mammals are humans.

The term "administering" means applying a compound of the invention, or a pharmaceutically acceptable salt, prodrug or composition thereof, to a subject in need of treatment. The administration of the composition of the present invention in order to practice the present methods of therapy is carried out by administering a therapeutically effective amount of the compounds in the composition to a subject in need of such treatment or prophylaxis. The need for a prophylactic administration according to the methods of the present invention is determined via the use of well-known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgment.

The term "pharmaceutically acceptable", as used herein, refers to those compounds, materials, compositions and/or dosage forms, which are, within the scope of sound medical judgment, suitable for contact with the tissues of mammals, especially humans, without excessive toxicity, irritation, allergic response and other problem complications commensurate with a reasonable benefit/risk ratio.

The term "therapeutically effective amount" as herein used, refers to the amount of a compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In the case of combination therapy, the "therapeutically effective amount" refers to the total amount of the combination objects for the effective treatment of a disease, a disorder or a condition.

The pharmaceutical composition comprising the compound of the present invention can be administrated via oral, inhalation, rectal, parenteral or topical administration to a subject who needs treatment. For oral administration, the pharmaceutical composition may be a regular solid formulation such as tablets, powder, granule, capsules and the like, a liquid formulation such as water or oil suspension or other liquid formulation such as syrup, solution, suspension or the like; for parenteral administration, the pharmaceutical composition may be solution, water solution, oil suspension concentrate, lyophilized powder or the like. In one embodiment, the formulation of the pharmaceutical composition is selected from tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All formulations of the pharmaceutical composition of the present invention can be produced by the conventional methods in the pharmaceutical field. For example, the active ingredient can be mixed with one or more excipients, then to make the desired formulation. The "pharmaceutically acceptable carrier" refers to conventional pharmaceutical carriers suitable for the desired pharmaceutical formulation, for example: a diluent, a vehicle such as water, various organic solvents, etc, a filler such as starch, sucrose, etc; a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such, as talc, calcium, stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, aromatics, a sweetener, and a dye. In one embodiment, the excipient is suitable for desired formulation and administration type. The term "disease" or "disorder" or "condition" refers to any disease, discomfort, illness, symptoms or indications.

It is noted here that, as used in this specification and the appended claims, the singular forms "a," "an," and "the" include plural reference unless the context clearly dictates otherwise. In general, when either a singular or a plural form of a noun is used, it denotes both singular and plural forms of the noun.

The term "about" or "approximately", unless otherwise defined, generally includes up to plus or minus 10% of the indicated number. For example, "about 10%" may indicate a range of 9% to 11%, and "about 20" may mean from 18 to 22. Preferably "about" includes up to plus or minus 6% of the indicated value. Alternatively, "about" includes up to plus or minus 5% of the indicated value. Other meanings of "about" may be apparent from the context, such as rounding off, so, for example "about 1" may also mean from 0.5 to 1.4.

However, in the case of a melting or onset temperature of a crystalline form as measured by in a DSC thermogram, the term "about" may indicate that the melting or onset temperature can usually vary within ±2° C., regardless of the absolute value of the melting or onset temperature, as a person skilled in the art would understand it. As would be understood by a person skilled in the art, when a parameter is not critical, a number is often given only for illustration purpose, instead of being limiting.

The terms "including," "comprising," "containing," or "having" and variations thereof are meant to encompass the items listed thereafter and equivalents thereof as well as additional subject matter unless otherwise noted. The following non-limiting examples further illustrate certain aspects of the present invention.

EXAMPLES

The present invention is further exemplified, but not limited, by the following examples that illustrate the invention. In the examples of the present invention, the techniques or methods, unless expressly stated otherwise, are conventional techniques or methods in the art.

Example 1

Synthesis of Compound 1 (Form A)

Compound 1

N-(5-((4-Ethylpiperazin-yl)methyl)pyridin-2-yl-5-fluoro-4-(3-isopropyl-2-methyl-2H-indazol-5-yl)pyrimidin-2-amine (1)

1

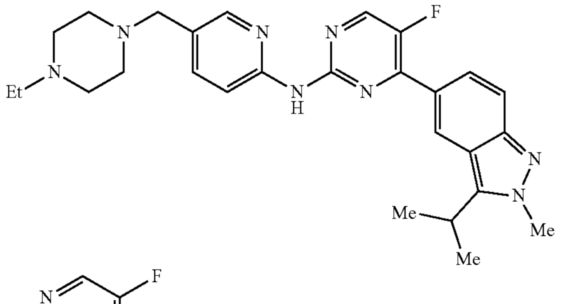

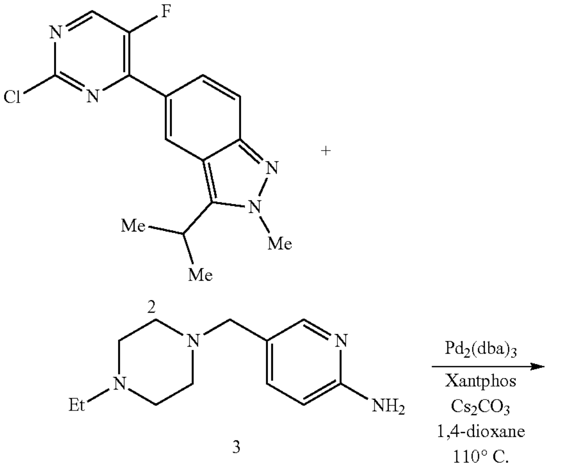

2 3 1

A mixture of 5-(2-chloro-5-fluoropyrimidin-4-yl)-2-methyl-3-(propan-2-yl)-2H-indazole (2), (20.7 mol, 1.0 equiv), 5-((4-ethylpiperazin-1-yl)methylpyridin-2-amine (3) (24.5 mol, 1.2 equiv), $K_3PO_4.3H_2O$ (69.5 mol, 3.4 equiv), $Pd_2(dba)_3$ (0.97 mol, 0.05 equiv) and Xantphos (1.02 mol, 0.05 equiv) in 184 L of 1,4-dioxane was de-gassed with $N_2$ then heated with stirring at 90-100° C. for 24 h. The mixture was cooled to 40-50° C., added to a mixture of L-cysteine (0.05 equiv) and water (6.8 L), and then stirred at 40-50° C. for 3-5 h. The mixture was cooled to 0-10° C. and stirred for 1-3 h, centrifuged, and then washed with fresh water. The wet cake was dissolved in 1N aqueous HCl, washed twice with isopropyl acetate and decolorized with activated carbon. The solution was adjusted to pH 9-10 with 17% aqueous $Na_2CO_3$ and centrifuged. The wet cake was washed three times with water and dried to yield 4.9 kg (47%) of the freebase of 1 (Form A) as an off-white solid (purity: 99.4%); N-(5-((4-ethylpiperazin-yl) methyl) pyridin-2-yl-5-fluoro-4-(3-isopropyl-2-methyl-2H-indazol-5-yl) pyrimidin-2-amine (1). MS m/z MH+489; $^1H$ NMR (300 MHz, $CDCl_3$, ppm): δ 0.97 (t, 3H, J=7.1 Hz), 1.51 (d, 2H, J=7.0 Hz), 2.27-2.51 (overlapping m, 10H), 3.33 (s, 3H), 3.54-3.68 (m, 1H), 4.15 (s, 3H), 7.64-8.71 (overlapping m, 7H), 10.00 (s, 1H).

The freebase of 1 (Form A) was characterized by polarized light microscopy (PLM), X-ray powder diffraction (XRPD), differential scanning calorimetry (DSC) and thermogravimetric analysis (TGA); FIGS. 1-3. It is crystalline with irregular small particles as shown by PLM and XRPD results (FIGS. 1 and 2). The DSC profile (FIG. 3) shows that there are three endothermic peaks and the melting point is at the onset temperature of 162.3° C. (54.5 J/g). The TGA profile indicates that there is 0.64% weight loss from room temperature to 120° C.

XRPD conditions for all samples are listed below:

SCAN: 4.0/39.9779/0.01972/18.6 (sec), Cu (40 kV, 40 mA);

PEAK: Parabolic Filter, Peak-Top=Summit;

NOTE: Intensity=Counts, 2T (0)=0.0(°), Wavelength to Compute d-Spacing=1.54056 A (Cu/K-alpha1).

Example 2

Freebase Polymorph Screening for Compound 1:

The freebase of Compound 1 (Form A) was placed into each of five glass vials followed by the addition of solvent to each vial as described in Table 1. If a clear solution was obtained, then 1 was added until a suspension was formed. Otherwise the suspension was stirred for 24 h at 50° C. The resulting solids were investigated by XRPD and then dried under vacuum at 40° C. overnight. The dried samples were analyzed by XRPD as well. See FIG. 4.

Three new crystalline freebase forms (Forms B, C and D) resulted and are summarized in Table 1. The original Form A was converted to Form B in isopropanol, ethanol and a 3:1 ethanol:water mixture, while it was converted to Form C in acetone. Form D was obtained from methanol.

TABLE 1

Freebase Polymorph Screening of Compound 1 (Form A) with the Slurry Method

| Solvents | Amount 1 (Form A) (mg) | Solvent Volume (mL) | Procedure Method | Temp. (° C.) | Duration Time | Visual Observation | XRPD results Wet | Dry |
|---|---|---|---|---|---|---|---|---|
| Ethanol | 30.1 | 0.3 | Slurry | 50 | 1 day | Many particles | Form B | Form B |
| Isopropanol | 30.7 | 0.3 | Slurry | 50 | 1 day | Many particles | Form B | Form B |
| Acetone | 29.6 | 0.3 | Slurry | 50 | 1 day | Many particles | Form C | Form C |
| EtOH:$H_2O$ (3:1) | 55.2 | 0.2 | Slurry | 50 | 1 day | Many particles | Form B | Form B |
| Methanol | 50.8 | 2.25 | Slurry | RT | 1 day | Many particles | Form D | Form D |

Compound 1 Freebase (Form B)

The freebase of Compound 1 (Form B) was obtained in IPA, or ethanol and ethanol/water at the ratio of 3:1. Three endothermic peaks are found in the DSC profile and the melting point was at the temperature of 165.4° C. The TGA profile shows there is 0.43% weight loss, which is likely due to the release of solvents (FIG. 6).

Compound 1•Freebase (Form C)

The freebase of 1 (Form C) was obtained in acetone. Based upon the TGA and DSC profiles (FIG. 7), the melting point is at the onset temperature of 160.9° C. (103.6 J/g) and it has 0.43% weight loss from room temperature to 120° C.

Compound 1 Freebase (Form D)

The freebase of 1 (Form D) was obtained in methanol. There are three peaks in the DSC profile as shown in FIG. 8. The first peak is at the onset temperature of 55.9° C. (54.6 J/g) with 1.16% weight loss, and the second peak is at onset temperature 118.8° C. (13.2 J/g), which may be related to release of residual solvent. The third peak is at the temperature of 168.4° C. (68.5 J/g). The dynamic vapor sorption (DVS) isotherm analysis (FIG. 9) shows that freebase of 1 (Form D) is hygroscopic (5.13% at 80% RH) and there is no change of crystalline form after DVS (FIG. 10).

Figure 4:
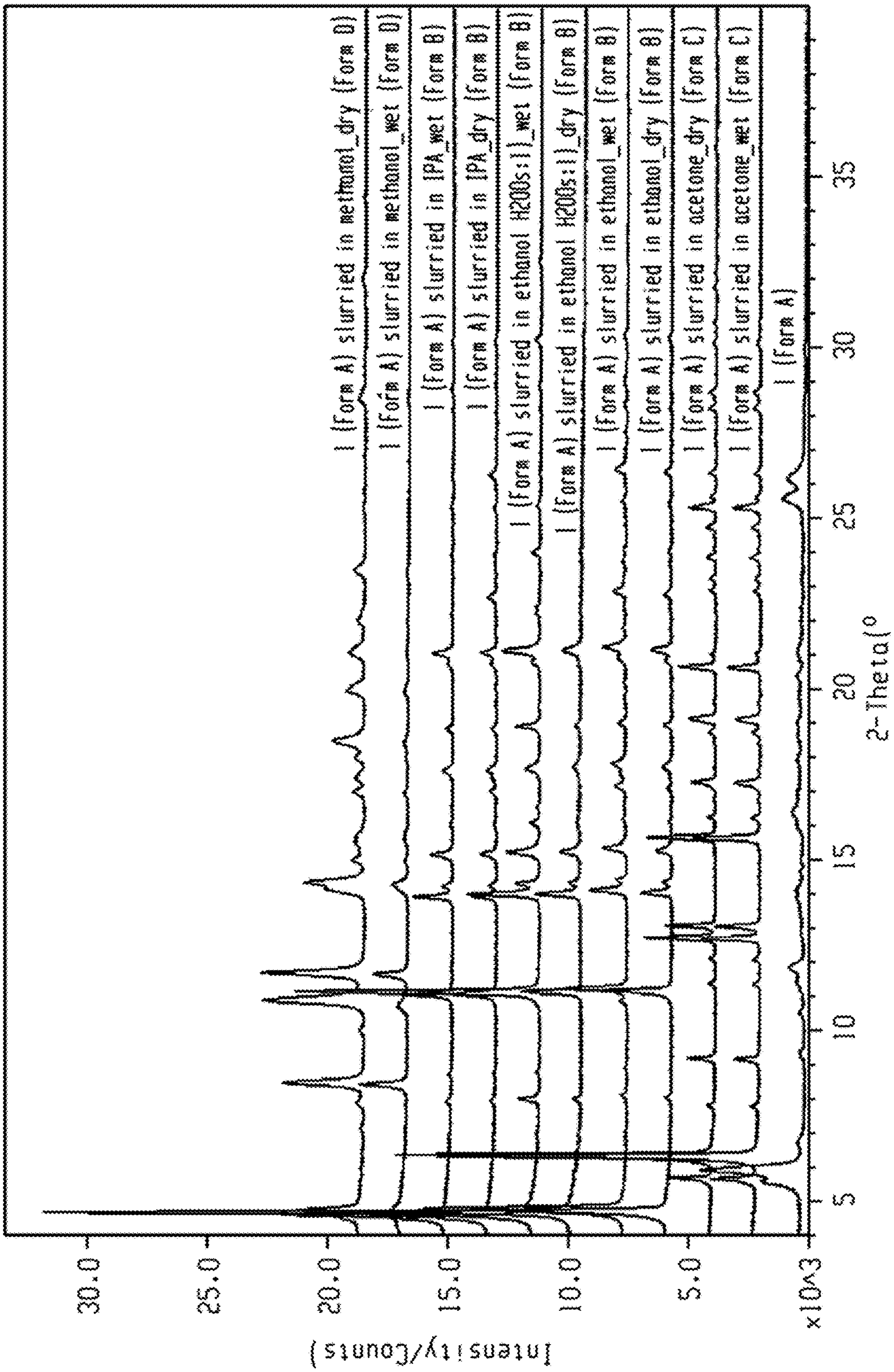
FIG. 4 shows the X-ray powder diffraction pattern of the freebase polymorphs of Compound 1 (Forms A-D).

Selected XRPD data listed in FIG. 4 are listed below.

Form B of Compound 1 Freebase (Dry from IPA):

| | 2-Theta | d(A) | BG | Height | I % |
|---|---|---|---|---|---|
| 1 | 4.631 | 19.0646 | 506 | 5664 | 100.0 |
| 2 | 7.965 | 11.0913 | 212 | 161 | 2.8 |
| 3 | 11.082 | 7.9775 | 168 | 1848 | 32.6 |
| 4 | 13.961 | 6.3379 | 145 | 1018 | 18.0 |
| 5 | 14.276 | 6.1990 | 168 | 251 | 4.4 |
| 6 | 15.184 | 5.8301 | 140 | 674 | 11.9 |
| 7 | 17.035 | 5.2007 | 191 | 193 | 3.4 |
| 8 | 17.415 | 5.0880 | 194 | 129 | 2.3 |
| 9 | 17.630 | 5.0265 | 175 | 387 | 6.8 |
| 10 | 18.869 | 4.6991 | 121 | 212 | 3.7 |
| 11 | 20.748 | 4.2775 | 175 | 220 | 3.9 |
| 12 | 21.100 | 4.2070 | 157 | 604 | 10.7 |
| 13 | 22.701 | 3.9138 | 166 | 320 | 5.6 |
| 14 | 23.957 | 3.7114 | 137 | 86 | 1.5 |
| 15 | 25.340 | 3.5119 | 126 | 111 | 2.0 |
| 16 | 26.288 | 3.3873 | 135 | 287 | 5.1 |
| 17 | 30.158 | 2.9609 | 109 | 94 | 1.7 |

Form C of Compound 1 Freebase (Dry from Acetone):

| # | 2-Theta | d(A) | BG | Height | I % |
|---|---|---|---|---|---|
| 1 | 5.676 | 15.5581 | 357 | 1840 | 17.1 |
| 2 | 6.348 | 13.9124 | 321 | 10743 | 100.0 |
| 3 | 7.803 | 11.3201 | 203 | 289 | 2.7 |
| 4 | 9.187 | 9.6182 | 164 | 1015 | 9.4 |

-continued

| # | 2-Theta | d(A) | BG | Height | I % |
|---|---|---|---|---|---|
| 5 | 11.376 | 7.7717 | 145 | 267 | 2.5 |
| 6 | 12.091 | 7.3136 | 158 | 276 | 2.6 |
| 7 | 12.722 | 6.9526 | 197 | 2339 | 21.8 |
| 8 | 13.074 | 6.7662 | 210 | 1753 | 16.3 |
| 9 | 15.658 | 5.6549 | 157 | 2717 | 25.3 |
| 10 | 16.233 | 5.4558 | 159 | 299 | 2.8 |
| 11 | 17.258 | 5.1341 | 148 | 1057 | 9.8 |
| 12 | 18.750 | 4.7288 | 196 | 247 | 2.3 |
| 13 | 19.110 | 4.6404 | 154 | 991 | 9.2 |
| 14 | 20.651 | 4.2975 | 146 | 1323 | 12.3 |
| 15 | 22.881 | 3.8834 | 133 | 219 | 2.0 |
| 16 | 23.232 | 3.8255 | 153 | 149 | 1.4 |
| 17 | 23.864 | 3.7257 | 137 | 351 | 3.3 |
| 18 | 24.751 | 3.5941 | 138 | 331 | 3.1 |
| 19 | 25.323 | 3.5143 | 131 | 1089 | 10.1 |
| 20 | 25.603 | 3.4763 | 138 | 147 | 1.4 |
| 21 | 26.314 | 3.3840 | 108 | 222 | 2.1 |
| 22 | 28.224 | 3.1592 | 150 | 220 | 2.0 |
| 23 | 28.697 | 3.1082 | 137 | 242 | 2.3 |
| 24 | 30.122 | 2.9644 | 106 | 132 | 1.2 |

Example 3

Preparation and Characterization of Salt Forms of Compound 1 (50 mg Scale).

Approximately 50 mg of freebase 1 (Form A) was placed into each of six glass vials and dissolved in 2.0 mL methanol. Appropriate amounts of hydrochloride acid, sulfuric acid, phosphoric acid, methanesulfonic acid or p-toluenesulfonic acid in methanol solutions were added to the vials in molar ratios summarized in Table 2. The mixtures were magnetically stirred for 24 h at room temperature. If a clear solution was obtained, then vacuum centrifugation was conducted at 60° C. to evaporate the solvent. Otherwise, the suspension was centrifuged at 10,000 rpm for 5 min to separate the remaining solid. The resulting wet solids were analyzed by XRPD (FIG. 11) and then dried under vacuum at 40° C. for 4 hours. The dry samples were subsequently analyzed by XRPD (FIGS. 12 and 13) and the results for both the wet and dry salts are shown in Table 2. The XRPD results indicate that on the 50 mg scale, the dry hydrochloride (1:1; Form A), phosphate (1:1; Form A), sulphate (1:1; Form A) and tosylate salts (1:1; Form A) are crystalline materials, whereas the sulphate (2:1) salt and methanesulfonate (1:1) salt are amorphous.

TABLE 2

| 50 mg Scale Salt Screen for Compound 1 in Methanol | | | | | | |
|---|---|---|---|---|---|---|
| | Reagent Solutions | | Observation | | XRPD Results* | |
| Salt (Ratio of Freebase 1: Acid) | Compound 1 (mg) in 2 mL of MeOH | Acid (µL) in (MeOH, µL) | Before Centrifugation | Isolated Yield (%) | Wet | Dry |
| 1 (Form A) (freebase) | 50.8 | N/A (250) | Many particles | | Crystalline | Crystalline |
| HCl (1:1) | 50.2 | 9.4 (77.0) | Many particles | 37 | Crystalline | Crystalline |
| $H_2SO_4$ (1:1) | 50.4 | 6.2 (50.4) | Many particles | 53 | Amorphous | Crystalline |
| $H_2SO_4$ (2:1) | 50.4 | 2.8 (25.2) | Clear solution | | ND | Amorphous |
| $H_3PO_4$ (1:1) | 50.8 | 6.7 (54.4) | Many particles | 63 | Amorphous | Crystalline |
| Methanesulfonic acid (1:1) | 50.2 | 7.3 (60.0) | Clear solution | | ND | Amorphous |
| p-Toluenesulfonic acid (1:1) | 50.4 | 19.7 mg (50.0) | Many particles | 42 | Crystalline | Crystalline |

*ND: not determined.

Example 4

Preparation and Characterization of Salt Forms of Compound 1 (500 mg Scale).

Approximately 500 mg of freebase 1 (Form A) was placed into each of six glass vials and dissolved in 20 mL of methanol. Methanol solutions of hydrochloric acid, sulfuric acid, phosphoric acid, methanesulfonic acid and p-toluenesulfonic acid containing the molar ratios shown in Table 3 were added to each vial and the mixtures were stirred for 24 h at room temperature. If a clear solution was obtained, then vacuum centrifugation at 50° C. for 1.5 h was used to isolate solid material. Subsequently, 20 mL of MTBE was added to the concentrated material and the mixture was stirred for 30 min, collected and dried. If a clear solution was not obtained, the suspension was centrifuged at 10,000 rpm for 5 min to separate remaining solid. The solids were dried under vacuum at 40° C. for 1 day and the dry samples were analyzed by XRPD and the results are shown in Table 3.

Figure 12:
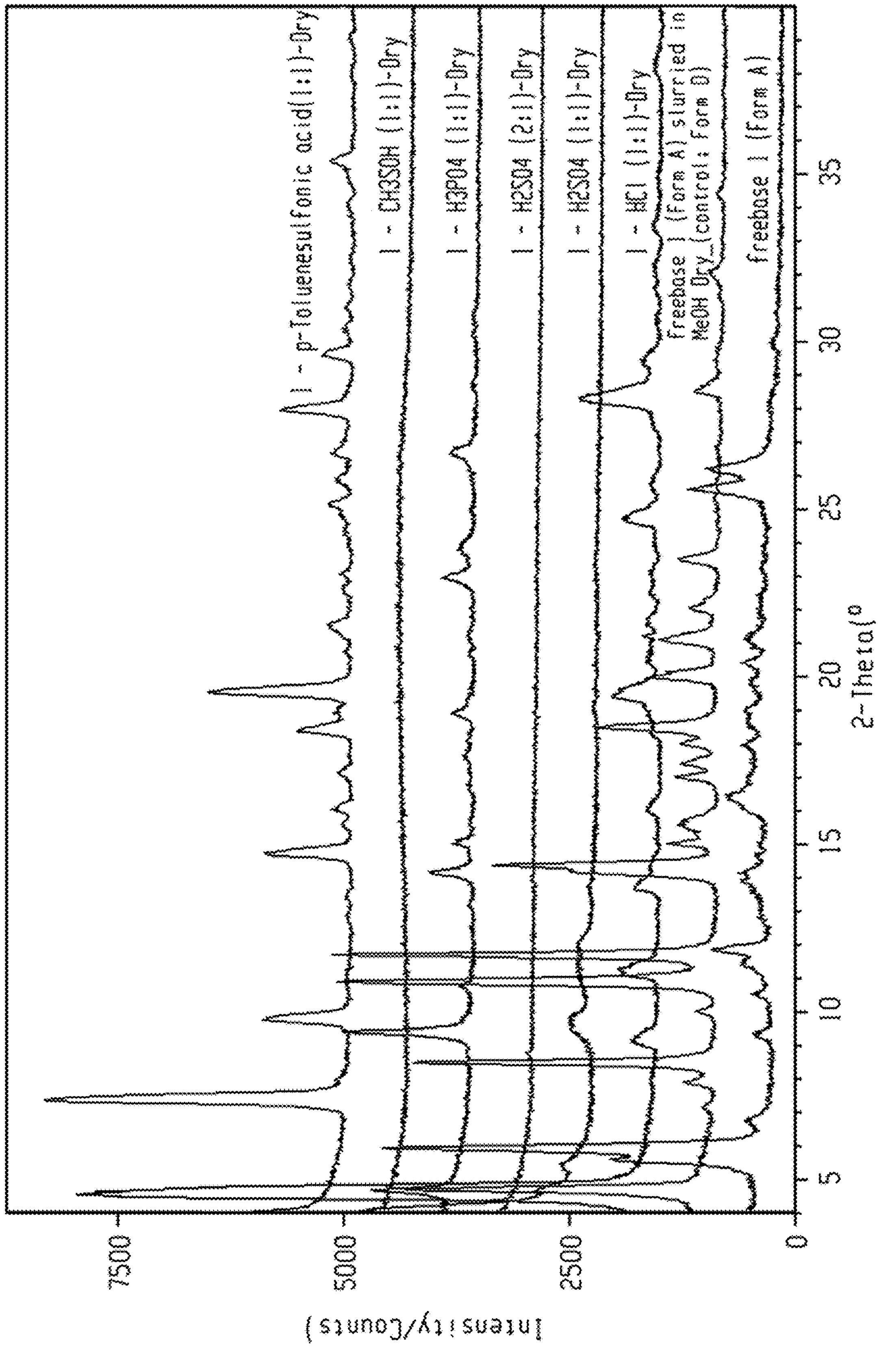
FIG. 12 shows the X-ray powder diffraction patterns (dry samples) of the 50 mg scale salt screen (freebase:acid) for Compound 1.
Figure 13A:
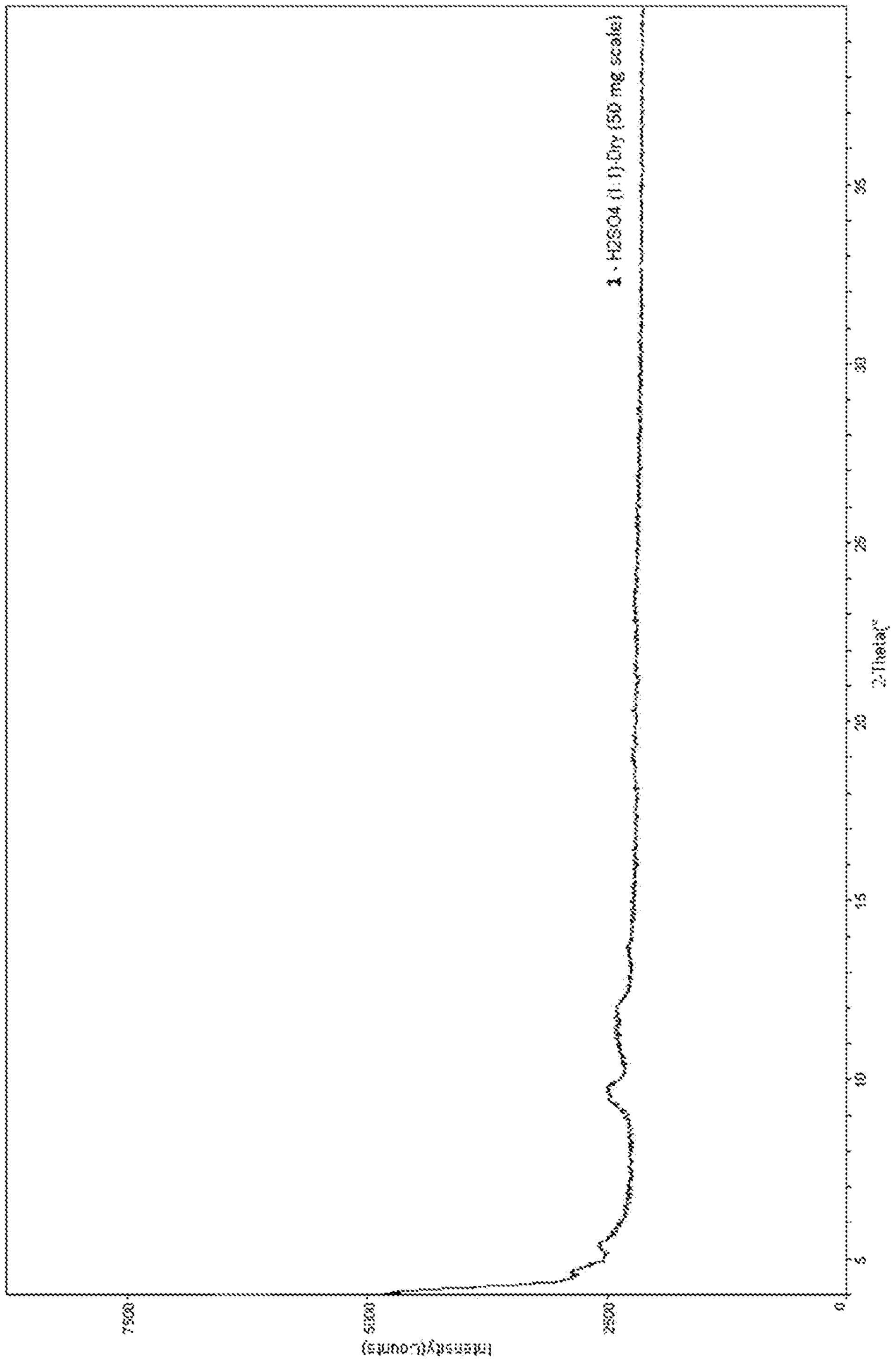
Figure 14:
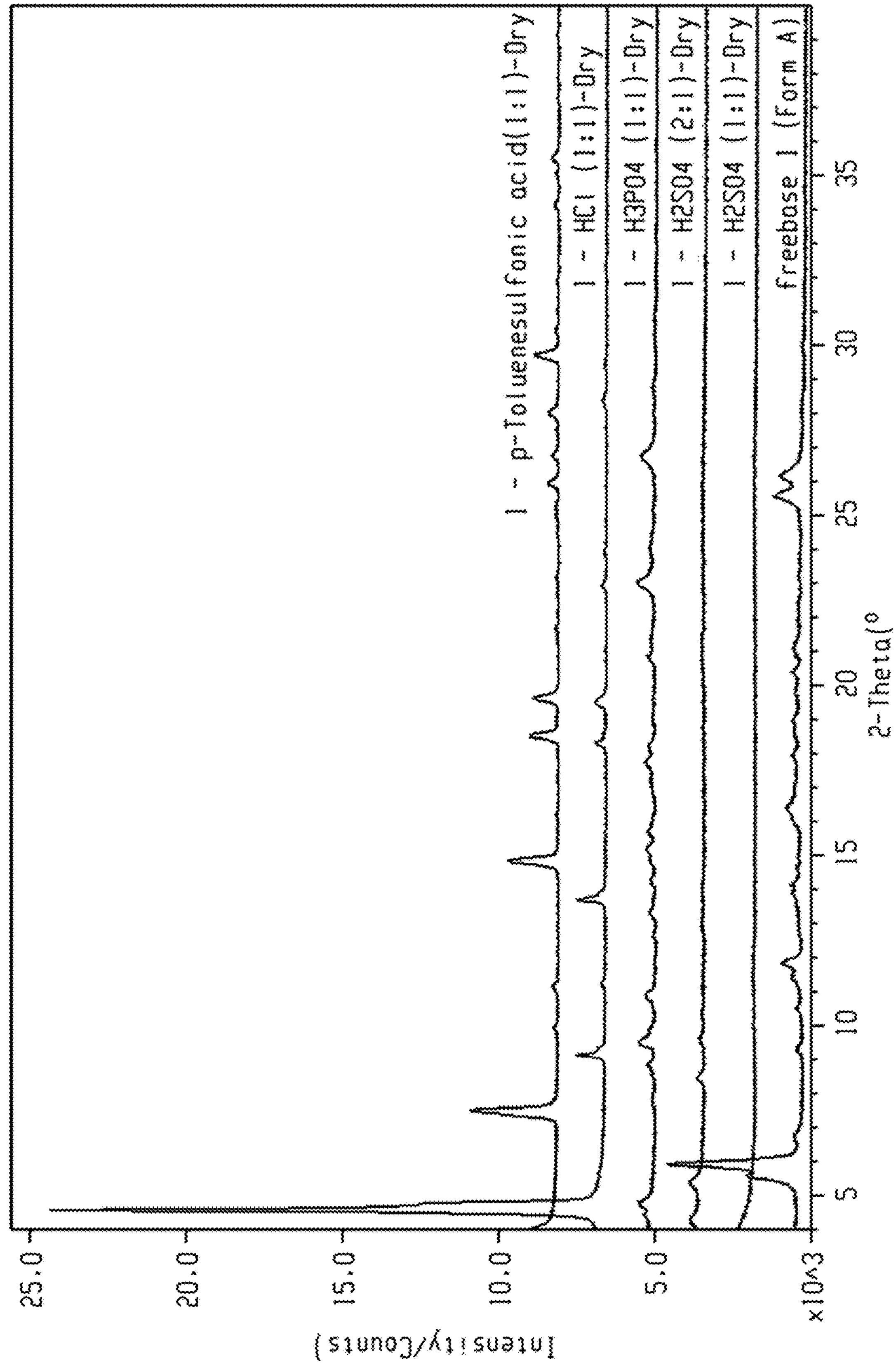
FIG. 14 shows the X-ray powder diffraction patterns (dry samples) of the 500 mg scale salt screen (freebase:acid) for Compound 1 (Form A).

Based upon the 500 mg scale XRPD diffractograms (FIGS. 14 and 15), the hydrochloride (1:1; Form A), phosphate (1:1; Form A), tosylate (1:1; Form A) and the sulphate (2:1; Form A) salts of Compound 1 were crystalline whereas the (1:1) sulphate salt was amorphous. The 500 mg sulphate salt results contrast with the 50 mg scale results, because on the 50 mg scale the (1:1; Form A) sulphate salt was crystalline (FIG. 13) and the (2:1) sulphate salt was amorphous (FIG. 12). Similarly, the methanesulfonate as a (1:1) salt was amorphous on the 50 mg scale and crystalline after isolation as a (1:2; Form A) salt on the 500 mg scale.

The molar ratios (freebase 1:acid) of the isolated salts of Compound 1 in Table 3 were confirmed by RP-HPLC analysis with evaporative light scattering detection (ELSD; Table 4) for the hydrochloride (1:1; Form A), phosphate (1:1; Form A), sulphate (1:1; Form A) and sulphate (2:1; Form A) salts and by $^1$H NMR spectroscopy for the methanesulfonate (1:2; Form A) and tosylate (1:1; Form A) salts.

TABLE 3

| 500 mg Scale Salt Screen for Compound 1 in Methanol | | | | | |
|---|---|---|---|---|---|
| | Reagent Solutions | | | Observation | |
| Salt (Ratio of Freebase 1:Acid) | Compound 1 (mg) in 20 mL of MeOH | Acid (µL) in (µL of MeOH) | Isolated Yield (%) | Before Centrifugation | XRPD Results (Dried) |
| HCl (1:1) | 500.5 | 93.9 (768.3) | 46 | Many particles | Crystalline |
| $H_2SO_4$ (1:1) | 508.3 | 62.2 (508.9) | 81 | Many particles | Amorphous (Crystalline on 50 mg scale) |
| $H_2SO_4$ (2:1) | 504.4 | 28.3 (254.4) | 74 | Many particles | Crystalline |
| $H_3PO_4$ (1:1) | 503.0 | 65.9 (538.8) | 87 | Many particles | Crystalline |
| Methanesulfonic acid (1:1) | 505.3 | 73.7 (603.1) | 54 | Clear solution | Crystalline; isolated as (1:2) |
| p-Toluenesulfonic acid (1:1) | 505.0 | 97.7 mg (500.0) | 39 | Many particles | Crystalline |

TABLE 4

| RP-HPLC with ELSD Detection Assay Conditions | |
|---|---|
| Instrument | Agilent 1200 LC-SEDEX 85 |
| Column | TSKgel Amide-80, 4.6 mm × 150 mm, 3 µm |
| Mobile Phase | A = 85% ACN + 15% 50 mM Ammonium Acetate<br>B = 10% ACN + 90% 50 mM Ammonium Acetate |
| Flow Rate | 1 mL/min |
| Inject Volume | 1 µL |
| Gradient Time | 10 min |
| Column Temperature | 25° C. |

Example 5

DVS, TGA, DSC and $^1$H-NMR Characterization of the Salts of Compound 1

Compound 1•HCl (1:1; Form A)

Figure 19:
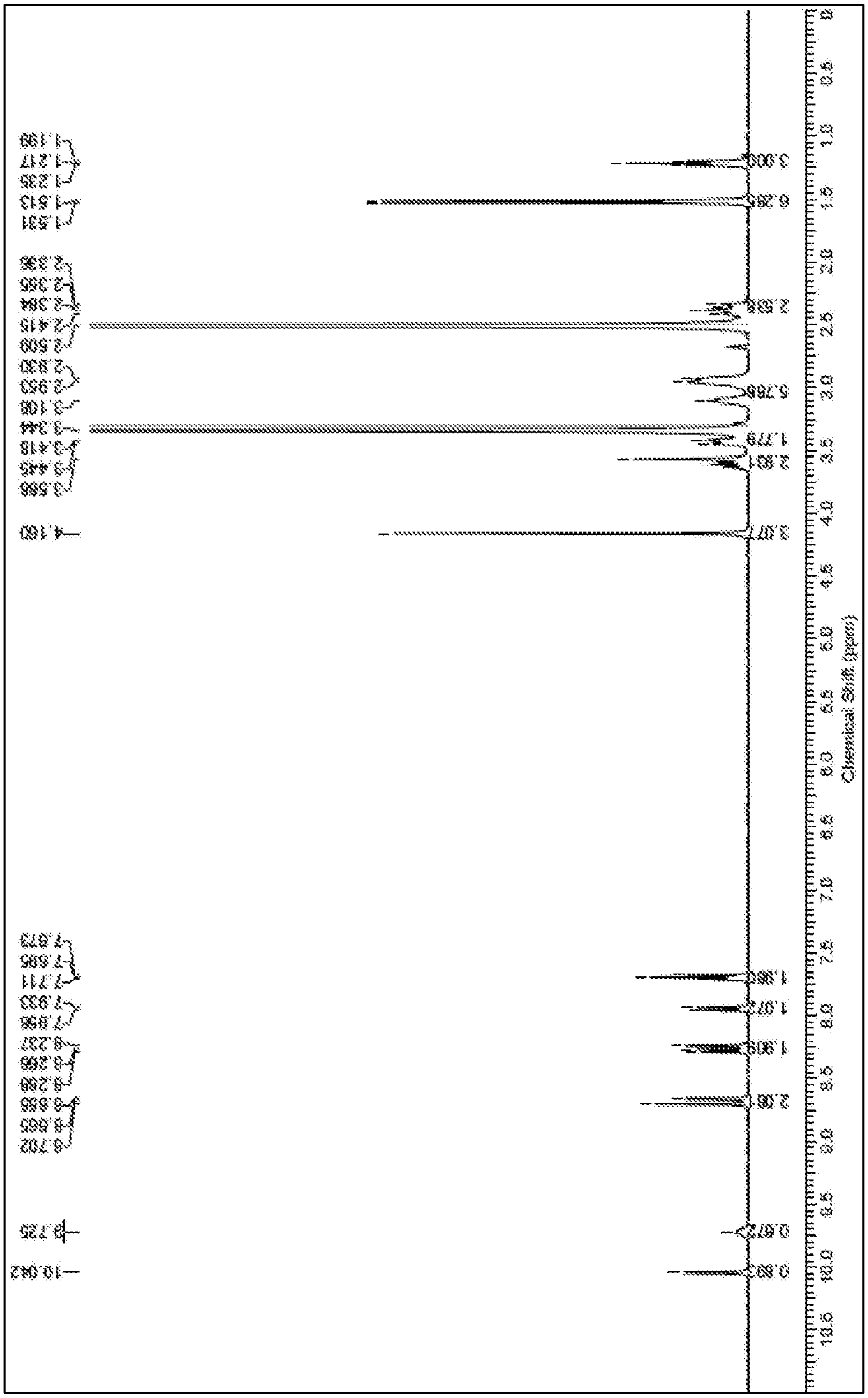
FIG. 19 shows 400 MHz 1H NMR of Compound 1 •HCl (1:1; Form A) in DMSO-d6.

The TGA and DSC profiles of Compound 1•HCl (1:1; Form A) (dried) are shown in FIG. 16. The DSC profile shows two endothermic peaks and a melting point at the onset temperature of 275.4° C. (198.5 J/g). The TGA profile shows a 2.95% weight loss and the DVS isotherm analysis (FIG. 17) indicates that 1•HCl (1:1; Form A) is hygroscopic (3.64% at 80% RH) with no change of crystalline form as shown by the XRPD diffractograms before and after DVS (FIG. 18). These results indicate that 1•HCl (1:1; Form A)) is a monohydrate form (theoretical water content is 3.3%, w/w). The $^1$H NMR spectrum of 1 •HCl (1:1; Form A) is shown in FIG. 19.

Compound 1•$H_2SO_4$ (1:1)

Figure 21A:
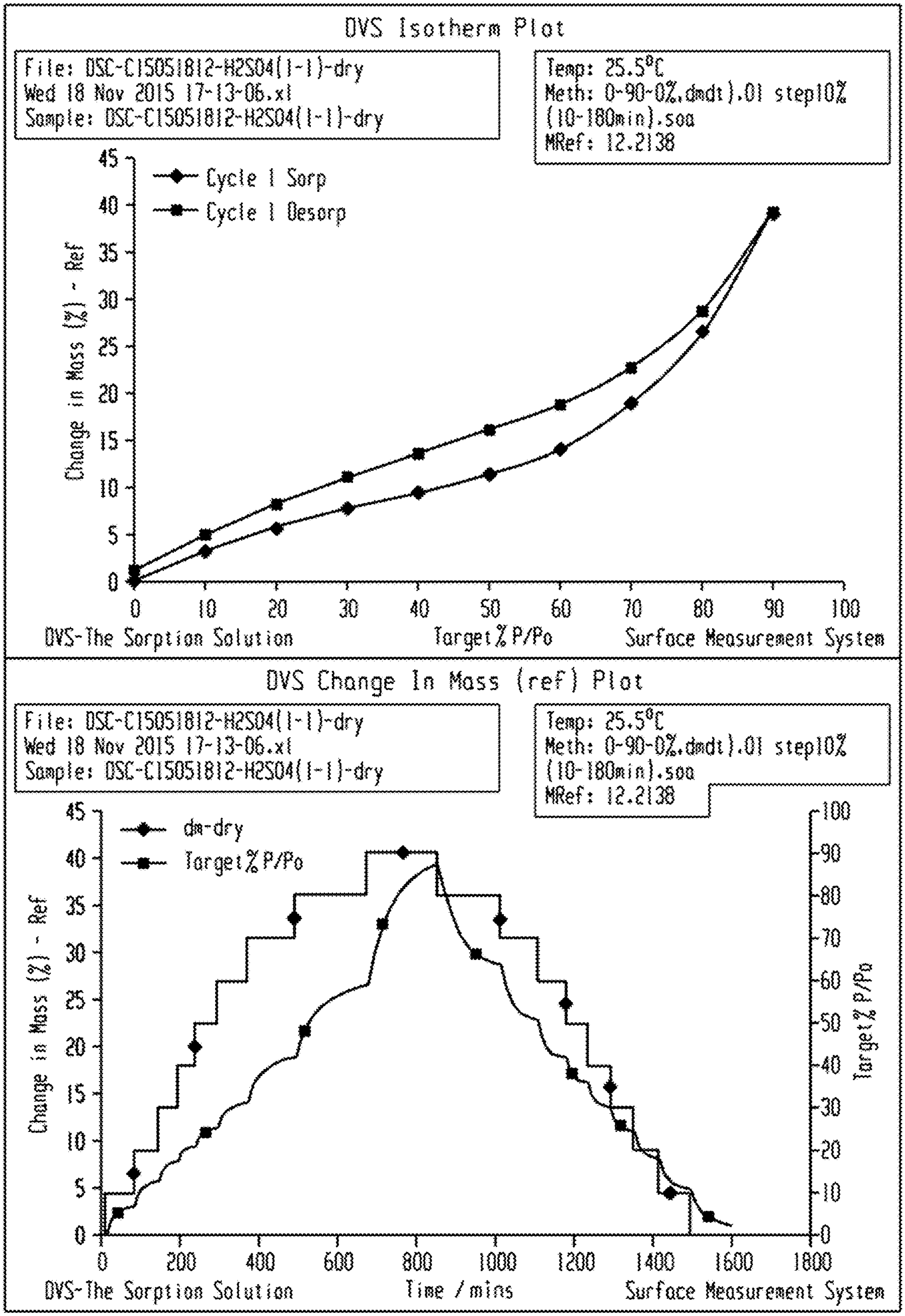

The TGA and DSC profiles of crystalline Compound 1•$H_2SO_4$ (1:1; Form A) from the 50 mg scale are presented in FIG. 20. The TGA profile showed a 4.92% weight loss from 31.6° C. to 120° C. and the DSC profile displays two endothermic peaks, with the first peak at onset temperature 34.3° C. (268.1 J/g) and the second peak at onset temperature 136.0° C. (13.2 J/g). The DVS isotherm analysis (FIG. 21) indicated that Compound 1•$H_2SO_4$ (1:1; Form A) was very hygroscopic (26.42% at 80% RH) with some change of crystalline form as shown by XRPD after DVS (FIG. 22).

Compound 1•$H_3PO_4$ (1:1; Form A)

The DSC and TGA profiles of Compound 1•$H_3PO_4$ (1:1; Form A) are presented in FIG. 23. The DSC profile showed a melting point onset at 229.1° C. (152.2 J/g) and the TGA profile displayed a 0.59% weight loss from 31.4° C. to 120° C. The DVS isotherm analysis (FIG. 24) indicated that Compound 1•$H_3PO_4$ (1:1) is hygroscopic (3.16% at 80% RH) with some change of crystalline form after DVS as shown by XRPD (FIG. 25, with the peaks listed below).

| # | 2-Theta | d(A) | BG | Height | I % |
|---|---|---|---|---|---|
| 1 | 4.473 | 19.7391 | 361 | 174 | 33.5 |
| 2 | 4.826 | 18.2937 | 327 | 376 | 72.3 |
| 3 | 7.697 | 11.4769 | 207 | 69 | 13.3 |
| 4 | 7.965 | 11.0903 | 208 | 63 | 12.1 |
| 5 | 8.558 | 10.3236 | 222 | 78 | 15.0 |
| 6 | 8.889 | 9.9402 | 234 | 213 | 41.0 |
| 7 | 9.542 | 9.2609 | 231 | 492 | 94.6 |
| 8 | 9.896 | 8.9305 | 215 | 190 | 36.5 |
| 9 | 10.904 | 8.1072 | 185 | 290 | 55.8 |
| 10 | 11.901 | 7.4300 | 169 | 39 | 7.5 |
| 11 | 12.638 | 6.9987 | 163 | 106 | 20.4 |
| 12 | 13.347 | 6.6281 | 184 | 187 | 36.0 |
| 13 | 13.666 | 6.4741 | 191 | 82 | 15.8 |
| 14 | 14.298 | 6.1895 | 209 | 120 | 23.1 |
| 15 | 14.888 | 5.9454 | 235 | 130 | 25.0 |
| 16 | 15.185 | 5.8300 | 228 | 257 | 49.4 |
| 17 | 15.697 | 5.6409 | 206 | 219 | 42.1 |
| 18 | 17.255 | 5.1347 | 273 | 61 | 11.7 |
| 19 | 17.766 | 4.9883 | 208 | 295 | 56.7 |
| 20 | 18.181 | 4.8753 | 238 | 167 | 32.1 |
| 21 | 19.053 | 4.6543 | 205 | 74 | 14.2 |
| 22 | 20.880 | 4.2508 | 210 | 213 | 41.0 |
| 23 | 21.377 | 4.1532 | 203 | 133 | 25.6 |
| 24 | 23.034 | 3.8581 | 241 | 520 | 100.0 |
| 25 | 24.041 | 3.6986 | 252 | 116 | 22.3 |
| 26 | 25.202 | 3.5308 | 212 | 48 | 9.2 |
| 27 | 26.743 | 3.3307 | 191 | 439 | 84.4 |
| 28 | 27.983 | 3.1859 | 190 | 44 | 8.5 |
| 29 | 28.771 | 3.1005 | 168 | 126 | 24.2 |
| 30 | 30.338 | 2.9437 | 143 | 77 | 14.8 |
| 31 | 30.949 | 2.8870 | 161 | 56 | 10.8 |

Compound 1 •p-Toluenesulfonic Acid (1:1; Form A)

The TGA and DSC profiles of Compound 1 •p-toluenesulfonic acid (1:1; Form A) are presented in FIG. 26. The TGA profile showed a 0.53% weight loss from room temperature to 120° C. and its DSC profile displayed an endothermic peak with a melting point onset temperature of 229.5° C. (85.0 J/g). The DVS isotherm analysis (FIG. 27) indicated that Compound 1 •p-toluenesulfonic acid (1:1; Form A) was slightly hygroscopic (1.67% at 80% RH) and there was no change of crystalline form after DVS as shown by XRPD (FIG. 28).

Compound 1 •Methanesulfonic Acid (1:2; Form A)

Figure 32:
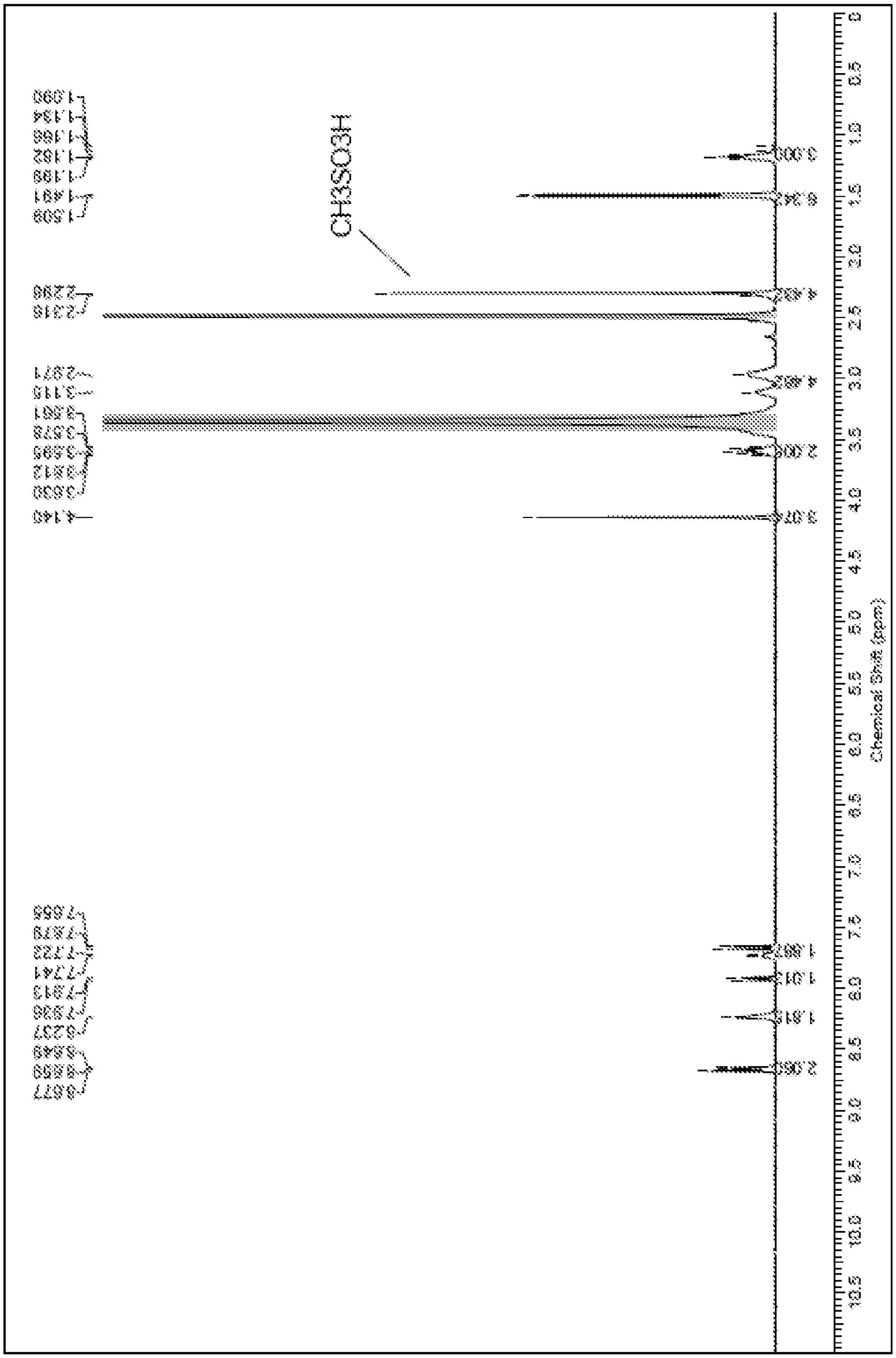
FIG. 32 shows the 400 MHz $^1$H NMR of Compound 1 •methanesulfonic acid (1:2; Form A) in DMSO-d6.
Figure 33:
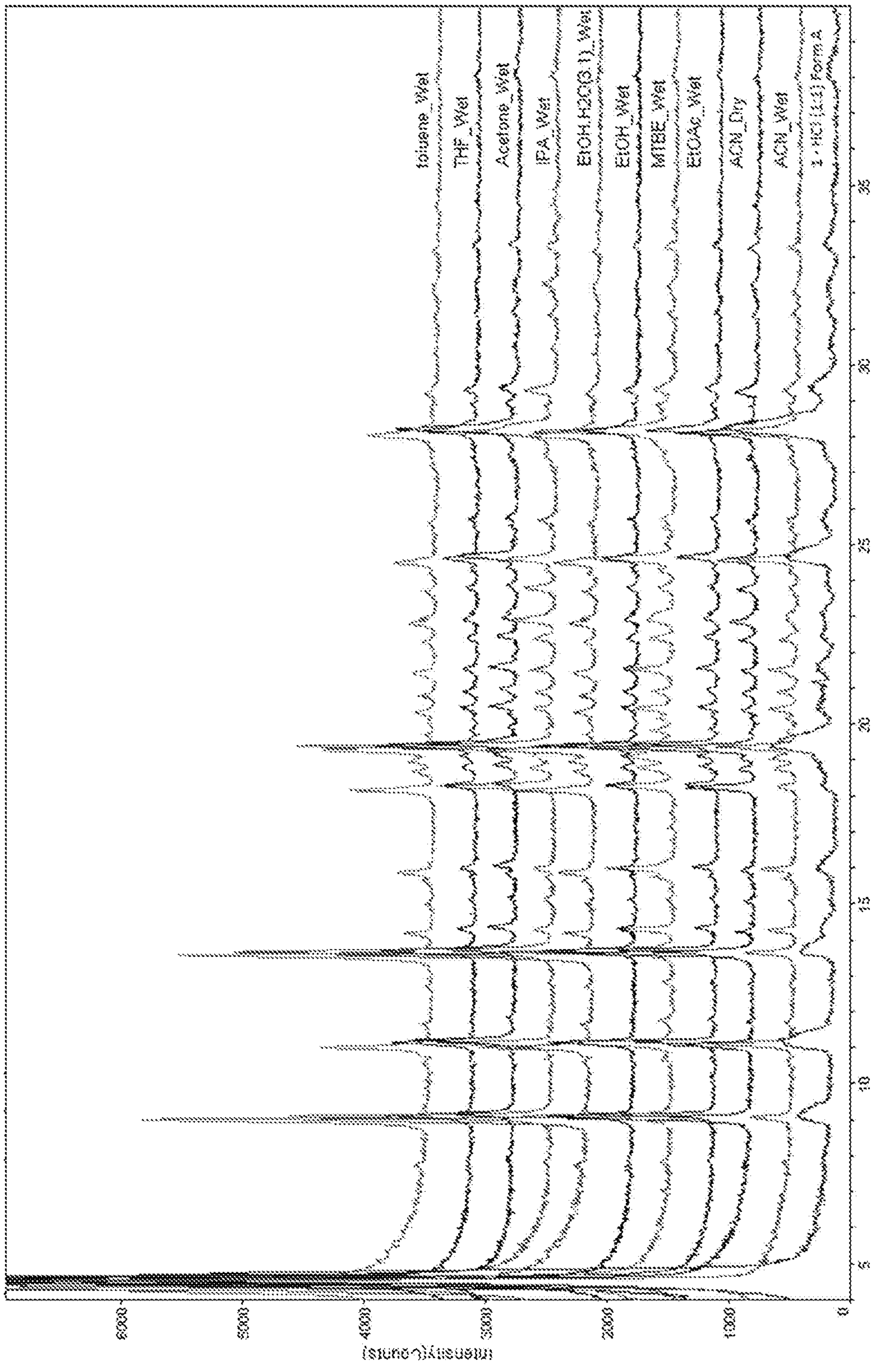
FIG. 33 shows the X-ray powder diffraction patterns of wet samples of a polymorph screen derived from stirring a slurry of Compound 1•HCl (1:1; Form A) in 100 μL of various solvents for 1 day at 40° C.
Figure 34:
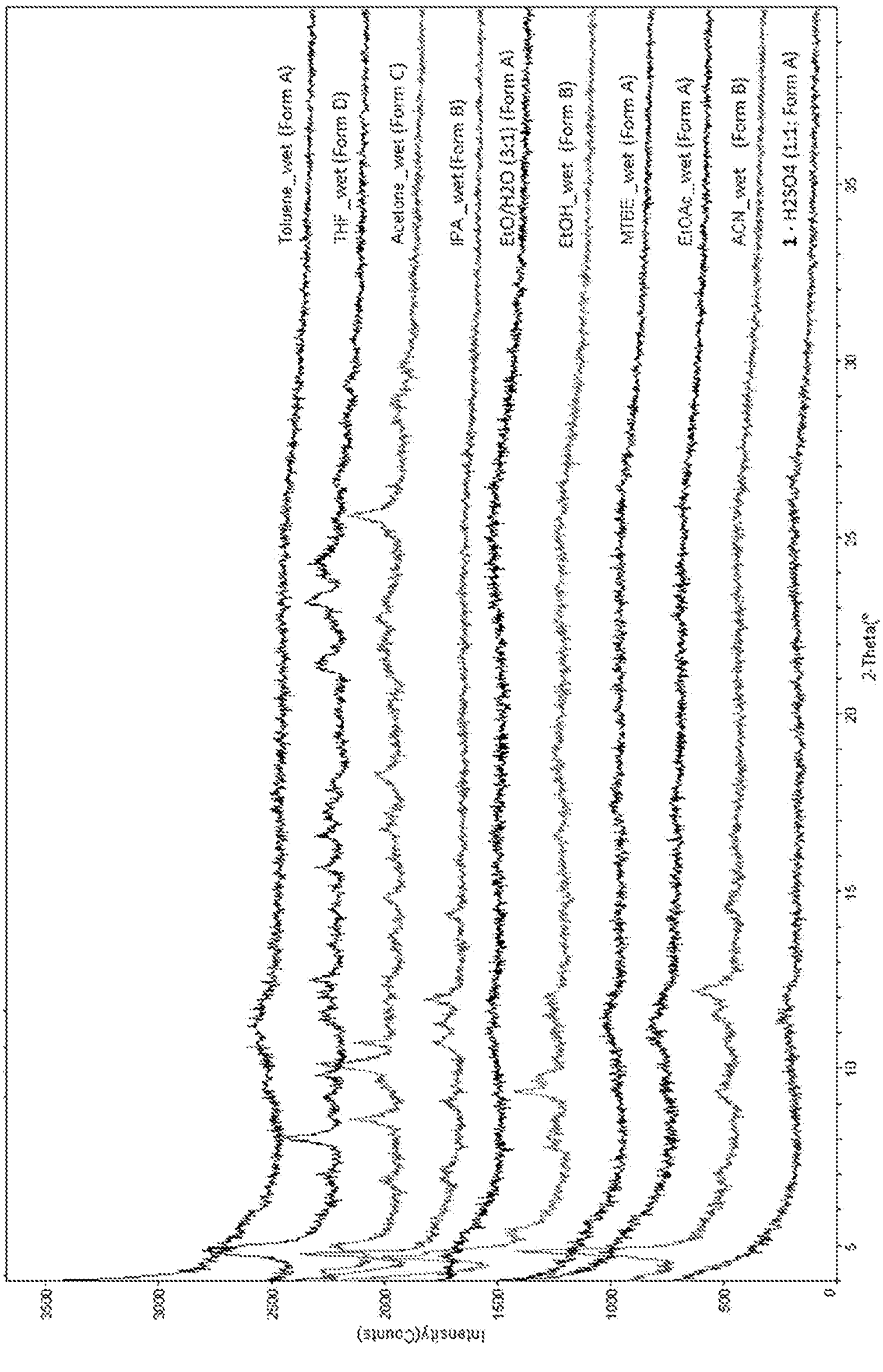
FIG. 34 shows the X-ray powder diffraction patterns of wet samples of Compound 1. $H_2SO_4$ (1:1) polymorphs derived from stirring a slurry of Form A in 100 μL of various solvents for 1 day at 40° C.

The TGA and DSC profiles of Compound 1 •methanesulfonic acid (1:2; Form A) are presented in FIG. 30 and the XRPD pattern is shown in FIG. 31. The DSC profile displayed an endothermic peak with a melting point onset temperature of 223.4° C. (56.3 J/g) and the TGA profile showed a 2.48% weight loss from 31° C. to 120° C. The 400 MHz $^1$H NMR spectrum in DMSO-d6 showed 1:2 molar ratio of Compound 1 to methanesulfonic acid (FIG. 32).

Example 6

Polymorph Screening for the Salts of Compound 1

General Procedure: Approximately 20 mg of each initial salt form (Form A) of Compound 1 was placed into each of nine glass vials and suspended in 100 μL of the various solvents listed in Tables 5-8 and the appearance noted. If clear solution was obtained, then evaporation was conducted for several hours. Otherwise, the slurry was stirred for 24 hours at 40° C. A sample of the slurry was drawn out and analyzed by XRPD (wet sample). The remaining solids were heated at 40° C. at reduced pressure overnight and then analyzed by XRPD (dry sample).

Compound 1•HCl (1:1; Form A)

No new crystalline polymorphs derived from Compound 1-•HCl (1:1; Form A) were formed in any of the solvents listed (Table 5, FIG. 33).

TABLE 5

Polymorph Screening of Compound 1 · HCl (1:1; Form A)

| Solvents | Conc. of Compound 1 · HCl (1:1; Form A) (mg/mL) | Initial Appearance | XRPD Results* (Wet) | (Dry) |
|---|---|---|---|---|
| ACN | 205 | Many particles | Form A | Form A |
| EtOAc | 201 | Many particles | Form A | ND |
| MTBE | 183 | Many particles | Form A | ND |
| EtOH | 208 | Many particles | Form A | ND |
| EtOH:$H_2O$ (3:1) | 194 | Many particles | Form A | ND |
| IPA | 203 | Many particles | Form A | ND |
| Acetone | 210 | Many particles | Form A | ND |
| THF | 191 | Many particles | Form A | ND |
| Toluene | 190 | Many particles | Form A | ND |

*Results after stirring a slurry of Compound 1 · HCl (1:1; Form A) 100 μL of various solvents at 40° C. for 1 day;
ND: not determined.

Compound 1 •Sulphate (1:1; Forms B, C, and D)

Three new crystalline forms were derived from Compound 1 •$H_2SO_4$ (1:1; Form A) by the slurry method: Forms B, C and D (Table 6, FIGS. 34 and 35). Form B was converted to Form A after heating at 40° C.

TABLE 6

Polymorph Screening of Compound 1•$H_2SO_4$ (1:1; Form A)

| Solvents | Conc. of Compound 1•$H_2SO_4$ (1:1; Form A) (mg/mL) | Initial Appearance | Method | XRPD Results* (Wet) | (Dry) |
|---|---|---|---|---|---|
| ACN | 205 | Many particles | Slurry | Form B | Form A |
| EtOAc | 201 | Many particles | Slurry | Form A | Form A |

TABLE 6-continued

Polymorph Screening of Compound 1•$H_2SO_4$ (1:1; Form A)

| Solvents | Conc. of Compound 1•$H_2SO_4$ (1:1; Form A) (mg/mL) | Initial Appearance | Method | XRPD Results* (Wet) | XRPD Results* (Dry) |
|---|---|---|---|---|---|
| MTBE | 183 | Many particles | Slurry | Form A | Form A |
| EtOH | 208 | Many particles | Slurry | Form B | Form A |
| EtOH:$H_2O$ (3:1) | 194 | Many particles | Slurry | Form A | Form A |
| IPA | 203 | Many particles | Slurry | Form B | Form A |
| Acetone | 210 | Many particles | Slurry | Form C | Form C |
| THF | 191 | Many particles | Slurry | Form D | Form D |
| Toluene | 190 | Many particles | Slurry | Form A | Form A |

*Results after stirring a slurry of Compound 1•$H_2SO_4$ (1:1; Form A) 100 μL of various solvents at 40° C. for 1 day.

Form B (Wet from IPA):

| # | 2-Theta | d(A) | BG | Height | I % | Area |
|---|---|---|---|---|---|---|
| 1 | 4.206 | 20.9910 | 303 | 462 | 100.0 | 5952 |
| 2 | 4.790 | 18.4322 | 400 | 460 | 99.6 | 2143 |
| 3 | 6.918 | 12.7662 | 183 | 67 | 14.5 | 1470 |
| 4 | 7.173 | 12.3127 | 174 | 69 | 14.9 | 1477 |
| 5 | 9.116 | 9.6925 | 163 | 77 | 16.7 | 896 |
| 6 | 10.784 | 8.1974 | 173 | 110 | 23.8 | 1721 |
| 7 | 11.317 | 7.8124 | 168 | 107 | 23.2 | 2572 |
| 8 | 11.973 | 7.3858 | 179 | 139 | 30.1 | 1403 |
| 9 | 14.410 | 6.1414 | 148 | 75 | 16.2 | 1146 |

Form C (Wet from Acetone):

| # | 2-Theta | d(A) | BG | Height | I % |
|---|---|---|---|---|---|
| 1 | 4.987 | 17.7049 | 282 | 204 | 60.4 |
| 2 | 6.875 | 12.8469 | 183 | 82 | 24.3 |
| 3 | 8.595 | 10.2788 | 187 | 209 | 61.8 |
| 4 | 9.641 | 9.1664 | 205 | 75 | 22.2 |
| 5 | 10.170 | 8.6902 | 201 | 338 | 100.0 |
| 6 | 12.502 | 7.0744 | 197 | 51 | 15.1 |
| 7 | 13.801 | 6.4111 | 174 | 48 | 14.2 |
| 8 | 14.847 | 5.9617 | 177 | 72 | 21.3 |
| 9 | 16.765 | 5.2837 | 176 | 91 | 26.9 |
| 10 | 17.236 | 5.1405 | 183 | 60 | 17.8 |
| 11 | 18.300 | 4.8440 | 180 | 104 | 30.8 |
| 12 | 21.597 | 4.1114 | 204 | 63 | 18.6 |
| 13 | 21.989 | 4.0388 | 209 | 61 | 18.0 |
| 14 | 22.778 | 3.9007 | 210 | 78 | 23.1 |
| 15 | 23.273 | 3.8189 | 202 | 57 | 16.9 |
| 16 | 25.657 | 3.4692 | 183 | 221 | 65.4 |
| 17 | 28.408 | 3.1392 | 156 | 45 | 13.3 |
| 18 | 28.971 | 3.0794 | 143 | 71 | 21.0 |
| 19 | 29.934 | 2.9825 | 125 | 54 | 16.0 |

Form D (Wet from THF):

| # | 2-Theta | d(A) | BG | Height | I % |
|---|---|---|---|---|---|
| 1 | 4.869 | 18.1326 | 373 | 426 | 100.0 |
| 2 | 7.059 | 12.5128 | 205 | 83 | 19.5 |
| 3 | 8.082 | 10.9307 | 202 | 230 | 54.0 |
| 4 | 9.205 | 9.5996 | 196 | 68 | 16.0 |
| 5 | 9.839 | 8.9818 | 200 | 98 | 23.0 |
| 6 | 11.393 | 7.7604 | 211 | 69 | 16.2 |
| 7 | 11.631 | 7.6023 | 218 | 60 | 14.1 |
| 8 | 12.184 | 7.2582 | 196 | 87 | 20.4 |
| 9 | 12.521 | 7.0634 | 212 | 113 | 26.5 |
| 10 | 13.537 | 6.5355 | 197 | 52 | 12.2 |

-continued

| # | 2-Theta | d(A) | BG | Height | I % |
|---|---|---|---|---|---|
| 11 | 15.190 | 5.8278 | 188 | 49 | 11.5 |
| 12 | 15.713 | 5.6350 | 190 | 106 | 24.9 |
| 13 | 16.579 | 5.3426 | 205 | 94 | 22.1 |
| 14 | 17.263 | 5.1325 | 203 | 58 | 13.6 |
| 15 | 17.475 | 5.0706 | 197 | 55 | 12.9 |
| 16 | 21.360 | 4.1563 | 177 | 112 | 26.3 |
| 17 | 21.965 | 4.0433 | 179 | 47 | 11.0 |
| 18 | 22.761 | 3.9037 | 189 | 66 | 15.5 |
| 19 | 23.196 | 3.8315 | 196 | 146 | 34.3 |
| 20 | 23.976 | 3.7085 | 204 | 92 | 21.6 |
| 21 | 24.395 | 3.6458 | 200 | 105 | 24.6 |
| 22 | 29.309 | 3.0447 | 123 | 50 | 11.7 |

Form D (dry from THF):

| # | 2-Theta | d(A) | BG | Height | I % |
|---|---|---|---|---|---|
| 1 | 8.103 | 10.9023 | 204 | 164 | 78.1 |
| 2 | 8.699 | 10.1571 | 203 | 75 | 35.7 |
| 3 | 9.222 | 9.5817 | 186 | 60 | 28.6 |
| 4 | 9.879 | 8.9458 | 183 | 121 | 57.6 |
| 5 | 11.616 | 7.6119 | 178 | 74 | 35.2 |
| 6 | 12.561 | 7.0410 | 170 | 176 | 83.8 |
| 7 | 13.513 | 6.5473 | 160 | 81 | 38.6 |
| 8 | 14.058 | 6.2946 | 162 | 58 | 27.6 |
| 9 | 14.499 | 6.1040 | 160 | 55 | 26.2 |
| 10 | 15.202 | 5.8232 | 155 | 76 | 36.2 |
| 11 | 15.773 | 5.6138 | 158 | 174 | 82.9 |
| 12 | 16.585 | 5.3408 | 162 | 179 | 85.2 |
| 13 | 17.154 | 5.1648 | 155 | 110 | 52.4 |
| 14 | 17.468 | 5.0728 | 163 | 65 | 31.0 |
| 15 | 17.960 | 4.9348 | 151 | 86 | 41.0 |
| 16 | 18.224 | 4.8639 | 146 | 75 | 35.7 |
| 17 | 19.409 | 4.5697 | 142 | 60 | 28.6 |
| 18 | 20.156 | 4.4018 | 144 | 58 | 27.6 |
| 19 | 21.356 | 4.1572 | 149 | 150 | 71.4 |
| 20 | 22.892 | 3.8815 | 156 | 70 | 33.3 |
| 21 | 23.211 | 3.8289 | 160 | 210 | 100.0 |
| 22 | 23.980 | 3.7080 | 162 | 113 | 53.8 |
| 23 | 24.394 | 3.6459 | 153 | 75 | 35.7 |
| 24 | 24.785 | 3.5892 | 151 | 69 | 32.9 |
| 25 | 26.741 | 3.3310 | 126 | 71 | 33.8 |
| 26 | 29.363 | 3.0393 | 102 | 49 | 23.3 |

Compound 1 •Sulphate (2:1; Forms B, C, D, E and F)

Five new forms of 1•$H_2SO_4$ (2:1) were derived from Compound 1•$H_2SO_4$ (2:1; Form A) and are summarized in Table 7 and FIG. 36. Forms B, C, E and F were crystalline while Form D was amorphous.

TABLE 7

Polymorph Screening of Compound 1•$H_2SO_4$ (2:1; Form A)

| Solvents | Conc. of Compound 1•$H_2SO_4$ (2:1; Form A) (mg/mL) | Initial Appearance | Method | XRPD Results* (Dry) |
|---|---|---|---|---|
| ACN | 203 | Many particles | Slurry | Form B |
| EtOAc | 212 | Many particles | Slurry | Form C |
| MTBE | 212 | Many particles | Slurry | Form C |
| EtOH | 220 | Many particles | Slurry | Form C |
| EtOH:$H_2O$ (3:1)* | 216 | Clear solution | Evaporation | Form D |
| IPA | 207 | Many particles | Slurry | Form D |

TABLE 7-continued

| Polymorph Screening of Compound 1•$H_2SO_4$ (2:1; Form A) | | | | |
|---|---|---|---|---|
| Solvents | Conc. of Compound 1•$H_2SO_4$ (2:1; Form A) (mg/mL) | Initial Appearance | Method | XRPD Results* (Dry) |
| Acetone | 188 | Many particles | Slurry | Form E |
| THF | 200 | Many particles | Slurry | Form F |
| Toluene | 203 | Many particles | Slurry | Form C |

*Results after stirring a slurry of Compound 1 • H2SO4 (2:1; Form A) in 100 μL of various solvents at 40° C. for 1 day except for EtOH:H2O (3:1), which was evaporated for several hours.

Form A of Compound 1•$H_2SO_4$ (2:1)

| # | 2-Theta | d(A) | BG | Height | I % |
|---|---|---|---|---|---|
| 1 | 4.333 | 20.3746 | 489 | 181 | 53.4 |
| 2 | 5.439 | 16.2345 | 350 | 339 | 100.0 |
| 3 | 8.440 | 10.4682 | 208 | 227 | 67.0 |
| 4 | 9.658 | 9.1500 | 214 | 144 | 42.5 |
| 5 | 10.367 | 8.5258 | 227 | 68 | 20.1 |
| 6 | 13.039 | 6.7844 | 222 | 78 | 23.0 |
| 7 | 13.919 | 6.3573 | 221 | 52 | 15.3 |
| 8 | 14.153 | 6.2525 | 218 | 57 | 16.8 |
| 9 | 20.729 | 4.2815 | 208 | 85 | 25.1 |
| 10 | 21.318 | 4.1644 | 214 | 77 | 22.7 |

Form B of Compound 1•$H_2SO_4$ (2:1) (Dry from ACN)

| # | 2-Theta | d(A) | BG | Height | I % |
|---|---|---|---|---|---|
| 1 | 4.513 | 19.5623 | 492 | 122 | 24.4 |
| 2 | 6.546 | 13.4907 | 265 | 133 | 26.5 |
| 3 | 7.293 | 12.1110 | 233 | 74 | 14.8 |
| 4 | 7.906 | 11.1737 | 208 | 501 | 100.0 |
| 5 | 11.593 | 7.6269 | 179 | 282 | 56.3 |
| 6 | 12.065 | 7.3297 | 180 | 330 | 65.9 |
| 7 | 12.382 | 7.1427 | 193 | 184 | 36.7 |
| 8 | 14.510 | 6.0997 | 158 | 398 | 79.4 |
| 9 | 15.440 | 5.7343 | 171 | 162 | 32.3 |
| 10 | 16.129 | 5.4906 | 159 | 207 | 41.3 |
| 11 | 17.198 | 5.1519 | 175 | 175 | 34.9 |
| 12 | 17.806 | 4.9771 | 158 | 153 | 30.5 |
| 13 | 18.243 | 4.8590 | 163 | 78 | 15.6 |
| 14 | 19.221 | 4.6138 | 230 | 159 | 31.7 |
| 15 | 19.583 | 4.5294 | 240 | 122 | 24.4 |
| 16 | 20.431 | 4.3433 | 193 | 185 | 36.9 |
| 17 | 21.792 | 4.0749 | 191 | 91 | 18.2 |
| 18 | 22.322 | 3.9794 | 202 | 92 | 18.4 |
| 19 | 22.619 | 3.9279 | 197 | 113 | 22.6 |
| 20 | 23.108 | 3.8458 | 193 | 259 | 51.7 |
| 21 | 23.662 | 3.7570 | 191 | 105 | 21.0 |
| 22 | 24.571 | 3.6200 | 201 | 120 | 24.0 |
| 23 | 26.131 | 3.4074 | 199 | 303 | 60.5 |
| 24 | 27.392 | 3.2533 | 199 | 365 | 72.9 |
| 25 | 29.046 | 3.0717 | 164 | 126 | 25.1 |

Form C of Compound 1•$H_2SO_4$ (2:1) (Dry from EtOH)

| # | 2-Theta | d(A) | BG | Height | I % |
|---|---|---|---|---|---|
| 1 | 4.632 | 19.0603 | 417 | 91 | 28.3 |
| 2 | 7.548 | 11.7022 | 212 | 67 | 20.8 |
| 3 | 9.325 | 9.4760 | 206 | 322 | 100.0 |
| 4 | 12.279 | 7.2020 | 176 | 60 | 18.6 |
| 5 | 12.620 | 7.0083 | 177 | 63 | 19.6 |
| 6 | 14.081 | 6.2843 | 187 | 49 | 15.2 |
| 7 | 16.288 | 5.4375 | 179 | 50 | 15.5 |
| 8 | 20.429 | 4.3436 | 168 | 62 | 19.3 |

-continued

| # | 2-Theta | d(A) | BG | Height | I % |
|---|---|---|---|---|---|
| 9 | 20.773 | 4.2726 | 190 | 48 | 14.9 |
| 10 | 22.504 | 3.9476 | 186 | 48 | 14.9 |
| 11 | 23.899 | 3.7203 | 188 | 60 | 18.6 |
| 12 | 27.981 | 3.1862 | 149 | 51 | 15.8 |

Form E of Compound 1•$H_2SO_4$ (2:1) (Dry from Acetone)

| # | 2-Theta | d(A) | BG | Height | I % |
|---|---|---|---|---|---|
| 1 | 4.512 | 19.5688 | 378 | 354 | 62.7 |
| 2 | 5.402 | 16.3455 | 250 | 356 | 63.0 |
| 3 | 8.795 | 10.0460 | 158 | 135 | 23.9 |
| 4 | 10.804 | 8.1823 | 142 | 565 | 100.0 |
| 5 | 11.278 | 7.8390 | 146 | 151 | 26.7 |
| 6 | 12.803 | 6.9085 | 147 | 53 | 9.4 |
| 7 | 13.526 | 6.5411 | 160 | 83 | 14.7 |
| 8 | 13.824 | 6.4005 | 143 | 104 | 18.4 |
| 9 | 14.157 | 6.2508 | 144 | 179 | 31.7 |
| 10 | 15.320 | 5.7787 | 170 | 92 | 16.3 |
| 11 | 15.758 | 5.6190 | 138 | 145 | 25.7 |
| 12 | 16.088 | 5.5045 | 144 | 302 | 53.5 |
| 13 | 16.899 | 5.2423 | 149 | 122 | 21.6 |
| 14 | 17.371 | 5.1008 | 153 | 186 | 32.9 |
| 15 | 18.446 | 4.8059 | 154 | 54 | 9.6 |
| 16 | 18.869 | 4.6992 | 148 | 217 | 38.4 |
| 17 | 19.619 | 4.5211 | 136 | 149 | 26.4 |
| 18 | 20.406 | 4.3485 | 126 | 80 | 14.2 |
| 19 | 20.828 | 4.2613 | 132 | 57 | 10.1 |
| 20 | 21.413 | 4.1463 | 144 | 95 | 16.8 |
| 21 | 21.653 | 4.1009 | 152 | 91 | 16.1 |
| 22 | 22.597 | 3.9316 | 181 | 224 | 39.6 |
| 23 | 22.935 | 3.8745 | 165 | 551 | 97.5 |
| 24 | 23.702 | 3.7508 | 177 | 240 | 42.5 |
| 25 | 24.179 | 3.6778 | 156 | 63 | 11.2 |
| 26 | 24.988 | 3.5606 | 147 | 51 | 9.0 |
| 27 | 25.794 | 3.4510 | 194 | 102 | 18.1 |
| 28 | 26.211 | 3.3971 | 167 | 166 | 29.4 |
| 29 | 26.665 | 3.3403 | 197 | 151 | 26.7 |
| 30 | 27.490 | 3.2418 | 186 | 462 | 81.8 |
| 31 | 29.418 | 3.0337 | 133 | 49 | 8.7 |
| 32 | 30.349 | 2.9427 | 126 | 77 | 13.6 |
| 33 | 32.302 | 2.7691 | 104 | 69 | 12.2 |

Form F of Compound 1•$H_2SO_4$ (2:1) (Dry from THF)

| # | 2-Theta | d(A) | BG | Height | I % |
|---|---|---|---|---|---|
| 1 | 4.455 | 19.8189 | 444 | 675 | 100.0 |
| 2 | 5.283 | 16.7147 | 368 | 96 | 14.2 |
| 3 | 6.443 | 13.7062 | 293 | 103 | 15.3 |
| 4 | 7.211 | 12.2493 | 252 | 178 | 26.4 |
| 5 | 8.479 | 10.4202 | 196 | 95 | 14.1 |
| 6 | 9.008 | 9.8089 | 192 | 109 | 16.1 |
| 7 | 9.521 | 9.2813 | 162 | 70 | 10.4 |
| 8 | 10.146 | 8.7110 | 161 | 101 | 15.0 |
| 9 | 10.392 | 8.5059 | 161 | 82 | 12.1 |
| 10 | 10.684 | 8.2738 | 162 | 289 | 42.8 |
| 11 | 11.038 | 8.0092 | 175 | 94 | 13.9 |
| 12 | 12.001 | 7.3682 | 167 | 113 | 16.7 |
| 13 | 12.369 | 7.1502 | 158 | 63 | 9.3 |
| 14 | 13.007 | 6.8005 | 160 | 105 | 15.6 |
| 15 | 13.510 | 6.5488 | 152 | 113 | 16.7 |
| 16 | 13.647 | 6.4831 | 144 | 114 | 16.9 |
| 17 | 13.981 | 6.3291 | 149 | 123 | 18.2 |
| 18 | 15.678 | 5.6478 | 145 | 319 | 47.3 |
| 19 | 15.971 | 5.5445 | 148 | 231 | 34.2 |
| 20 | 17.192 | 5.1535 | 148 | 206 | 30.5 |
| 21 | 18.124 | 4.8906 | 150 | 221 | 32.7 |
| 22 | 18.752 | 4.7283 | 148 | 90 | 13.3 |
| 23 | 19.542 | 4.5388 | 138 | 239 | 35.4 |
| 24 | 20.406 | 4.3484 | 134 | 99 | 14.7 |
| 25 | 21.284 | 4.1710 | 142 | 85 | 12.6 |
| 26 | 21.497 | 4.1301 | 142 | 117 | 17.3 |

-continued

| # | 2-Theta | d(A) | BG | Height | I % |
|---|---|---|---|---|---|
| 27 | 21.747 | 4.0833 | 143 | 103 | 15.3 |
| 28 | 22.360 | 3.9727 | 148 | 89 | 13.2 |
| 29 | 22.797 | 3.8975 | 147 | 430 | 63.7 |
| 30 | 23.558 | 3.7733 | 153 | 94 | 13.9 |
| 31 | 24.217 | 3.6721 | 137 | 100 | 14.8 |
| 32 | 25.991 | 3.4254 | 141 | 517 | 76.6 |
| 33 | 27.372 | 3.2557 | 138 | 162 | 24.0 |
| 34 | 29.620 | 3.0134 | 102 | 106 | 15.7 |

Form G (or C) of Compound 1•$H_2SO_4$ (2:1) (Dry from Toluene)

| # | 2-Theta | d(A) | BG | Height | I % |
|---|---|---|---|---|---|
| 1 | 7.300 | 12.1002 | 296 | 203 | 100.0 |
| 2 | 7.751 | 11.3970 | 280 | 67 | 33.0 |
| 3 | 8.318 | 10.6205 | 250 | 114 | 56.2 |
| 4 | 9.798 | 9.0194 | 219 | 148 | 72.9 |
| 5 | 10.392 | 8.5054 | 221 | 161 | 79.3 |
| 6 | 12.244 | 7.2225 | 201 | 53 | 26.1 |
| 7 | 12.752 | 6.9364 | 208 | 128 | 63.1 |
| 8 | 13.053 | 6.7767 | 216 | 64 | 31.5 |
| 9 | 14.014 | 6.3142 | 208 | 52 | 25.6 |
| 10 | 16.077 | 5.5084 | 210 | 56 | 27.6 |
| 11 | 16.591 | 5.3389 | 205 | 52 | 25.6 |
| 12 | 16.759 | 5.2856 | 206 | 63 | 31.0 |
| 13 | 17.370 | 5.1011 | 198 | 109 | 53.7 |
| 14 | 25.634 | 3.4723 | 209 | 143 | 70.4 |
| 15 | 25.873 | 3.4407 | 203 | 77 | 37.9 |

Compound 1 •p-Toluenesulfonic Acid (1:1; Form B)

One new crystalline form (Form B) was derived from Compound 1 •p-toluenesulfonic acid (1:1; Form A) whereas Form C was mostly amorphous (Table 8 and FIGS. 37, 38). The DSC profile of Compound 1 •p-toluenesulfonic acid (1:1; Form B) displayed two endothermic peaks (FIG. 39). The first was at the onset temperature of 82.2° C. (9.9 J/g), which may be related to the solid form transition to Form A, and the second at the onset temperature of 229.0° C. (81.4 J/g) was likely the melt of Form A.

TABLE 8

Polymorph Screening of Compound 1•p-Toluenesulfonic Acid (1:1; Form A)

| Solvents | Conc. of Compound 1•p-Toluene-sulfonic Acid (1:1; Form A) (mg/mL) | Initial Appearance | Method | XRPD Results* (Wet) | XRPD Results* (Dry) |
|---|---|---|---|---|---|
| ACN | 236 | Many particles | Slurry | Form A | Form A |
| EtOAc | 198 | Many particles | Slurry | Form A | Form A |
| MTBE | 238 | Many particles | Slurry | Form A | Form A |
| EtOH | 195 | Many particles | Slurry | Form A | Form A |
| EtOH:$H_2O$ (3:1) | 196 | Clear solution | Evapo-ration | ND | Form C |
| IPA | 203 | Many particles | Slurry | Form A | Form A |
| Acetone | 194 | Many particles | Slurry | Form A | Form A |
| THF | 203 | Many particles | Slurry | Form B | Form B |
| Toluene | 205 | Many particles | Slurry | Form A | Form A |

*Results after stirring a slurry of Compound 1 • p-toluenesulfonic acid (1:1; Form A) in 100 μL of various solvents at 40° C. for 1 day. Form C was mostly amorphous and was isolated after evaporation of EtOH:H2O (3:1) over several hours.
ND: Not determined.

Form A of Compound 1 •p-Tosylate (Dry after DVS, See FIG. 28)

| # | 2-Theta | d(A) | BG | Height | I % |
|---|---|---|---|---|---|
| 1 | 7.412 | 11.9171 | 327 | 5931 | 100.0 |
| 2 | 9.800 | 9.0181 | 239 | 4499 | 75.9 |
| 3 | 10.806 | 8.1806 | 228 | 525 | 8.9 |
| 4 | 12.835 | 6.8913 | 204 | 176 | 3.0 |
| 5 | 13.410 | 6.5972 | 199 | 436 | 7.4 |
| 6 | 14.748 | 6.0014 | 210 | 1289 | 21.7 |
| 7 | 15.560 | 5.6904 | 290 | 770 | 13.0 |
| 8 | 16.031 | 5.5241 | 300 | 1077 | 18.2 |
| 9 | 17.136 | 5.1702 | 282 | 1159 | 19.5 |
| 10 | 17.651 | 5.0206 | 262 | 418 | 7.0 |
| 11 | 18.438 | 4.8081 | 237 | 893 | 15.1 |
| 12 | 18.735 | 4.7325 | 368 | 1232 | 20.8 |
| 13 | 18.970 | 4.6742 | 537 | 991 | 16.7 |
| 14 | 19.562 | 4.5341 | 405 | 2898 | 48.9 |
| 15 | 20.746 | 4.2780 | 288 | 340 | 5.7 |
| 16 | 21.278 | 4.1723 | 358 | 370 | 6.2 |
| 17 | 21.552 | 4.1198 | 301 | 875 | 14.8 |
| 18 | 21.899 | 4.0553 | 397 | 114 | 1.9 |
| 19 | 22.580 | 3.9345 | 353 | 703 | 11.9 |
| 20 | 23.033 | 3.8581 | 368 | 178 | 3.0 |
| 21 | 23.897 | 3.7206 | 338 | 133 | 2.2 |
| 22 | 24.237 | 3.6691 | 303 | 267 | 4.5 |
| 23 | 24.829 | 3.5829 | 329 | 241 | 4.1 |
| 24 | 25.124 | 3.5416 | 313 | 1713 | 28.9 |
| 25 | 25.933 | 3.4329 | 362 | 424 | 7.1 |
| 26 | 26.703 | 3.3356 | 386 | 238 | 4.0 |
| 27 | 26.957 | 3.3048 | 360 | 155 | 2.6 |
| 28 | 27.946 | 3.1901 | 357 | 2896 | 48.8 |
| 29 | 29.601 | 3.0153 | 237 | 293 | 4.9 |
| 30 | 30.428 | 2.9352 | 216 | 137 | 2.3 |
| 31 | 31.001 | 2.8823 | 203 | 233 | 3.9 |
| 32 | 31.537 | 2.8345 | 190 | 141 | 2.4 |
| 33 | 34.870 | 2.5709 | 198 | 126 | 2.1 |
| 34 | 35.399 | 2.5336 | 195 | 325 | 5.5 |

Form B of Compound 1 •p-Tosylate (Wet from THF)

| # | 2-Theta | d(A) | BG | Height | I % |
|---|---|---|---|---|---|
| 1 | 7.372 | 11.9811 | 208 | 391 | 7.8 |
| 2 | 7.824 | 11.2897 | 184 | 5036 | 100.0 |
| 3 | 10.032 | 8.8097 | 147 | 641 | 12.7 |
| 4 | 14.637 | 6.0467 | 125 | 85 | 1.7 |
| 5 | 15.678 | 5.6477 | 124 | 961 | 19.1 |
| 6 | 16.402 | 5.3999 | 116 | 98 | 1.9 |
| 7 | 16.901 | 5.2416 | 110 | 433 | 8.6 |
| 8 | 17.195 | 5.1528 | 132 | 67 | 1.3 |
| 9 | 18.337 | 4.8343 | 113 | 65 | 1.3 |
| 10 | 19.657 | 4.5124 | 135 | 491 | 9.7 |
| 11 | 20.154 | 4.4024 | 118 | 84 | 1.7 |
| 12 | 20.646 | 4.2984 | 119 | 357 | 7.1 |
| 13 | 23.109 | 3.8456 | 85 | 93 | 1.8 |
| 14 | 23.723 | 3.7475 | 89 | 92 | 1.8 |
| 15 | 26.644 | 3.3429 | 85 | 286 | 5.7 |
| 16 | 27.470 | 3.2442 | 90 | 87 | 1.7 |
| 17 | 28.163 | 3.1660 | 90 | 105 | 2.1 |
| 18 | 28.378 | 3.1424 | 87 | 193 | 3.8 |
| 19 | 29.564 | 3.0191 | 75 | 38 | 0.8 |
| 20 | 29.858 | 2.9900 | 72 | 82 | 1.6 |
| 21 | 31.257 | 2.8593 | 71 | 39 | 0.8 |
| 22 | 31.689 | 2.8213 | 65 | 80 | 1.6 |
| 23 | 35.098 | 2.5547 | 62 | 33 | 0.7 |
| 24 | 35.753 | 2.5093 | 60 | 54 | 1.1 |
| 25 | 36.187 | 2.4802 | 65 | 45 | 0.9 |

Definitions

Acetonitrile (ACN)
Differential Scanning Calorimetry (DSC)
Dynamic Vapor Sorption (DVS)
Ethanol (EtOH)

Ethyl Acetate (EtOAc)
Evaporative Light Scattering Detection (ELSD)
Isopropyl Alcohol (IPA)
Methanol (MeOH)
Methyl t-Butyl Ether (MTBE)
Nuclear Magnetic Resonance Spectroscopy (NMR)
Polarized Light Microscopy (PLM)
Tetrahydrofuran (THF)
Thermal Gravimetric Analysis (TGA)
X-ray Powder Diffraction (XRPD)

TABLE 9

| Instrumentation | | |
|---|---|---|
| Name | Model | Manu-facture |
| Differential Scanning Calorimeter (DSC) | Q2000 | TA |
| Dynamic Vapor Sorption Instrument (DVS) | Advantage-1 | SMS |
| High Performance Liquid Chromatograph (HPLC) | Agilent 1200 and 1260 | Agilent |
| Mass Spectrometer (MS) | QGA | Hiden |
| Nuclear Magnetic Resonance Spectrometer (NMR) | AVANCE III (400M Hz) | Bruker |
| Polarized Light Microscope (PLM) | LV100 PL | Nikon |
| Thermal Gravimetric Analyzer (TGA) | Q5000IR | TA |
| X-ray Powder Diffractometer (XRPD) | D8 advance | Bruker |

All publications cited herein are incorporated by reference in their entirety for all purposes. It should be understood that embodiments described herein should be considered as illustrative only, without limiting the scope of the invention. Descriptions of features or aspects within each embodiment should typically be considered as available for other similar features or aspects in other embodiments. While several embodiments have been described in the Examples above, it will be understood by those of ordinary skill in the art that various changes in form and details may be made therein without departing from the spirit and scope of the disclosure as defined by the following claims.

What is claimed is:

1. A crystalline form of the compound of Formula 1, or a pharmaceutical acceptably salt thereof:

1

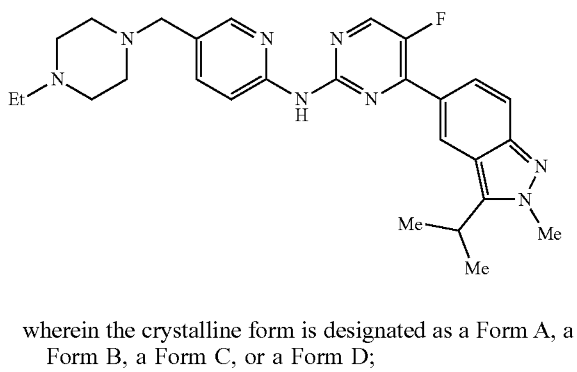

wherein the crystalline form is designated as a Form A, a Form B, a Form C, or a Form D;

wherein the Form A is characterized by an X-ray powder diffraction (XRPD) pattern comprising characteristic peaks at diffraction angles 2θ of approximately 5.9°, 11.9°, and 25.6°;

wherein the Form B is characterized by an X-ray powder diffraction pattern comprising any three (3) of characteristic any three (3) of peaks at diffraction angles 2° of approximately 4.7°, 11.2°, 14.1°, 15.3° and 21.2°;

wherein the Form C is characterized by an X-ray powder diffraction pattern comprising characteristic peaks at diffraction angles 2θ of approximately 6.4°, 12.8° and 20.7°; and wherein the Form D, is characterized by an X-ray powder diffraction pattern comprising any three (3) of characteristic peaks at diffraction angles 2θ of approximately 4.8°, 8.3°, 10.5°, 11.5°, and 14.0°.

2. The crystalline form of claim 1, wherein the Form A is further characterized by any of the follow: (a) the XRPD pattern comprises any three (3) of characteristic peaks at diffraction angles 2θ of approximately 5.6°, 5.9°, 11.9°, 16.5°, 25.6° and 26.2°; (b) the XRPD pattern comprises any three (3) of characteristic peaks, expressed in terms of the interplanar distance, at 15.7A, 14.9A, 7.5A, 5.4A, 3.5A and 3.4A; (c) a differential scanning calorimetry (DSC) profile comprising characteristic peaks at 100.3° C., 124.3° C. and 166.3° C., with a melting point having an onset temperature of approximately 162.3° C.; (d) an X-ray powder diffraction pattern as shown in FIG. 2A; and/or (e) a DSC profile as shown in FIG. 3.

3. The crystalline form of claim 1, wherein the crystalline Form B is further characterized by any of the following: (a) the X-ray powder diffraction pattern comprising any three (3) of characteristic peaks, expressed in terms of the interplanar distance, at 18.7A, 7.9A, 6.3A, 5.8A and 4.2A; (b) a DSC profile comprising characteristic peaks at 61.5° C., 118.8° C. and 166.8° C., with a melting point having an onset temperature of approximately 165.4° C.; (c) an X-ray powder diffraction pattern as shown in FIG. 4; and/or (d) a DSC profile as shown in FIG. 6.

4. The crystalline form of claim 1, wherein the crystalline Form C is further characterized by any of the following: (a) the X-ray powder diffraction pattern comprising any three (3) of characteristic peaks at diffraction angles 2θ of approximately 5.7°, 6.4°, 9.2°, 12.8°, 15.7° and 20.7°; (b) the X-ray powder diffraction pattern comprising any three (3) of characteristic peaks, expressed in terms of the interplanar distance, at 15.5A, 13.8A, 9.6A, 6.9A, 5.6A and 4.3A; (c) a DSC profile comprising a characteristic peak at 162.8° C., with a melting point having an onset temperature of approximately 160.9° C.; (d) an X-ray powder diffraction pattern as shown in FIG. 4; and/or (e) a DSC profile as shown in FIG. 7.

5. The crystalline form of claim 1, wherein the crystalline Form D is further characterized by any of the following: (a) the X-ray powder diffraction pattern comprising any three (3) of characteristic peaks at diffraction angles 2θ of approximately 18.2°, 20.0°, 23.5°, and 28.5°; (b) a DSC profile comprising characteristic peaks at 55.9° C., 118.8° C. and 168.4° C.; (c) an X-ray powder diffraction pattern as shown in FIG. 10; and/or (d) a DSC profile as shown in FIG. 8.

6. An acid addition salt of N-(5- ((4-Ethylpiperazin-yl) methyl)pyridin-2-yl-5-fluoro-4-(3-isopropyl-2-methyl-2H-indazol-5-yl) pyrimidin-2-amine in crystalline form, wherein the acid is hydrochloric acid (HCl), wherein the compound N-(5- ((4-ethylpiperazin-yl)methyl)pyridin-2-yl-5-fluoro-4-(3-isopropyl-2-methyl-2H-indazol-5- yl)pyrimidin-2-amine and hydrochloride (HCl) in about 1:1 molar ratio, in a crystalline form (Form A) characterized by an X-ray powder diffraction pattern comprising characteristic peaks at any three (3) of diffraction angles 2θ of approximately 4.7°, 9.2°, 11.2°, 19.5° and 28.3°.

7. The acid addition salt of claim 6, in a crystalline form (Form A) characterized by any of the following: (a) an X-ray powder diffraction pattern as shown in FIG. 18; (b) a DSC profile comprising characteristic peaks at 44.8° C. and 277.9° C., with a melting point having an onset temperature of approximately 275.4° C.; and/or (c) a TGA profile as shown in FIG. 16.

* * * * *